United States Patent
Zhang et al.

(10) Patent No.: US 11,801,386 B2
(45) Date of Patent: Oct. 31, 2023

(54) DEVICE AND METHOD FOR DETERMINING A CARDIAC SENSING CONTROL PARAMETER

(71) Applicant: Medtronic, Inc., Minneapolis, MN (US)

(72) Inventors: Xusheng Zhang, Shoreview, MN (US); Yuanzhen Liu, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 161 days.

(21) Appl. No.: 17/350,153

(22) Filed: Jun. 17, 2021

(65) Prior Publication Data

US 2021/0402190 A1 Dec. 30, 2021

Related U.S. Application Data

(60) Provisional application No. 63/145,687, filed on Feb. 4, 2021, provisional application No. 63/045,567, filed on Jun. 29, 2020.

(51) Int. Cl.
*A61N 1/37* (2006.01)
*A61N 1/39* (2006.01)
(Continued)

(52) U.S. Cl.
CPC ............ *A61N 1/3702* (2013.01); *A61B 5/341* (2021.01); *A61B 5/363* (2021.01); *A61B 5/4836* (2013.01);
(Continued)

(58) Field of Classification Search
CPC ................ A61N 1/3702; A61N 1/3625; A61N 1/39622; A61N 1/3621; A61N 1/3624;
(Continued)

(56) References Cited

U.S. PATENT DOCUMENTS 4,374,382 A * 2/1983 Markowitz .......... A61B 5/0031
600/509
6,216,036 B1 4/2001 Jenkins et al.
(Continued)

FOREIGN PATENT DOCUMENTS

WO 2019152383 A1 8/2019

OTHER PUBLICATIONS (PCT/US2021/038213) PCT Notification of Transmittal of the International Search Report and the Written Opinion of the International Searching Authority, dated Oct. 15, 2021, 14 pages.

*Primary Examiner* — Catherine M Voorhees

(57) ABSTRACT

A medical device processor is configured to receive a first cardiac electrical signal sensed from a first sensing electrode vector, receive a second cardiac electrical signal sensed from a second sensing electrode vector different than the first sensing electrode vector, and construct a third cardiac electrical signal from the first cardiac electrical signal and the second cardiac electrical signal. In some examples, the system determines sensed cardiac events according to at least one setting of a cardiac event sensing threshold control parameter from at least the third cardiac electrical signal and may determine at least one acceptable setting of a sensing control parameter based on the determined sensed cardiac events. The processor may generate an output representative of the determined sensed cardiac events.

19 Claims, 21 Drawing Sheets

(51) Int. Cl.
  *A61B 5/363* (2021.01)
  *A61B 5/341* (2021.01)
  *A61B 5/00* (2006.01)
  *A61N 1/362* (2006.01)
(52) U.S. Cl.
  CPC .......... *A61B 5/7435* (2013.01); *A61N 1/3625* (2013.01); *A61N 1/39622* (2017.08); *A61B 2560/02* (2013.01)
(58) Field of Classification Search
  CPC ...... A61N 1/3987; A61B 5/341; A61B 5/363; A61B 5/4836; A61B 5/7435; A61B 2560/02; A61B 5/361
  See application file for complete search history.

(56) References Cited

U.S. PATENT DOCUMENTS

| | | |
|---|---|---|
| 6,266,555 B1 | 7/2001 | Werner et al. |
| 6,301,503 B1 | 10/2001 | Hsu et al. |
| 6,505,067 B1 * | 1/2003 | Lee ................ A61B 5/341 600/509 |
| 7,242,978 B2 | 7/2007 | Cao et al. |
| 7,496,403 B2 | 2/2009 | Cao et al. |
| 8,521,269 B1 | 8/2013 | Gunderson et al. |
| 10,251,573 B2 | 4/2019 | Ousdigian et al. |
| 2007/0135864 A1 | 6/2007 | Gunderson et al. |
| 2008/0275518 A1 * | 11/2008 | Ghanem ............ A61N 1/3925 607/9 |
| 2011/0112597 A1 | 5/2011 | Snell et al. |

* cited by examiner

DEVICE AND METHOD FOR DETERMINING A CARDIAC SENSING CONTROL PARAMETER

REFERENCE TO RELATED APPLICATIONS

This application claims the benefit of U.S. Patent Application No. 63/145,687, filed provisionally on Feb. 4, 2021, and U.S. Patent Application No. 63/045,567, filed provisionally on Jun. 29, 2020, both of which are incorporated herein by reference in their entirety.

TECHNICAL FIELD

The disclosure relates generally to a medical device and method for determining a sensing control parameter to promote reliable sensing of cardiac event signals.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. A cardiac pacemaker or cardioverter defibrillator may sense cardiac electrical signals from the heart and deliver electrical stimulation therapies to the heart using electrodes carried by a transvenous medical electrical lead, a non-transvenous medical electrical lead and/or leadless electrodes coupled directly to the housing of the medical device.

The electrical stimulation therapies may include signals such as pacing pulses or cardioversion/defibrillation shocks. In some cases, a medical device may sense cardiac event signals attendant to the intrinsic or pacing-evoked depolarizations of the heart and control delivery of stimulation signals to the heart based on sensed cardiac event signals. Upon detection of an abnormal rhythm based on the sensed cardiac event signals (or absence thereof), such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion/defibrillation (CV/DF) shocks to the heart upon detecting tachycardia or fibrillation. Reliable sensing of the cardiac event signals attendant to myocardial depolarizations from cardiac electrical signals is important in controlling appropriate electrical stimulation therapies for the benefit of the patient.

SUMMARY

In general, the disclosure is directed to a device and method for determining sensed cardiac events from a cardiac electrical signal for use in identifying an acceptable or recommended setting of a sensing control parameter. The sensing control parameter may be, for example, a programmable sensing electrode vector or a cardiac event sensing threshold control parameter used in setting the amplitude of the sensing threshold used to sense cardiac event signals. A medical device system configured to sense cardiac electrical signals may include multiple available sensing electrode vectors, each vector being a different combination of electrodes selected from at least three electrodes, for sensing cardiac electrical signals. A medical device system operating according to the techniques disclosed herein senses two cardiac electrical signals using two different sensing electrode vectors and constructs at least one cardiac electrical signal from the two sensed cardiac electrical signals. The medical device system may determine sensed cardiac event signals from multiple cardiac electrical signals, sensed and constructed, according to one or more settings of a cardiac event sensing threshold control parameter for use in determining an acceptable or recommended setting of a sensing control parameter.

In one example, the disclosure provides a medical device comprising a processor configured to receive at least a first sensed cardiac electrical signal and a second sensed cardiac electrical signal and construct a third cardiac electrical signal from the first sensed cardiac electrical signal and the second sensed cardiac electrical signal. The processor determines sensed cardiac events according to at least one setting of a cardiac event sensing threshold control parameter from at least the third cardiac electrical signal and generates an output representative of the determined sensed cardiac events.

In another example, the disclosure provides a method that includes receiving at least a first sensed cardiac electrical signal and a second sensed cardiac electrical signal and constructing a third cardiac electrical signal from the first sensed cardiac electrical signal and the second sensed cardiac electrical signal. The method further includes determining sensed cardiac events from at least the third cardiac electrical signal according to at least one setting of a cardiac event sensing threshold control parameter and generating an output representative of the determined sensed cardiac events.

In another example, the disclosure provides a non-transitory computer-readable medium storing a set of instructions which, when executed by processing circuitry of a medical device system, cause the processing circuitry to receive at least a first sensed cardiac electrical signal and a second sensed cardiac electrical signal and construct a third cardiac electrical signal from the first sensed cardiac electrical signal and the second sensed cardiac electrical signal. The instructions further cause the processing circuitry to determine sensed cardiac events from at least the third cardiac electrical signal according to at least one setting of a cardiac event sensing threshold control parameter and generate an output representative of the determined sensed cardiac events.

In another example, the disclosure provides a graphical user interface system including a processor configured to receive a cardiac electrical signal, determine sensed cardiac events from the cardiac electrical signal according to at least one setting of a sensing threshold control parameter and generate an output of data representative of the determined sensed cardiac events. The graphical user interface system further includes a display unit coupled to the processor and configured to receive the generated output of data from the processor and display a visual representation of the data representative of the determined sensed cardiac events.

Further disclosed herein is the subject matter of the following clauses:

1. A medical device comprising a processor configured to:
   receive at least a first sensed cardiac electrical signal and a second sensed cardiac electrical signal;

construct a third cardiac electrical signal from the first sensed cardiac electrical signal and the second sensed cardiac electrical signal;

from at least the third cardiac electrical signal, determine sensed cardiac events according to at least one setting of a cardiac event sensing threshold control parameter; and generate an output representative of the determined sensed cardiac events.

2. The device of clause 1 wherein:

the device includes a display unit;

the processor is configured to:

determine an acceptable setting of at least one of a sensing electrode vector and a cardiac event sensing threshold control parameter; and generate the output representative of the determined sensed cardiac events comprising the acceptable setting;

the display unit being configured to display the acceptable setting.

3. The device of any of clauses 1-2, wherein the processor is configured to determine the sensed cardiac events according to a plurality of settings of the cardiac event sensing threshold control parameter by adjusting at least one of a sensitivity, a starting amplitude of a cardiac event sensing threshold amplitude, an intermediate amplitude of the cardiac event sensing threshold amplitude, or a time interval used for timing an adjustment to the cardiac event sensing threshold.

4. The device of any of clauses 1-3, wherein the processor is configured to determine at least one acceptable sensing control parameter setting based on the determined sensed cardiac events by:

determining a rate of the determined sensed cardiac events;

determining that the rate meets expected rate criteria; and determining that an associated sensing control parameter used to determine the sensed cardiac events is an acceptable sensing control parameter in response to the rate meeting the expected rate criteria.

5. The device of any of clauses 1-4, wherein the processor is configured to:

detect a tachyarrhythmia based on the determined sensed cardiac events from at least one of the first cardiac electrical signal, the second cardiac electrical signal or the third cardiac electrical signal; and determine at least one acceptable setting of a sensing control parameter by identifying a sensing control parameter associated with the detected tachyarrhythmia.

6. The device of clause 5, wherein the processor is configured to:

determine a time to detect the tachyarrhythmia for each of a plurality of settings of the cardiac event sensing threshold control parameter for a given one of the first cardiac electrical signal, second cardiac electrical signal and third cardiac electrical signal; and determine the at least one acceptable setting of the sensing control parameter from among the plurality of settings of the cardiac event sensing threshold control parameter associated with a determined time to detect the tachyarrhythmia that is within a tachyarrhythmia detection time limit.

7. The device of clause 6, wherein the processor is further configured to determine the tachyarrhythmia detection time limit by:

determining a minimum time to detect the tachyarrhythmia among the times to detect the tachyarrhythmia determined for the plurality of settings of the sensing threshold control parameter; and determining the tachyarrhythmia detection time limit as the minimum time plus a predetermined increase in the time to detect the tachyarrhythmia.

8. The device of any of clauses 6-7, wherein the processor is further configured to determine the at least one acceptable sensing control parameter setting by:

determining a highest value of a sensitivity setting associated with a time to detect the tachyarrhythmia that is less than or equal to the tachyarrhythmia detection time limit;

determine an acceptable sensitivity setting that is a factor of the highest value, wherein the factor corresponds to a predetermined safety margin for sensing cardiac event signals.

9. The device of any of clauses 1-8, comprising:

a telemetry unit configured to receive the first cardiac electrical signal and the second cardiac electrical signal transmitted from another medical device;

wherein the processor is configured to:

receive the first cardiac electrical signal and the second cardiac electrical signal from the telemetry unit, where the first cardiac electrical signal corresponds to a first sensing electrode vector comprising a first electrode and a second electrode, the second cardiac electrical signal corresponds to a second sensing electrode vector comprising the first electrode and a third electrode, and construct the third cardiac electrical signal corresponding to a third sensing electrode vector including the second electrode and the third electrode.

10. The device of any of clauses 1-9, comprising:

a sensing circuit configured to:

sense the first cardiac electrical signal from a first sensing electrode vector comprising a first electrode and a second electrode;

sense a second cardiac electrical signal from a second sensing electrode vector comprising the first electrode and a third electrode; and the processor is configured to receive the first cardiac electrical signal and the second cardiac electrical signal from the sensing circuit and construct the third cardiac electrical signal corresponding to a third sensing electrode vector including the second electrode and the third electrode.

11. The device of any of clauses 1-9 further comprising a display unit, wherein the processor is configured to generate the output by generating data corresponding to the determined sensed cardiac events for display by the display unit in a graphical user interface.

12. The device of clause 11, wherein the processor is configured to receive a user input indicating the at least one setting of the cardiac event sensing threshold control parameter.

13. The device of any of clauses 11-12, wherein the processor is configured to:

receive a user input indicating a sensing electrode vector; and construct the third cardiac electrical signal corresponding the sensing electrode vector.
14. The device of any of clauses 11-13, wherein the processor is configured to:
receive a user input indicating a selection of at least one sensing control parameter setting from the displayed graphical user interface; and
generate the output comprising a programming command corresponding to the user input indicating the selection of the at least one sensing control parameter.
15. The device of clause 14, wherein the processor is configured to receive the user input indicating the selection of at least one sensing control parameter setting from the displayed graphical user interface as a combination of a sensing electrode vector and a cardiac event sensing threshold control parameter.
16. The device of any of clauses 2-15, further comprising a telemetry unit configured to transmit a programming command including the acceptable sensing control parameter setting.
17. A method comprising:
receiving at least a first sensed cardiac electrical signal and a second sensed cardiac electrical signal;
constructing a third cardiac electrical signal from the first sensed cardiac electrical signal and the second sensed cardiac electrical signal;
from at least the third cardiac electrical signal, determining sensed cardiac events according to at least one setting of a cardiac event sensing threshold control parameter; and generating an output representative of the determined sensed cardiac events.
18. The method of clause 17, comprising:
determining an acceptable setting of at least one of a sensing electrode vector and a cardiac event sensing threshold control parameter;
generating the output representative of the determined sensed cardiac events comprising the acceptable setting; and
displaying the acceptable setting by a display unit.
19. The method of any of clauses 17-18, comprising determining the sensed cardiac events according to a plurality of settings of the cardiac event sensing threshold control parameter by adjusting at least one of a sensitivity, a starting amplitude of a cardiac event sensing threshold amplitude, an intermediate amplitude of the cardiac event sensing threshold amplitude, or a time interval used for timing an adjustment to the cardiac event sensing threshold amplitude.
20. The method of any of clauses 17-19, further comprising determining at least one acceptable sensing control parameter setting based on the determined sensed cardiac events by:
determining a rate of the determined sensed cardiac events;
determining that the rate meets expected rate criteria; and
determining that an associated sensing control parameter used to determine the sensed cardiac events is the acceptable sensing control parameter in response to the rate meeting the expected rate criteria.
21. The method of any of clauses 17-20, further comprising
detecting a tachyarrhythmia based on the determined sensed cardiac events from at least one of the first cardiac electrical signal, the second cardiac electrical signal or the third cardiac electrical signal;
determining at least one acceptable setting of a sensing control parameter by identifying a sensing control parameter associated with the detected tachyarrhythmia.
22. The method of clause 21, comprising:
determining a time to detect the tachyarrhythmia for each of a plurality of settings of the cardiac event sensing threshold control parameter for a given one of the first cardiac electrical signal, second cardiac electrical signal and third cardiac electrical signal; and
determining the at least one acceptable setting of the sensing control parameter by identifying one of the plurality of settings of the cardiac event sensing threshold control parameter associated with a time to detect the tachyarrhythmia that is within a tachyarrhythmia detection time limit.
23. The method of clause 22, wherein determining the tachyarrhythmia detection time limit comprises:
determining a minimum time to detect the tachyarrhythmia among the times to detect the tachyarrhythmia determined for the plurality of settings of the sensing threshold control parameter; and
determining the tachyarrhythmia detection time limit as the minimum time plus a predetermined increase in the time to detect the tachyarrhythmia.
24. The method of any of clauses 22-23, wherein determining the at least one acceptable setting of the sensing control parameter comprises:
determining a highest value of a sensitivity setting associated with a time to detect the tachyarrhythmia that is less than or equal to the tachyarrhythmia detection time limit;
determining the acceptable setting of the sensing control parameter as a sensitivity setting that is a factor of the highest value, wherein the factor corresponds to a predetermined safety margin for sensing cardiac event signals.
25. The method of any of clauses 17-24, comprising:
receiving the first cardiac electrical signal and the second cardiac electrical signal transmitted from another medical device, where the first cardiac electrical signal corresponds to a first sensing electrode vector comprising a first electrode and a second electrode, the second cardiac electrical signal corresponds to a second sensing electrode vector comprising the first electrode and a third electrode, and
constructing the third cardiac electrical signal corresponding to a third sensing electrode vector including the second electrode and the third electrode.
26. The method of any of clauses, 17-25, comprising:
sensing the first cardiac electrical signal from a first sensing electrode vector comprising a first electrode and a second electrode;
sensing a second cardiac electrical signal from a second sensing electrode vector comprising the first electrode and a third electrode; and
constructing the third cardiac electrical signal corresponding to a third sensing electrode vector including the second electrode and the third electrode.
27. The method of any of clauses 17-26, wherein generating the output comprises:
generating data corresponding to the determined sensed cardiac events; and displaying the generated data in a graphical user interface.

28. The method of clause 27, comprising receiving a user input, the user input indicating the at least one setting of the cardiac event sensing threshold control parameter.

29. The method of any of clauses 27-28, comprising:
  receiving a user input indicating a sensing electrode vector; and
  constructing the third cardiac electrical signal corresponding the sensing electrode vector.

30. The method of any of clauses 27-29, comprising:
  receiving a user input indicating a selection of at least one sensing control parameter setting from the displayed graphical user interface;
  wherein generating the output comprises generating a programming command corresponding to the user input indicating the selection of the at least one sensing control parameter.

31. The method of clause 27, comprising receiving the user input indicating the selection of at least one sensing control parameter setting from the display as a combination of a sensing electrode vector and a cardiac event sensing threshold control parameter.

32. The method of any of clauses 18-31, comprising transmitting a programming command including the acceptable sensing control parameter setting.

33. A non-transitory computer-readable medium storing a set of instructions which, when executed by a processor of a medical device, cause the device to:
  receive at least a first sensed cardiac electrical signal and a second sensed cardiac electrical signal;
  construct a third cardiac electrical signal from the first sensed cardiac electrical signal and the second sensed cardiac electrical signal;
  from at least the third cardiac electrical signal, determine sensed cardiac events according to at least one setting of a cardiac event sensing threshold control parameter; and
  generate an output representative of the determined sensed cardiac events.

34. A graphical user interface system comprising:
  a processor configured to:
    obtain a plurality of cardiac electrical signals sensed via a plurality of sensing electrode vectors;
    predict, for each of a plurality of cardiac electrical signals, whether tachyarrhythmia detection is expected to be made from the corresponding cardiac electrical signal at a plurality of sensitivity settings;
    determine one or more acceptable sensitivity settings of at least one of the plurality of sensing electrode vectors based on at least the predictions; and
    generate an output of data representative of acceptable sensitivity settings for tachyarrhythmia detection for the respective plurality of sensing electrode vectors; and
  a display unit coupled to the processor and configured to:
    receive the generated output of data from the processor; and
    display a visual representation of the acceptable sensitivity settings for tachyarrhythmia detection for the respective plurality of sensing electrode vectors.

35. The graphical user interface system of clause 34, wherein the processor is configured to:
  determine one or more acceptable sensitivity settings of at least one of plurality of sensing electrode vectors by determining a recommended sensitivity setting for one of the plurality of sensing electrode vectors based on at least the predictions; and
  generate the output of data to include the recommended sensitivity setting.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
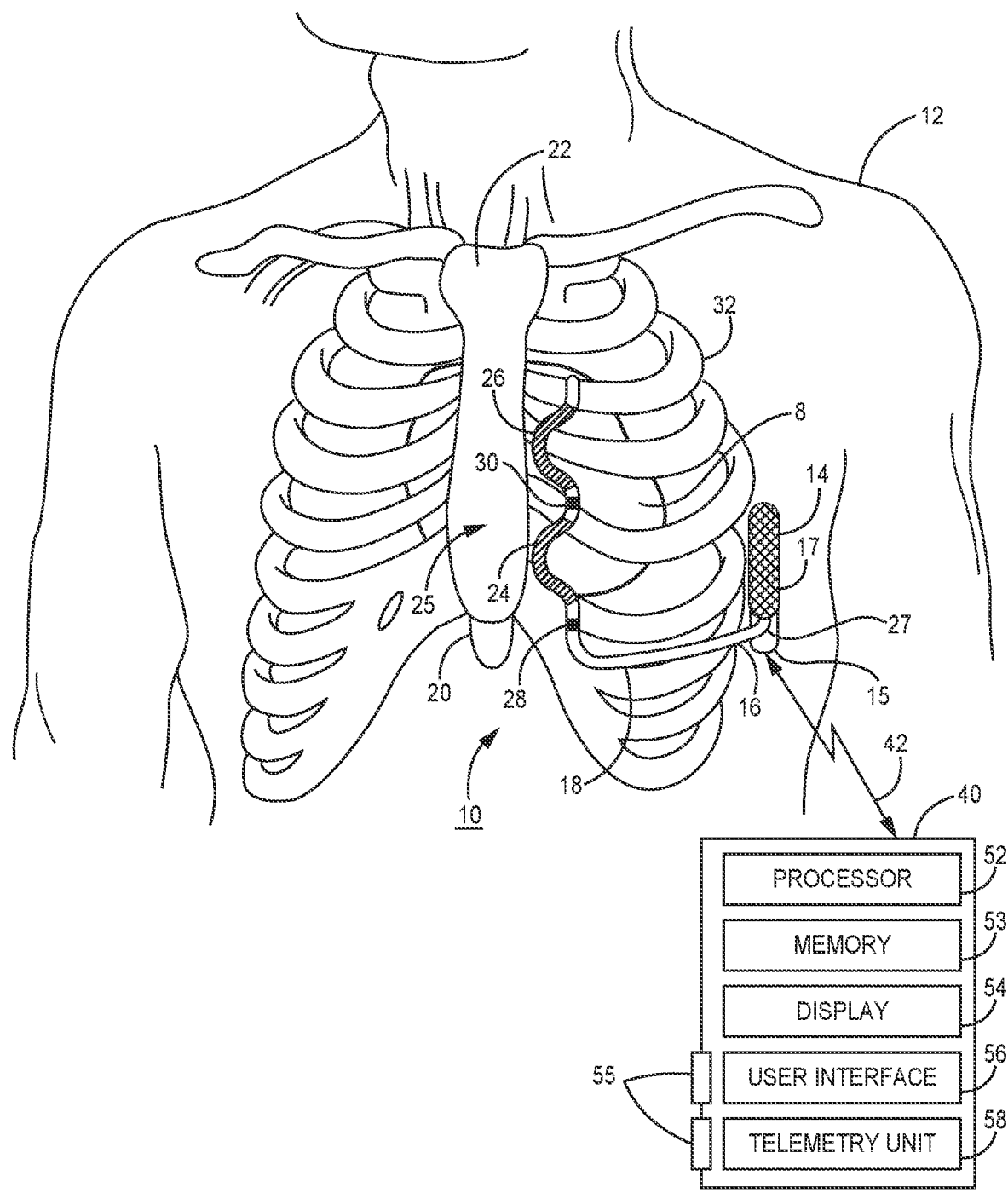
FIGS. 1A and 1B are conceptual diagrams of a medical device system configured to sense cardiac electrical signals and deliver cardiac electrical stimulation therapies according to one example.

In general, this disclosure describes a device and techniques for determining sensed cardiac events according to different sensing control parameters. Cardiac events may be sensed by a medical device according to programmed sensing control parameters for determining a cardiac rate and for detecting an abnormal cardiac rhythm, e.g., bradycardia, tachycardia, asystole, etc., for controlling the delivery of cardiac electrical stimulation therapy as needed. The "cardiac event" being sensed is an event associated with a single cardiac cycle such as an R-wave attendant to ventricular depolarization or a P-wave attendant to atrial depolarization. A cardiac event is determined to be sensed when a cardiac electrical signal crosses a cardiac event sensing threshold. Determining sensed cardiac events is therefore equivalent to determining a cardiac event sensing threshold crossing time by a cardiac electrical signal in some examples. Sensing control parameters used to determine sensed cardiac events from a cardiac electrical signal include the sensing electrode vector used to sense the cardiac electrical signal and cardiac event sensing threshold control parameters used to set the amplitude of the cardiac event sensing threshold at any given time during a cardiac cycle.

Cardiac events may be sensed for detecting cardiac arrhythmias. For example, the rate of sensed cardiac events may be determined by a medical device for detecting atrial or ventricular tachyarrhythmia, such as atrial tachycardia (AT), atrial fibrillation (AF), ventricular tachycardia (VT) or ventricular fibrillation (VF). In other examples, the rate of sensed cardiac events may be determined for controlling cardiac pacing for treating bradycardia, asystole, long ventricular pause or other abnormal rhythms or conduction abnormalities. In some examples, one or more alternative settings of a cardiac event sensing threshold control parameter is used for determining cardiac events that are sensed for a given cardiac electrical signal. The cardiac electrical signal may be sensed using electrodes in a selected sensing electrode vector or may be a constructed cardiac electrical signal that is derived from two sensed cardiac electrical signals. One or more cardiac event sensing threshold control parameter settings may be applied to one or more sensed and/or constructed cardiac electrical signals during real time and/or during post processing signal analysis to determine sensed cardiac events. The determined sensed cardiac events may be used to predict cardiac event intervals and/or a cardiac event rate that would be determined from the cardiac electrical signal based on the applied sensing threshold control parameters.

In some examples, the determination of cardiac event rates or intervals according to different sensing control parameter settings may be used to determine whether an arrhythmia detection would be detected and/or a predicted time of arrhythmia detection and/or therapy delivery. For instance, this determination may be used to determine a time required to detect a tachyarrhythmia episode. Using the predicted tachyarrhythmia detections and or predicted times to detect a tachyarrhythmia episode from a cardiac electrical signal according to multiple cardiac event sensing threshold control parameter settings, a medical device operating according to the techniques disclosed herein may determine acceptable settings of at least one sensing control parameter, such as the sensing electrode vector, sensitivity, or other cardiac event sensing threshold control parameters used to set the cardiac event sensing threshold amplitude during a cardiac cycle. The acceptable settings are likely to promote reliable sensing of cardiac events for detection of tachyarrhythmia and promote appropriate and timely therapy delivery as needed.

The techniques disclosed herein for determining sensed cardiac events and analyzing the rate and/or intervals of sensed cardiac events according to different sensing control parameter settings may be implemented in a device associated with a variety of cardiac device systems, such as a system including a cardiac monitor, pacemaker or ICD configured for sensing cardiac events and determining a cardiac event interval or rate for detecting a cardiac rhythm and, in some cases, controlling a cardiac electrical stimulation therapy. At least a portion of the techniques disclosed herein may be performed by a processor of an implantable medical device, such as a cardiac monitor, pacemaker or ICD, or by a processor of an external device configured to sense cardiac electrical signals or receive sensed cardiac electrical signals from another device.

In the illustrative examples presented herein, a pacemaker or ICD is configured to sense cardiac electrical signals and deliver cardiac electrical stimulation pulses for pacing and/or CV/DF therapy delivery. The pacemaker or ICD may be coupled to a transvenous or non-transvenous lead in various examples for carrying electrodes for sensing cardiac electrical signals and delivering electrical stimulation therapy. For example, the pacemaker or ICD may be coupled to an "extra-cardiovascular" lead, referring to a lead that positions electrodes outside the blood vessels, heart, and pericardium surrounding the heart of a patient. Implantable electrodes carried by extra-cardiovascular leads, for example, may be positioned extra-thoracically (outside the ribcage and sternum) or intra-thoracically (beneath the ribcage or sternum, sometimes referred to as a sub-sternal position) but may not necessarily be in intimate contact with myocardial tissue. An extra-cardiovascular lead may also be referred to as a "non-transvenous" lead.

In other examples, the medical device may be coupled to a transvenous lead that positions electrodes within a blood vessel, which may remain outside the heart in an "extra-cardiac" location or be advanced to position electrodes within a heart chamber. For instance, a transvenous medical lead may be advanced along a venous pathway to position electrodes in an extra-cardiac location within the internal thoracic vein (ITV), an intercostal vein, the superior epigastric vein, or the azygos, hemiazygos, or accessory hemiazygos veins, as examples. In still other examples, a transvenous lead may be advanced to position electrodes within the heart, e.g., within an atrial and/or ventricular heart chamber.

More generally, the disclosed techniques may be used in conjunction with any device that is configured to determine a rate or intervals of sensed cardiac events, which may include implantable or external pacemakers and defibrillators and implantable or external heart rate monitors, which may use skin or surface electrodes for sensing cardiac electrical signals. The techniques disclosed herein are not dependent on the particular type of sensing electrodes used or their position, either internal or external. The medical devices shown in FIGS. 1A-3 are examples of medical devices that may be implemented in a system performing techniques disclosed herein with no limitation intended.

Figure 1B:
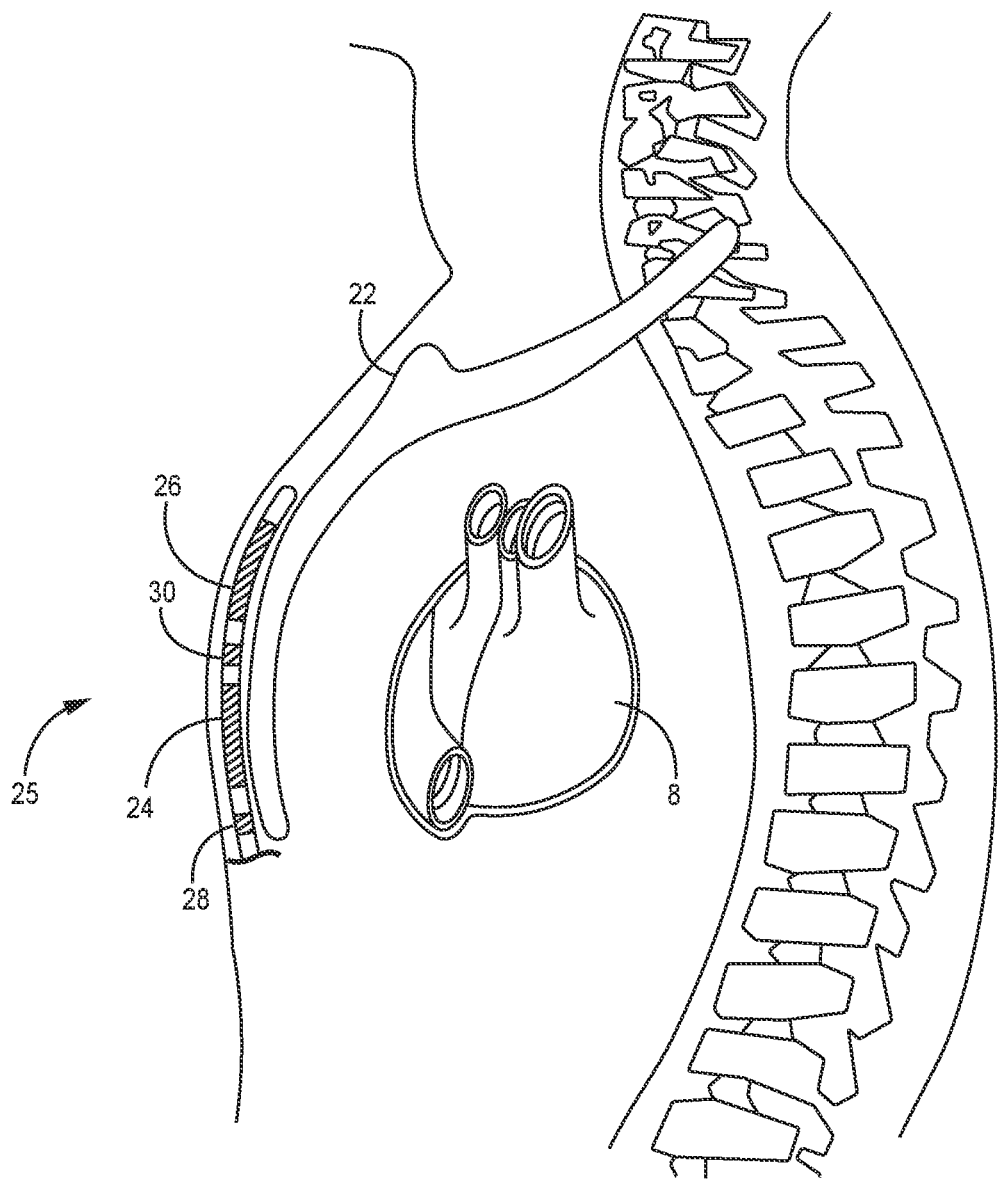

FIGS. 1A and 1B are conceptual diagrams of a medical device system 10 configured to sense cardiac events from a cardiac electrical signal and deliver cardiac electrical stimulation therapies according to one example. System 10 includes an ICD 14 connected to a non-transvenous, extra-cardiovascular electrical stimulation and sensing lead 16. FIG. 1A is a front view of ICD 14 implanted within patient 12. FIG. 1B is a side view of ICD 14 implanted within patient 12. FIGS. 1A and 1B are described in the context of an ICD system 10 capable of providing high voltage CV/DF shocks and in some examples cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 is shown in this example as an extracardiovascular lead implanted outside the ribcage and sternum. Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they may be utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing electrode vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage cardiac pacing pulses in some configurations. Electrodes 28 and 30 are referred to herein as "pace/sense electrodes" because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may sense cardiac electrical signals corresponding to electrical activity of heart 8 via one or more sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

Lead 16 may extend subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 may bend or turn to extend superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of non-transvenous, extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a cardiac electrical signal sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit cardiac electrical signals sensed from the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes may include a curving, serpentine, undulating or zig-zagging distal portion of the lead body 18. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the rate of sensed cardiac events and the morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver anti-tachycardia pacing (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses, asystole pacing pulses, or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor 52, memory 53, display unit 54, user interface 56 and telemetry unit 58. Processor 52 controls external device operations and processes data and signals received from ICD 14.

Processor 52 executes instructions stored in memory 53. Processor 52 may include any one or more of a microprocessor, a controller, a digital signal processor (DSP), an application specific integrated circuit (ASIC), a field-programmable gate array (FPGA), or equivalent discrete or analog logic circuitry. In some examples, processor 52 may include multiple components, such as any combination of one or more microprocessors, one or more controllers, one or more DSPs, one or more ASICs, or one or more FPGAs, as well as other discrete or integrated logic circuitry. The functions attributed to processor 52 herein may be embodied as software, firmware, hardware or any combination thereof.

Display 54, which may include a graphical user interface (GUI), displays data and other information to a user for reviewing ICD operation and programmed parameters as well as cardiac electrical signals retrieved from ICD 14. As described below, processor 52 may receive sensed cardiac electrical signals from ICD 14 for processing and analysis according to the techniques disclosed herein. External device processor 52 may be configured to determine sensed cardiac events from a cardiac electrical signal corresponding to a specified sensing electrode vector and according to one or more different sensing control parameters used to set the cardiac event sensing threshold amplitude. Processor 52 may be configured to determine a cardiac event rate or cardiac event intervals based on the determined sensed cardiac events. Based on the determined cardiac event rate or cardiac event intervals, processor 52 may determine an acceptable setting of a sensing control parameter for reliable cardiac event sensing.

Based on the determined cardiac event intervals, for example, processor 52 may determine whether a tachyarrhythmia detection is expected to be made from the determined cardiac events and may determine a time interval until a predicted tachyarrhythmia detection by ICD 14. Processor 52 may generate a display of data related to the processing and analysis of cardiac electrical signals on display unit 54, as further described below. The generated data display may include an acceptable or recommended setting for one or more sensing control parameters determined by processor 52. The generated display may be a GUI that a user may interact with for selecting sensing control parameters to be applied for determining sensed cardiac events and/or for authorizing and initiating programming of recommended settings determined by processor 52.

Memory 53 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 53 may be configured to store sensing control parameters and associated programmable settings. Memory 53 may store sensed cardiac event data determined by processor 52 for use in generating an output representative of the determined sensed cardiac events as disclosed herein.

User interface 56 may include a mouse, touch screen, keypad or the like to enable a user to interact with external device 40 to initiate a telemetry session with ICD 14 for retrieving data from and/or transmitting data to ICD 14, including programmable parameters for controlling cardiac event sensing and therapy delivery. A clinician may use user interface 56 to send and receive commands to ICD 14 via external device 40. As described herein, a clinician may use user interface 56 to specify one or more cardiac event sensing control parameters. Typically, user interface 56 includes one or more input devices and one or more output devices, including display unit 54. The input devices of user interface 56 may include a communication device such as a network interface, keyboard, pointing device, voice responsive system, video camera, biometric detection/response system, button, sensor, mobile device, control pad, microphone, presence-sensitive screen, touch-sensitive screen (which may be included in display unit 54), network, or any other type of device for detecting input from a human or machine.

The one or more output devices of user interface 56 may include a communication unit such as a network interface, display, sound card, video graphics adapter card, speaker, presence-sensitive screen, one or more USB interfaces, video and/or audio output interfaces, or any other type of device capable of generating tactile, audio, video, or other output. Display unit 54 may function as an input and/or output device using technologies including liquid crystal displays (LCD), quantum dot display, dot matrix displays, light emitting diode (LED) displays, organic light-emitting diode (OLED) displays, cathode ray tube displays, e-ink, or monochrome, color, or any other type of display capable of generating tactile, audio, and/or visual output. In other examples, user interface 56 may produce an output to a user in another fashion, such as via a sound card, video graphics adapter card, speaker, presence-sensitive screen, touch-sensitive screen, one or more USB interfaces, video and/or audio output interfaces, or any other type of device capable of generating tactile, audio, video, or other output. In some examples, display unit 54 is a presence-sensitive display that may serve as a user interface device that operates both as one or more input devices and one or more output devices.

Telemetry unit 58 includes a transceiver and antenna configured for bidirectional communication with a telemetry circuit included in ICD 14 and is configured to operate in conjunction with processor 52 for sending and receiving data relating to ICD functions via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including cardiac electrical signals or associated data derived therefrom, results of device diagnostics, and histories of detected rhythm episodes and delivered therapies, may be retrieved from ICD 14 by external device 40 following an interrogation command. In particular, external device 40 may retrieve episodes of sensed cardiac electrical signals from ICD 14.

For example, as described below, external device 40 may retrieve an episode of at least two different cardiac electrical signals sensed by ICD 14 using at least two different sensing electrode vectors for processing and analysis by processor 52. Processor 52 may construct at least one cardiac electrical signal from two or more sensed cardiac electrical signals received from ICD 14. Processor 52 may determine a sensed cardiac event rate and/or sensed cardiac event intervals from each cardiac electrical signal, sensed and constructed, based on one or more different cardiac event sensing threshold control parameter settings for use in determining a recommended sensing control parameter setting. The processing and analysis performed by processor 52 may be performed in real time as cardiac electrical signals are sensed by ICD 14 and transmitted to external device 40. Alternatively, processor 40 may perform processing and analysis of previously sensed cardiac electrical signal episodes that are stored by ICD 14 and transmitted to external device 40.

External device 40 may be used to program sensing control parameters, cardiac rhythm detection parameters and therapy delivery control parameters used by ICD 14. External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or handheld device, which may be a tablet, cell phone or other personal device. While external device 40 is shown only in FIG. 1A, it is to be understood that portions of the techniques disclosed herein may be performed by an external device, such as device 40, configured to communicate with an implantable or another external medical device configured to sense and transmit cardiac electrical signals to external device 40. Aspects of external device 40 may generally correspond to the external programming/monitoring unit disclosed in U.S. Pat. No. 5,507,782 (Kieval, et al.), hereby incorporated herein by reference in its entirety. An example programmer that may be configured to perform the techniques disclosed herein is the CARELINK® Programmer, commercially available from Medtronic, Inc., Minneapolis, Minnesota USA.

In some examples, external device 40 includes external ports 55 adapted to an interface of one or more external leads that include electrodes for sensing an electrocardiogram. In some examples, external device 40 may receive, via the one or more electrodes of the one or more external leads, electrocardiogram data from the patient or from another electrocardiogram input source. The electrocardiogram may be received by processor 52 for determining a heart rate, which may be used in establishing expected cardiac rate criteria for comparing to determined sensed cardiac event data in identifying acceptable sensing control parameters. In some examples, lead 16 may be coupled to external device 40, e.g., via external ports 55 and any necessary electrical connectors or adaptors. In this case, external device 40 is configured to receive cardiac electrical signals sensed via electrodes carried by lead 16 prior to coupling lead 16 to ICD 14, without requiring wireless transmission of the sensed cardiac electrical signals to external device 40. A subcutaneous or cutaneous patch electrode or other electrode may be temporarily positioned at an approximate implant site of ICD 14 to serve as a substitute electrode for ICD housing 15. At least two sensing electrode vectors may be selected from the electrodes carried by lead 16. In some examples, the electrode positioned temporarily as a substitute for the ICD housing 15 may be selected in one or both of the sensing electrode vectors to approximate a sensing electrode vector that includes ICD housing 15 and an electrode carried by lead 16. Processing and analysis of cardiac electrical signals sensed using lead 16 for selecting sensing control parameters may therefore be performed by external device processor 52 prior to connecting and implanting ICD 14. In this way, a clinician can verify that an acceptable implant position of lead 16 associated with acceptable settings of the sensing control parameters can be achieved for reliably sensing cardiac event signals and tachyarrhythmias based on output generated by external device processor 52, prior to implanting ICD 14.

Figure 1C:
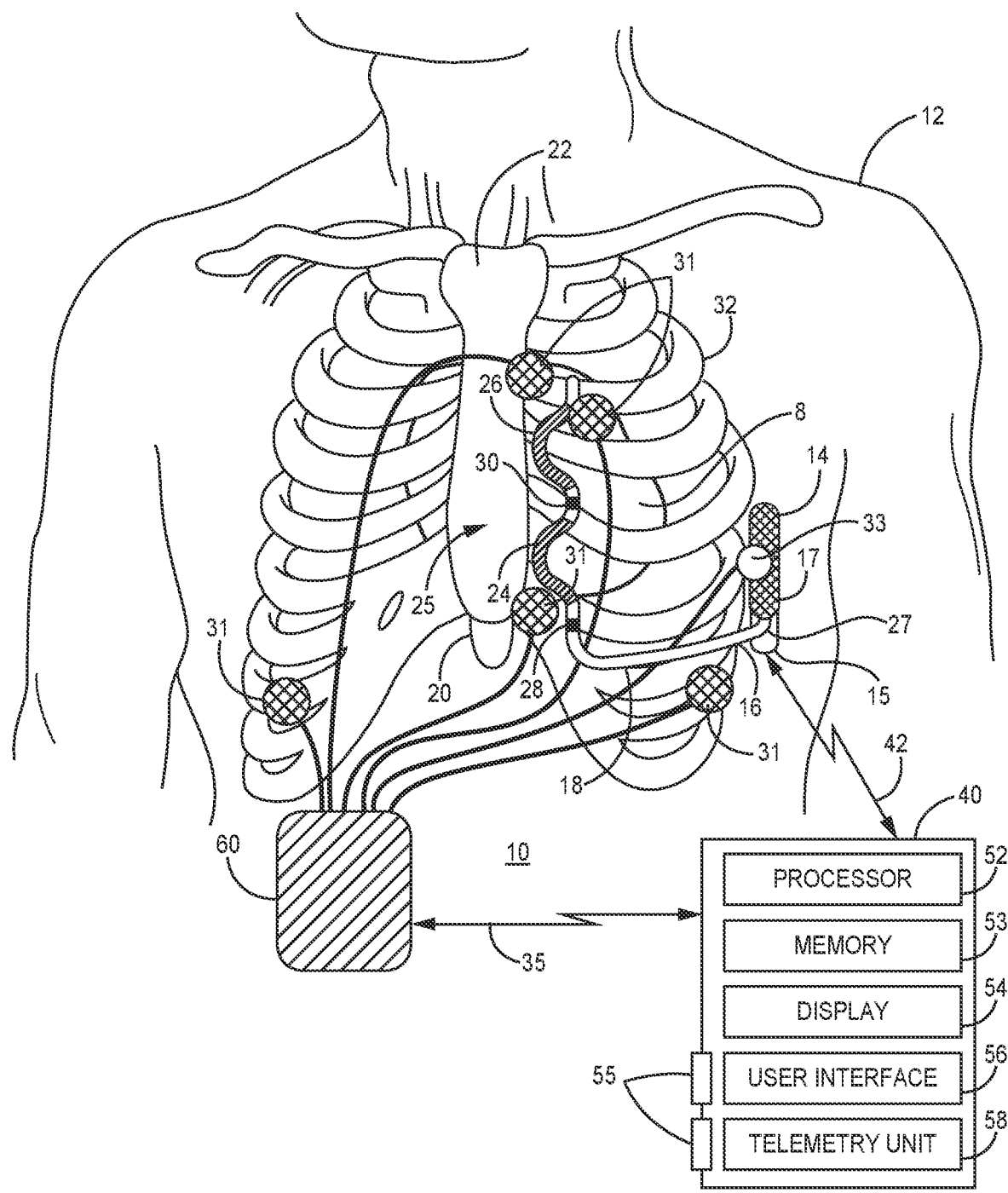
FIG. 1C is a conceptual diagram of a medical device system including an external cardiac monitor capable of wireless communication with an ICD for receiving cardiac electrical signals sensed by the ICD and/or sensing surface electrocardiogram signals.

FIG. 1C is a conceptual diagram of medical device system 10 and an external cardiac monitor 60. Cardiac monitor 60 may be coupled to multiple surface electrodes 31 for sensing surface electrocardiogram (ECG) signals. In some examples, the surface electrodes 31 may be positioned over and in approximate alignment with implanted electrodes coupled to ICD 14 or approximate locations of electrodes that are to be implanted and coupled to an ICD. The locations of surface electrodes 31 as shown in FIG. 1C are illustrative in nature. Surface electrodes 31 may be positioned at other locations corresponding to approximate subcutaneous, substernal or intravenous locations of implanted electrodes or targeted locations of implantable electrodes that are not yet implanted. Surface ECG signals may be acquired by cardiac monitor 60, e.g., during an induced tachyarrhythmia during an office visit or implant procedure or during a spontaneous tachyarrhythmia during ambulatory monitoring of patient 12.

A processor included in cardiac monitor 60 may receive, process and analyze the surface ECG signals to determine acceptable or recommended sensing control parameter settings for use by the ICD 14 when coupled to implantable electrodes corresponding to locations and associated sensing electrode vectors simulated by the surface electrode locations. In other examples, the surface ECG signals may be transmitted to external device 40 for processing and analysis by external device processor 52. The surface ECG signals may be used by the processor of cardiac monitor 60 or external device 40 to construct at least one additional ECG signal corresponding to a different sensing electrode vector than the vectors used to sense the surface ECG signals. The constructed ECG signal may be correlated to a sensing electrode vector between implantable electrodes that are or will be coupled to ICD 14. The constructed ECG signal analyzed according to the techniques disclosed herein for determining recommended or acceptable sensing control parameters that may be programmed into ICD 14 for use in sensing cardiac signals and detecting tachyarrhythmia. In this manner, acceptable sensitivity control parameter settings could be identified prior to implanting ICD 14 and/or lead 16. This technique may be utilized as part of a pre-screening procedure alone or in conjunction with other screening criteria to ensure a patient is an appropriate candidate for the system.

In addition to or alternatively to sensed surface ECG signals, cardiac monitor 60 may be capable of wireless communication with ICD 14 for receiving cardiac electrical signals sensed by ICD 14. For example, cardiac monitor 60 may be coupled to an inductive antenna 33 that may be positioned over ICD 14, which may be implanted beneath the skin, to receive cardiac electrical signals sensed by ICD 14. The cardiac electrical signals may be received by cardiac monitor 60 from ICD 14 in real time via antenna 33. Cardiac monitor 60 may communicate with ICD 14 using other communication protocols, such as RF communication, whether that be proprietary or utilizing non-proprietary protocol (e.g., Bluetooth).

As described below in conjunction with FIGS. 4 and 5, ICD 14 includes cardiac electrical signal sensing circuitry which may be configured to sense multiple cardiac electrical signals simultaneously, each using a different sensing electrode vector selected from different combinations of the available electrodes 24, 26, 28, 30 and housing 15. However, due to processing and memory limitations of an implantable device, ICD 14 may have limited capacity for storing multiple cardiac electrical signals and/or limited capacity for storing signals sampled at relatively high sampling rates over several seconds or minutes. For example, ICD 14 may be configured to store up to 10, 20, 30, 40, 60, 100 or 120 seconds of at least two wideband filtered cardiac electrical signals sampled at a frequency of 128 Hz in its internal memory. These stored signals may be analyzed by ICD 14 or transmitted to external device 40 for post-processing and analysis for determining recommended or acceptable sensing control parameters according to the techniques disclosed herein. However, ICD 14 may be capable of sensing and transmitting more than two cardiac electrical signals in real time, e.g., three, four (or more) cardiac electrical signals sensed using three, four (or more) different sensing electrode vectors, and/or sensing and transmitting cardiac electrical signals at a relatively higher sampling rate, e.g., 256 Hz. Cardiac electrical signals sensed from more sensing electrode vectors and/or at relatively higher sampling rates than the storage capacity of ICD internal memory may be transmitted to an external device, e.g., external cardiac monitor 60 or external device 40, to enable analysis of a greater number of sensing electrode vectors.

The sensed cardiac electrical signals may be transmitted from ICD 14 to external device 40 in real time, for example during an office visit or a tachyarrhythmia induction procedure, to enable post-processing and analysis of multiple signals by processor 52 of external device 40. This analysis of real-time transmitted signals may be limited to cardiac signal episodes obtained during the office visit, e.g., during a tachyarrhythmia induction. In order to enable processing and analysis of cardiac electrical signals acquired during a spontaneous tachyarrhythmia episode detected by ICD 14, without the limitations posed by the storage capacity of ICD internal memory, ICD 14 may be configured to transmit real-time sensed cardiac electrical signals to external cardiac monitor 60, e.g., during ambulatory monitoring. External cardiac monitor 60 may be configured to receive cardiac electrical signals transmitted from ICD 14 via antenna 33, store the cardiac electrical signal data, e.g., in episodes of several seconds or minutes in duration, and transmit the data to external device 40 for post-processing and analysis according to the techniques disclosed herein. In this way, an external processor which may be included in cardiac monitor 60 or external device processor 52, is enabled to analyze a greater number of sensed cardiac electrical signals, determine a greater number of constructed cardiac electrical signals from the sensed signals, and/or process and analyze sensed cardiac signals acquired at a relatively higher sampling rate.

For example, instead of storing two cardiac electrical signals at a sampling rate of 128 Hz in ICD 14, which enables one additional cardiac electrical signal to be constructed from the two sensed signals, external cardiac monitor 60 may receive four cardiac electrical signals from ICD 14, sensed using four different sensing electrode vectors at a higher sampling rate of 256 Hz. The four sensed signals may be transmitted in real time to external cardiac monitor 60, e.g., during an implant procedure, during an office visit, during a tachyarrhythmia induction procedure or when ICD 14 is detecting a spontaneous ventricular tachyarrhythmia, allowing sensed cardiac signal data to be acquired and stored beyond the limits of ICD 14 memory capacity.

Processor 52 of external device 40 may receive episodes of the four cardiac electrical signals, which may correspond to induced or spontaneous tachyarrhythmia episodes, from external cardiac monitor 60 via communication link 35, which may be a wired or wireless communication link, e.g., using RF telemetry. Processor 52 of external device 40 may be configured to construct up to four additional cardiac electrical signals, corresponding to four sensing electrode vectors different from the four sensing electrode vectors used to sense the four sensed cardiac electrical signals such that all eight possible sensing electrode vectors selectable from electrodes 24, 26, 28, 30 and housing 15 may be analyzed for determining recommended sensing control parameters according to the techniques disclosed herein. As such, in some examples, external device processor 52 may receive the sensed cardiac electrical signals from ICD 14 via cardiac monitoring device 60. In other examples, a processor included in cardiac monitoring device 60 may receive the cardiac electrical signals sensed by ICD 14 via antenna 33 for processing and analysis by cardiac monitoring device 60. Recommended or acceptable sensing control parameters determined by the cardiac monitoring device 60 or external device 40 may be displayed to a user, e.g., in a user interface as described below in conjunction with FIGS. 11, 12 and 14-16.

Cardiac monitoring device 60 may be a wearable or portable monitoring device, such as a Holter monitor or mobile cardiac telemetry unit. Cardiac monitoring device 60 may optionally be coupled to surface or skin electrodes 31 for acquiring and storing or transmitting ECG signals to a remote patient monitoring database. It is to be understood, however, that ECG signal sensing by cardiac monitoring device 60 is optional in some examples. Cardiac monitoring device 60 may be configured to receive sensed cardiac electrical signals from ICD 14 without necessarily acquiring ECG signals from surface electrodes 31. As such cardiac monitoring device 60 may function as extended memory capacity of medical device system 10 for storing cardiac electrical signal data received from ICD 14 and as a relay device for transmitting the stored data received from ICD 14 to external device 40 or another computer for processing the received signals.

Cardiac monitoring device 60 may be configured to receive episodes of at least two cardiac electrical signals sensed by ICD 14 during one or more detected tachyarrhythmia episodes. The received cardiac signal episodes may be stored in memory of cardiac monitoring device 60 for later transmission to external device 40 via communication link 35, transmitted in real time to a remote patient monitoring computer or database for subsequent analysis or processed and analyzed by a processor included in cardiac monitoring device 60. Cardiac monitoring device 60 may be configured to receive cardiac electrical signals from ICD 14 that are sensed during multiple, different tachyarrhythmia episodes detected by ICD 14. In this way, the techniques disclosed herein for determining acceptable or recommended sensing control parameters for tachyarrhythmia detection by ICD 14 may be applied to a greater number of sensed signals and/or signals acquired at a higher sampling rate during one or more spontaneous tachyarrhythmia episodes.

Figure 2A:
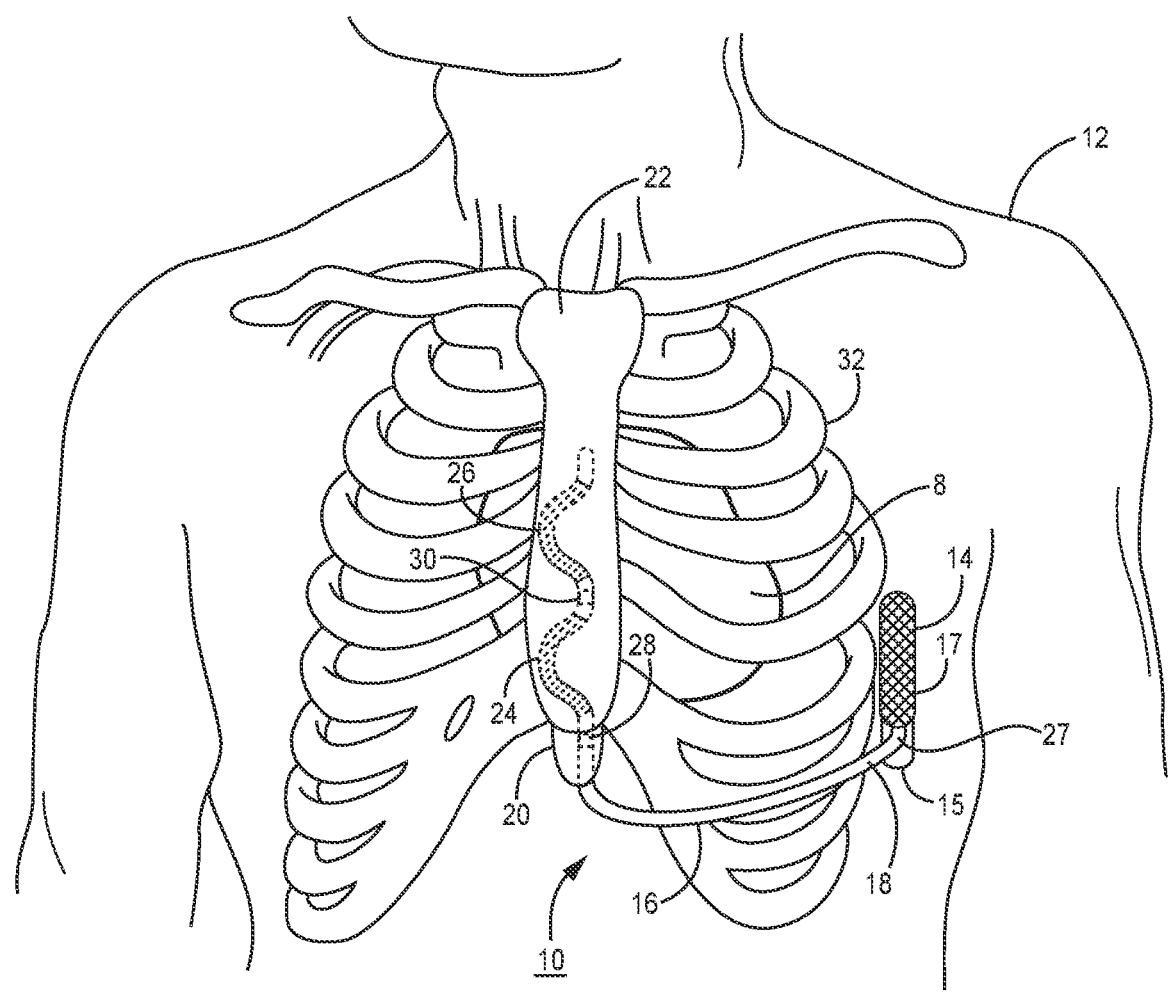
FIGS. 2A-2C are conceptual diagrams of a patient implanted with the medical device system of FIGS. 1A and 1B in a different implant configuration.
Figure 2B:
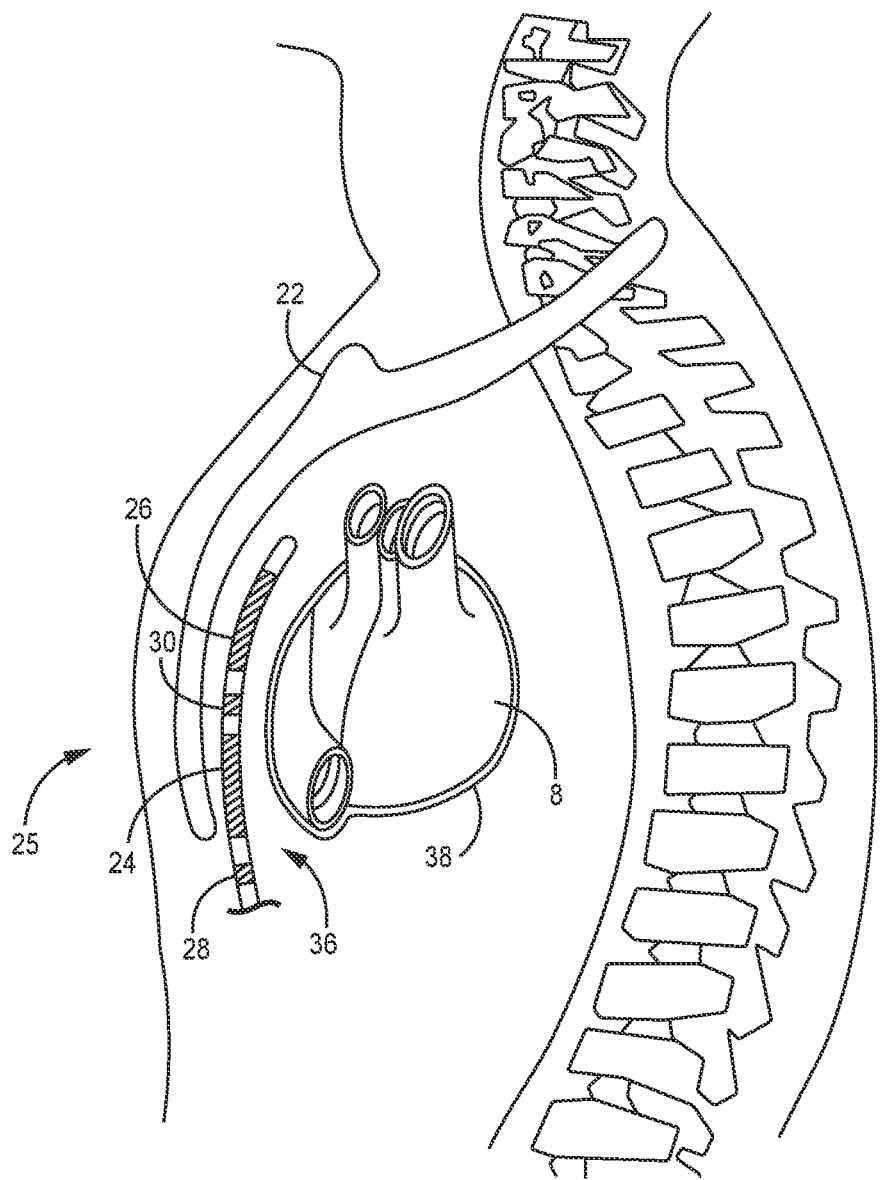
Figure 2C:
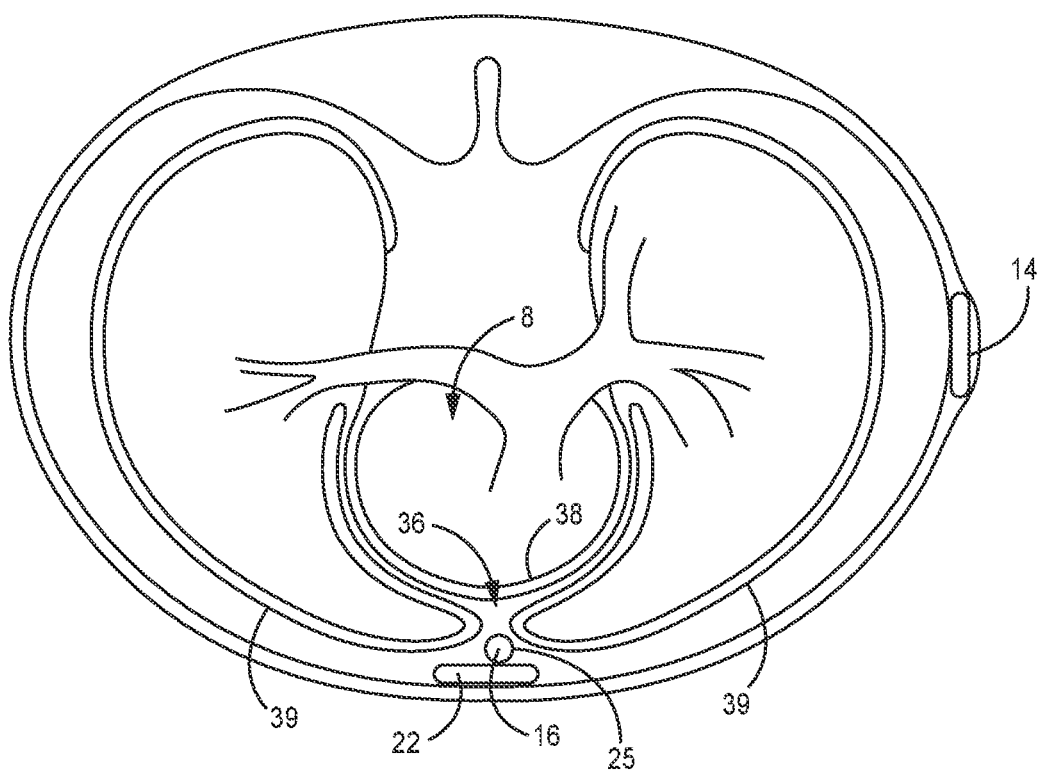

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, or within a pleural cavity or more generally within the thoracic cavity, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent or within the pericardium 38 of heart 8. In the examples described herein in conjunction with FIGS. 1A-2C, electrodes for sensing cardiac electrical signals are carried by a lead that may be advanced to a supra-diaphragmatic position, which may be within the thoracic cavity or outside the thorax in various examples.

Figure 3:
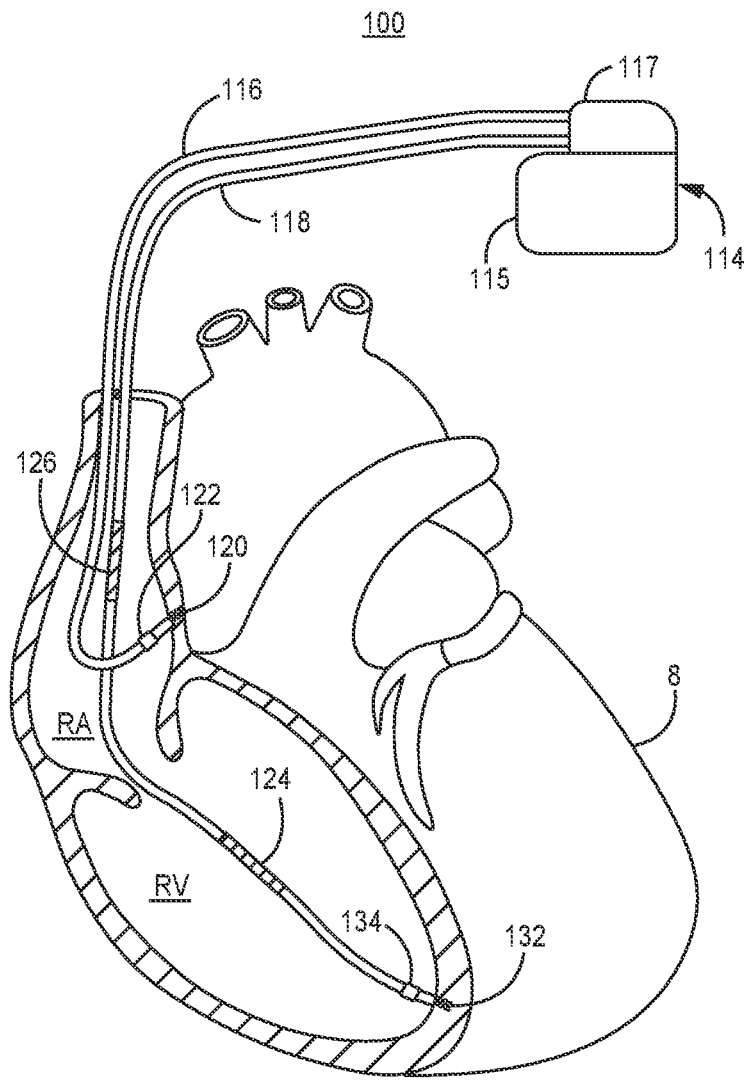
FIG. 3 is a conceptual diagram of a medical device system according to another example.

FIG. 3 is a conceptual diagram of a medical device system 100 that may be configured to perform techniques disclosed herein according to another example. System 100 includes ICD 114 coupled to transvenous leads 116 and 118 in communication with the right atrium (RA) and right ventricle (RV) of heart 8. ICD 114 includes a housing 115 enclosing circuitry, such as a processor, telemetry circuitry, sensing circuitry and therapy delivery circuitry as described below in conjunction with FIG. 4. ICD 114 includes connector assembly 117 having connector bores for receiving proximal connectors of RA lead 116 and RV lead 118 and providing electrical connection between electrodes carried by leads 116 and 118 and internal ICD circuitry.

RA lead 116 may carry a distal tip electrode 120 and ring electrode 122 for sensing atrial electrical signals and producing an atrial intra-cardiac electrogram (EGM) signal. RA electrodes 120 and 122 may be used for delivering RA pacing pulses. RV lead 118 may carry pacing and sensing electrodes 132 and 134 for sensing a ventricular electrical signal and producing an RV EGM signal. RV electrodes 132 and 134 may be used to deliver RV pacing pulses. RV lead 118 may also carry an RV defibrillation electrode 124 and a superior vena cava (SVC) defibrillation electrode 126. Defibrillation electrodes 124 and 126 are shown as coil electrodes spaced apart proximally from the distal pacing and sensing electrodes 132 and 134. While RA lead 116 and RV lead 118 are both shown advanced within a respective heart chamber, in some examples, a transvenous lead may be advanced to position electrodes within a venous location, outside the heart.

ICD 114 may be configured to provide dual chamber sensing and pacing therapies as well as high voltage CV/DF shock therapies in response to detecting VT or VF. In other examples, ICD 114 may be configured to provide multi-chamber sensing and pacing therapies, including cardiac resynchronization therapy (CRT), in which case a coronary sinus lead may be advanced along a cardiac vein to position electrodes for sensing and pacing the left ventricle of heart 8. In still other examples, ICD 114 may be a single chamber device coupled to a single lead, e.g., lead 116 or lead 118, for sensing cardiac electrical signals and delivery electrical stimulation therapies. ICD 114 may be configured to sense at least two cardiac electrical signals that may be processed and analyzed according to the techniques disclosed herein for determining acceptable sensing control parameters. A processor included in ICD 114 may perform the processing and analysis, or ICD 114 may transmit episodes of the two cardiac electrical signals to another device, e.g., external device 40 shown in FIG. 1A, for processing and analysis for determining recommended or acceptable sensing control parameters.

Figure 4:
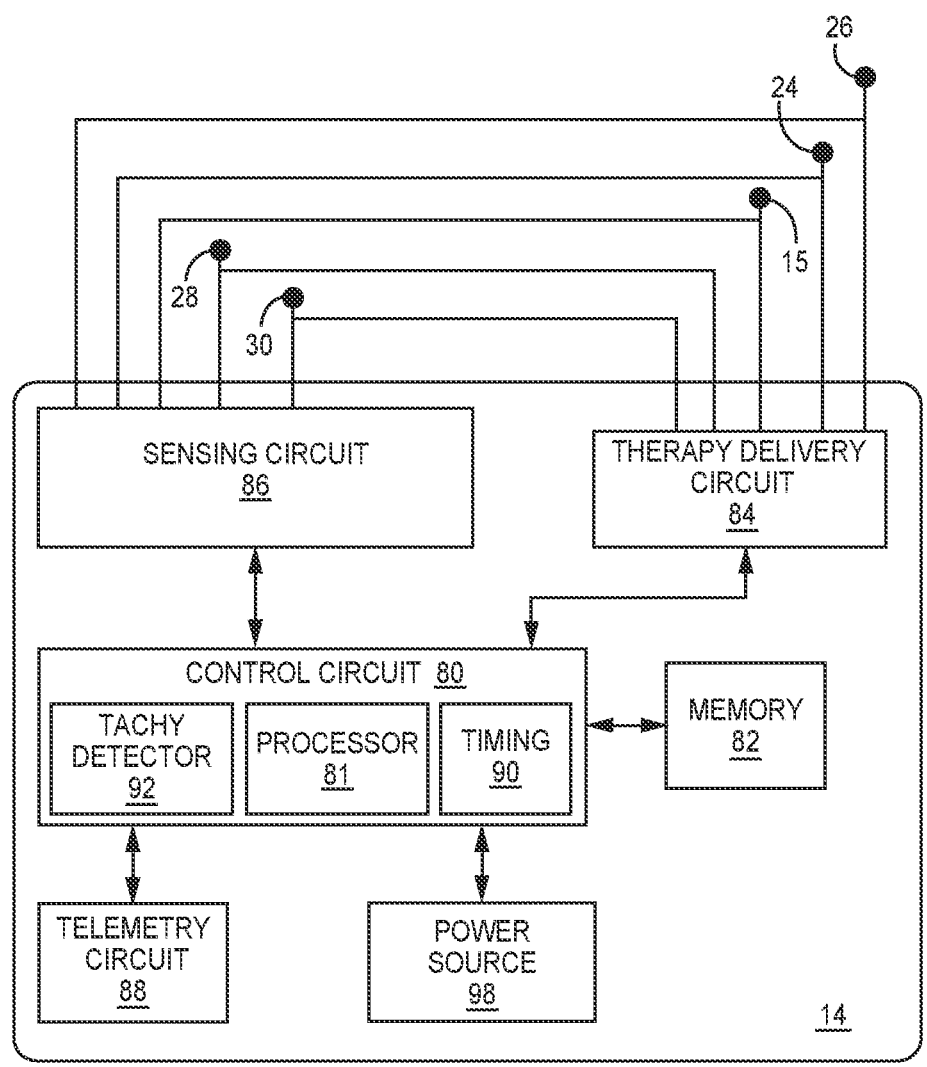
FIG. 4 is a conceptual diagram of a medical device configured to sense cardiac electrical signals according to one example.

FIG. 4 is a conceptual diagram of a medical device configured to sense cardiac electrical signals according to one example. FIG. 4 is described in conjunction with the ICD 14 of FIGS. 1A-2C, including therapy delivery capabilities. It is to be understood, however, the circuitry and functionality attributed to circuitry described in conjunction with FIG. 4 may be included, in whole or in part, in any of the example medical devices described or listed herein, such as the ICD 114 shown in FIG. 3. The ICD housing 15 is shown schematically as an electrode in FIG. 4 because the housing of the medical device may be used as an electrode in a sensing electrode vector for cardiac signal sensing and/or for therapy delivery in some examples. The electronic circuitry enclosed within housing 15 includes software, firmware and hardware that cooperatively monitor cardiac signals, determine when an electrical stimulation therapy is necessary, and deliver therapy as needed according to programmed therapy delivery algorithms and control parameters.

ICD 14 as shown in FIG. 4 includes a control circuit 80, memory 82, therapy delivery circuit 84, cardiac electrical signal sensing circuit 86, and telemetry circuit 88. Control circuit 80 communicates, e.g., via a data bus, with therapy delivery circuit 84 and sensing circuit 86 for sensing cardiac event signals, detecting cardiac rhythms, and controlling delivery of cardiac electrical stimulation therapies in response to sensed cardiac event signals. Therapy delivery circuit 84 and sensing circuit 86 are electrically coupled to electrodes 24, 26, 28, 30 and the housing 15, which may function as a common or ground electrode or as an active can electrode for delivering CV/DF shock pulses or cardiac pacing pulses. As described above electrodes 24, 26, 28 and 30 shown in FIG. 4 may be carried by a non-transvenous lead advanced to position electrodes in an extra-cardiac location (as shown in FIGS. 1A-2C) or by a transvenous lead for positioning electrodes within a blood vessel or an intracardiac location (e.g., electrodes 120, 122, 124, 126, 132, and 134 as shown in FIG. 3). Furthermore, electrodes coupled to the medical device may include multiple housing-based electrodes not carried by a lead in some examples.

A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4 but are not shown for the sake of clarity. For example, power source 98 may be coupled to one or more charging circuits included in therapy delivery circuit 84 for charging holding capacitors or other charge storage devices included in therapy delivery circuit 84 that are discharged at appropriate times under the control of control circuit 80 for producing electrical pulses according to a therapy protocol. In other examples, power source 98 may serve as a voltage or current source to therapy delivery circuit 84 without requiring a charge storage device. Power source 98 is also coupled to components of cardiac electrical signal sensing circuit 86, such as sense amplifiers, analog-to-digital converters, switching circuitry, etc., telemetry circuit 88 and memory 82 as needed.

The circuits shown in FIG. 4 represent functionality included in ICD 14 or another medical device operating according to the techniques disclosed herein and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing and determination of sensed cardiac event intervals may be performed cooperatively by sensing circuit 86 and control circuit 80 and may include operations implemented in a processor 81 or other signal processing circuitry included in control circuit 80 executing instructions stored in memory 82. Control signals such as blanking and timing intervals associated with setting the cardiac event sensing threshold amplitude may be sent from control circuit 80 to sensing circuit 86 according to programmed sensing control parameter settings.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the medical device system and by the particular detection and therapy delivery methodologies employed by the medical device system. Providing software, hardware, and/or firmware to accomplish the described functionality in the context of any modern medical device, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Cardiac electrical signal sensing circuit 86 (also referred to herein as "sensing circuit" 86) may be selectively coupled to electrodes 28, 30 and/or housing 15 in order to sense electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two different sensing electrode vectors from the available electrodes 24, 26, 28, 30, and housing 15 in some examples. Sensing circuit 86 may monitor one or more cardiac electrical signals for sensing cardiac events and/or producing digitized cardiac electrical signals passed to control circuit 80 for processing and analysis and/or for further transmission to external device 40 via telemetry circuit 88. For example, sensing circuit 86 may include switching circuitry for selecting which of electrodes 24, 26, 28, 30, and housing 15 are coupled to one or more sensing channels of sensing circuit 86.

As described below in conjunction with FIG. 5, sensing circuit 86 may be configured to amplify, filter, rectify and digitize or otherwise process the cardiac electrical signal received from each selected sensing electrode vector to improve the signal quality for sensing cardiac electrical events, such as R-waves or P-waves. Cardiac event detection circuitry included within sensing circuit 86 may include one or more sense amplifiers, filters, rectifiers, threshold detectors, comparators, analog-to-digital converters (ADCs), timers or other analog or digital components configured to sense cardiac events, e.g., R-waves attendant to ventricular depolarizations and P-waves attendant to atrial depolarizations from a sensed cardiac electrical signal received by sensing circuit 86 via the selected sensing electrode vector.

Sensing circuit 86 may control the amplitude of an auto-adjusting cardiac event sensing threshold over each cardiac cycle, e.g., as described below in conjunction with FIG. 6. Sensing circuit 86 may sense a cardiac event in response to a cardiac electrical signal crossing the sensing threshold. Sensing circuit 86 may produce a cardiac sensed event signal, e.g., an atrial sensed event signal in response to a P-wave sensing threshold crossing or a ventricular sensed event signal in response to an R-wave sensing threshold crossing. The cardiac sensed event signals are passed to control circuit 80. As described below, various sensing threshold control parameters may be used by sensing circuit 86 to set and adjust the cardiac event sensing threshold during each cardiac cycle. These sensing threshold control parameters may be stored in memory 82 and passed to sensing circuit 86 from control circuit 80 for use by hardware, firmware and/or software of control circuit 80 and/or sensing circuit 86 in controlling the amplitude of the cardiac event sensing threshold.

Control circuit 80 receives the cardiac sensed event signals from sensing circuit 86 for determining sensed cardiac event intervals, e.g., RR intervals (RRIs) and/or PP intervals (PPIs), by timing circuit 90. An RRI is the time interval between two consecutively sensed R-waves and may be determined between consecutive ventricular sensed event signals received by control circuit 80 from sensing circuit 86. A PPI is the time interval between two consecutively sensed P-waves and may be determined between consecutive atrial sensed event signals received by control circuit 80 from sensing circuit 86. Depending on programmed therapies, timing circuit 90 may trigger therapy delivery circuit 84 to generate and deliver an electrical stimulation pulse in response to a sensed event signal and/or start a pacing escape interval timer in response to a sensed event signal and restart the escape interval timer in response to the next sensed event signal. The value of the escape interval timer at the time of the next sensed event signal may be buffered in memory 82 as the sensed cardiac event interval for the associated sensed event signal. In this way, memory 82 may store a series of sensed cardiac event intervals for determining a sensed cardiac event rate.

Timing circuit 90 may include various timers and/or counters used to control the timing of therapy delivery by therapy delivery circuit 84. In response to expiration of an escape interval timer without receiving a cardiac sensed event signal, control circuit 80 may control therapy delivery circuit 84 to generate and deliver a pacing pulse. Timing circuit 90 may additionally set time windows such as morphology template windows, morphology analysis windows or perform other timing related functions of ICD 14 including synchronizing CV/DF shocks or other therapies delivered by therapy delivery circuit 84 with sensed cardiac events.

Control circuit 80 may include a tachyarrhythmia detector 92 configured to analyze signals received from sensing circuit 86 for detecting tachyarrhythmia. Tachyarrhythmia detector 92 may detect tachyarrhythmia based on cardiac events sensed by sensing circuit 86 meeting tachyarrhythmia detection criteria, such as a threshold number of sensed cardiac events occurring at cardiac event intervals falling in a tachyarrhythmia interval range. Tachyarrhythmia detector 92 may be implemented in control circuit 80 as hardware, software and/or firmware that processes and analyzes signals received from sensing circuit 86 for detecting tachyarrhythmia, e.g., supraventricular tachycardia (SVT), VT and/or VF. Tachyarrhythmia detector 92 may include comparators and counters for counting cardiac event intervals, e.g., PPIs or RRIs determined by timing circuit 90, that fall into various rate detection zones for determining an atrial rate and/or a ventricular rate or performing other rate- or interval-based assessment of cardiac sensed event signals for detecting and discriminating tachyarrhythmias.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. The VF detection interval threshold may be set to 300 to 350 milliseconds (ms), as an example. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. RRIs that are less than the VT detection interval but greater than the VF detection interval may be counted by a VT interval counter. In order to detect VT or VF, the respective VT or VF interval counter is required to reach a threshold "number of intervals to detect" or "NID."

As an example, the NID to detect VT may require that the VT interval counter reaches 18 VT intervals, 24 VT intervals, 32 VT intervals or other selected NID. In some examples, the VT intervals may be required to be consecutive intervals, e.g., 18 out of 18, 24 out of 24, or 32 out of the most recent 32 consecutive RRIs. The NID required to detect VF may be programmed to a threshold number of X VF intervals out of Y consecutive RRIs. For instance, the NID required to detect VF may be 18 VF intervals out of the most recent 24 consecutive RRIs or 30 VF intervals out 40 consecutive RRIs, as examples. When a VT or VF interval counter reaches an NID, a ventricular tachyarrhythmia may be detected by tachyarrhythmia detector 92. The NID may be programmable and range from as low as 12 to as high as 40, with no limitation intended. VT or VF intervals may be detected consecutively or non-consecutively out of a specified number of most recent RRIs. In some cases, a combined VT/VF interval counter may count both VT and VF intervals and detect a tachyarrhythmia episode based on the fastest intervals detected when a specified NID is reached.

Tachyarrhythmia detector 92 may be configured to perform other signal analysis for determining if other detection criteria are satisfied before detecting VT or VF, such as R-wave morphology criteria and onset criteria. To support additional cardiac signal analyses, sensing circuit 86 may pass a digitized cardiac electrical signal to control circuit 80, e.g., an ECG signal when sensed using electrodes outside the heart or an EGM signal when sensed using intracardiac electrodes. The digitized cardiac electrical signal may be passed to control circuit 80 for morphology analysis performed by tachyarrhythmia detector 92 for detecting and discriminating heart rhythms. A cardiac electrical signal from a selected sensing electrode vector may be passed through a filter and amplifier, provided to a multiplexer and thereafter converted to a multi-bit digital signal by an analog-to-digital converter, all included in sensing circuit 86, for storage in memory 82 and/or for real time transmission via telemetry circuit 88. Memory 82 may include one or more circulating buffers to temporarily store digital cardiac electrical signal segments (also referred to herein as "episodes") for analysis performed by control circuit 80 and/or by external device processor 52 after transmission via telemetry circuit 88. Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac electrical signals and cardiac event waveforms, e.g., R-waves.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF therapy. Therapy can be generated by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses. In other examples, therapy delivery circuit 84 may include a low voltage therapy circuit for generating and delivering pacing pulses for a variety of pacing needs.

It is recognized that the methods disclosed herein for processing and analyzing cardiac electrical signals may be implemented in a medical device system that is used for monitoring cardiac electrical signals by sensing circuit 86 and control circuit 80 without necessarily having therapy delivery capabilities or in a pacemaker that monitors cardiac electrical signals and delivers cardiac pacing therapies by therapy delivery circuit 84, without high voltage therapy capabilities such as CV/DF shock capabilities.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. Telemetry circuit 88 may transmit sensed cardiac electrical signals (and in some cases sensed cardiac event markers and associated cardiac event intervals) to another medical device, e.g., external device 40, for processing and analysis according to the techniques disclosed herein. In other examples, control circuit 80 may be configured to perform some or all of the analysis of cardiac electrical signals as disclosed herein and may transmit the data resulting from the analysis to external device 40.

Figure 5:
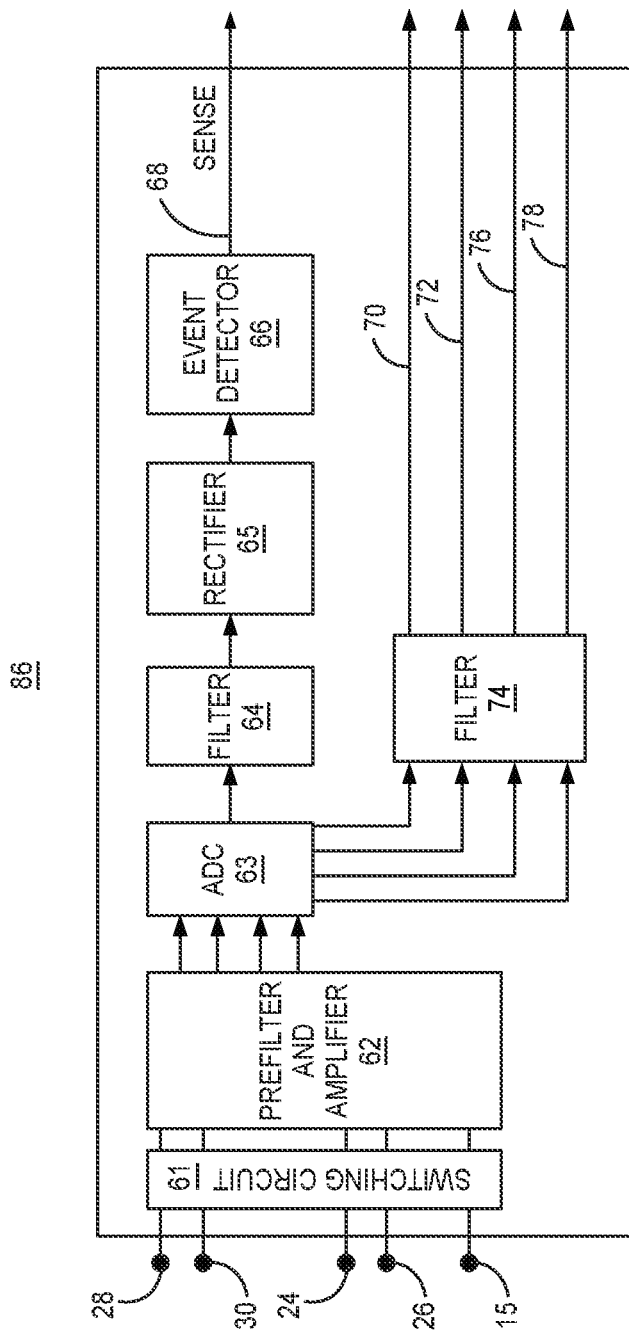
FIG. 5 is a conceptual diagram of circuitry that may be included in the sensing circuit shown in FIG. 4 according to one example.

FIG. 5 is a conceptual diagram of circuitry that may be included in sensing circuit 86 of a medical device, e.g., ICD 14, according to one example. Sensing circuit 86 may be coupled to all available electrodes that may be used in a sensing electrode vector for sensing cardiac electrical signals. Using the example medical device system 10 of FIGS. 1A-2C, sensing circuit 86 is shown coupled to pace/sense electrodes 28 and 30, defibrillation electrodes 24 and 26 and housing 15, which may be selected in any combination as a sensing electrode vector. Sensing circuit 86 may include switching circuit 61 for controlling which electrodes are selected in a pair as a sensing electrode vector that is coupled to prefilter and amplifier 62. Two or more sensing electrode vectors may be coupled to prefilter and amplifier 62. In one example, the two pace/sense electrodes 28 and 30 carried by lead 16 are selected as one sensing electrode vector, and one pace/sense electrode 28 or 30 carried by lead 16 is selected in combination with housing 15 as a second sensing electrode vector. A sensing electrode vector may be selected by switching circuit 61 according to control signals from control circuit 80. Switching circuit 61 may include a switch array, switch matrix, multiplexer, or any other type of switching device(s) suitable to selectively couple selected electrodes to the input prefilter and amplifier 62.

Each electrical signal developed across the selected sensing electrode vectors, e.g., electrodes 28 and 30 in a first sensing electrode vector and electrode 30 and housing 15 in a second sensing electrode vector, is received as a differential input signal by the pre-filter and pre-amplifier 62. Non-physiological high frequency and DC signals may be filtered by a low pass or bandpass filter included in pre-filter and pre-amplifiers 62, and high voltage signals may be removed by protection diodes included in pre-filter and pre-amplifiers 62. Pre-filter and pre-amplifier 62 may amplify the pre-filtered signal by a gain of between 10 and 100, and in one example a gain of 17.5, and may convert the differential signal to a single-ended output signal passed to analog-to-digital converter (ADC) 63. Pre-filter and amplifier 62 may provide anti-alias filtering and noise reduction prior to digitization.

ADC 63 converts the cardiac electrical signal from an analog signal to a digital bit stream. In one example, ADC 63 may be a sigma-delta converter (SDC), but other types of ADCs may be used. In some examples, the output of ADC 63 may be provided to a decimator (not shown), which functions as digital low-pass filter that increases the resolution and reduces the sampling rate of the cardiac electrical signal. The digital output of ADC 63 may be passed to a digital bandpass filter 64 and on to cardiac event detector 66 for sensing cardiac events. Filter 64 may have a relatively narrow bandpass of approximately 13 Hz to 39 Hz for passing cardiac event signals, such as R-waves, typically occurring in this (or other bandpass) frequency range. The narrowband filtered signal may be passed from filter 64 to rectifier 65 to produce a filtered, rectified signal that is received by a cardiac event detector 66 for sensing cardiac events in response to the narrowband filtered and rectified signal crossing a cardiac event sensing threshold amplitude, for example an R-wave sensing threshold amplitude. In some examples, cardiac event detector 66 may include a P-wave detector for producing atrial sensed event signals in response to a P-wave sensing threshold.

Cardiac event detector 66 may include an auto-adjusting sense amplifier, comparator and/or other detection circuitry that compares the filtered and rectified cardiac electrical signal to a cardiac event sensing threshold amplitude and produces a sensed event signal 68, which may be a ventricular sensed event signal or an atrial sensed event signal, when the filtered, rectified signal crosses the cardiac event sensing threshold outside of any blanking periods applied by sensing circuit 86. A cardiac event sensing threshold applied by cardiac event detector 66 may be a multi-level sensing threshold, for example as described below in conjunction with FIG. 6. Multiple sensing threshold control parameters may be used to adjust the amplitude of the cardiac event sensing threshold starting from the expiration of a post-sense (or post-pace) blanking period until the next cardiac event sensing threshold crossing (or expiration of a pacing interval). The techniques described herein are not limited to a specific behavior of the sensing threshold amplitude and numerous cardiac event sensing threshold control parameters, as described below in conjunction with FIG. 6, may be defined and used to control the cardiac event sensing threshold amplitude over a cardiac cycle, until a cardiac event is sensed or a pacing escape interval expires resulting in a pacing pulse.

In some examples, event detector 66 includes a peak detector, which may include a sample and hold circuit, for detecting the maximum peak amplitude of the rectified signal following a cardiac sensed event signal produced by cardiac event detector 66. The maximum peak amplitude may be used by cardiac event detector 66 for setting the starting amplitude of the cardiac event sensing threshold based on the detected maximum peak amplitude. The starting cardiac event sensing threshold amplitude may be set by cardiac event detector 66 upon expiration of any post-sense blanking period applied upon detecting a sensing threshold crossing. The cardiac event sensing threshold amplitude may be set to a starting amplitude that is a percentage of the maximum peak amplitude, e.g., 60%, 70%, 80% or other selected percentage. The starting sensing threshold amplitude may be adjusted according to the sensing threshold control parameters down to a sensing floor, which may be equal to the programmed sensitivity, or until a sensing threshold crossing, whichever occurs first. The sensitivity is the lowest amplitude that the cardiac event sensing threshold may be adjusted to and is therefore the lowest amplitude of the cardiac electrical signal that may be sensed as a cardiac event. The lower the programmed value of the sensitivity, e.g., 0.03 millivolts or less, the more sensitive sensing circuit 86 is to sensing cardiac events. Sensing circuit 86 is relatively less sensitive to sensing cardiac events when the programmed value of the sensitivity is relatively higher, e.g., 0.9 millivolts or higher.

Sensing circuit 86 may include wideband filter 74 for producing a cardiac EGM (sensed by intracardiac electrodes) or ECG (sensed by extra-cardiac electrodes) signal that is passed to control circuit 80, e.g., signal 78, for performing morphological analysis of the cardiac signal waveforms. For example, control circuit 80 may perform morphology analysis of the wideband filtered cardiac electrical signal 78 to detect and distinguish R-waves arising from non-sinus tachycardia or fibrillation waves from normally conducted R-waves. Wideband filter 74 may have a bandpass of approximately 2.5 to 100 Hz. In some examples, filter 74 may include a notch filter to attenuate 60 Hz or 50 Hz line noise. The cardiac electrical signal received by the sensing electrode vector between one of pace/sense electrodes 28 or 30 and housing 15 may be passed from ADC 63 to wideband filter 74 for morphological analysis by control circuit 80 for use in tachyarrhythmia detection. A second cardiac electrical signal received by a different sensing electrode vector, e.g., between pace/sense electrodes 28 and 30, may be passed to narrowband filter 64 and to wideband filter 74. Both the first and the second wideband filtered cardiac electrical signals may be analyzed for determining acceptable or recommended sensing control parameters by control circuit 80 or by the processor of another medical device, e.g., external device processor 52 (FIG. 1A).

Sensing circuit 86 may be configured to select one sensing electrode vector out of multiple available sensing electrode vectors for cardiac event sensing by event detector 66. The sensing electrode vector may be a programmable sensing control parameter. For the sake of illustration, sensing circuit 86 may select one sensing electrode vector from among three different sensing electrode vectors for sensing cardiac events. The three different sensing electrode vectors may be between pace/sense electrodes 28 and 30, between pace/sense electrode 28 and housing 15, and between pace/sense electrode 30 and housing 15 in one example.

Sensing circuit 86 may be configured to select two or more sensing electrode vector signals for passing to wideband filter 74. In some examples, a single wideband filtered signal is used by control circuit 80 for morphological analysis, e.g., for tachyarrhythmia detection. However, multiple wideband filtered vector signals may be analyzed according to the techniques disclosed herein for determining acceptable or recommended sensing control parameters. For the sake of illustration, sensing circuit 86 may be configured to select up to four sensing electrode vectors for producing four different wideband filtered digital cardiac electrical signals 70, 72, 76 and 78 from among ten possible sensing electrode vector signals available from the four electrodes 24, 26, 28, 30 and housing 15. In the example shown, the ten possible sensing electrode vectors are between pace/sense electrodes 28 and 30, between pace/sense electrode 28 and each of housing 15, defibrillation electrode 24 and defibrillation electrode 26, between pace/sense electrode 30 and each of housing 15, defibrillation electrode 24 and defibrillation electrode 26, between defibrillation electrodes 24 and 26, between defibrillation electrode 24 and housing 15, and between defibrillation electrode 26 and housing 15.

All four wideband filtered sensing vectors signals 70, 72, 76 and 78 may be analyzed according to techniques disclosed herein for determining acceptable or recommended sensing control parameters. In one example, the wideband filtered signals 70, 72, 76 and 78 are sampled at 256 Hz and transmitted by telemetry circuit 88 in real time. The transmitted cardiac electrical signals may be received by another device, e.g., external device 40, for processing and analysis. In other examples, the wideband filtered signals 70, 72, 74, and/or 76 may be stored in memory 82 for post-processing and analysis by control circuit 80 or for later transmission via telemetry circuit 88. Because memory 82 may have limited capacity for storing cardiac electrical signals, fewer signals and/or signals sampled at a lower sampling rate may be stored in memory 82 for later analysis or transmission than the number and/or sampling rate of cardiac electrical signals that may be transmitted to external device 40 in real time for subsequent analysis and processing. For example, two wideband filtered signals sampled at a frequency of 128 Hz may be stored in memory 82 for post-processing and analysis, which may include transmission to another device for performing the post-processing and analysis.

A user interacting with external device 40 may select the sensing electrode vector signals that are passed to wideband filter 74 for storage in memory 82 or real time transmission. In illustrative examples presented herein, at least two sensing electrode vector signals are selected for wideband filtering for real time transmission or storage in memory 82. The two sensing electrode vectors include one electrode common to both sensing electrode vectors such that a third cardiac electrical signal that would be sensed using a third sensing electrode vector between the two electrodes that are unique to the two selected sensing electrode vectors can be constructed. In this way by sensing two cardiac electrical signals, three cardiac electrical signals corresponding to three different sensing electrode vectors are available for processing and analysis for determining acceptable or recommended sensing control parameters. In the illustrative examples presented herein, the two sensed cardiac electrical signal correspond to a first sensing electrode vector between pace/sense electrodes 28 and 30 and second sensing electrode vector between pace/sense electrode 30 and housing 15. During processing and analysis, control circuit 80 or another processor, e.g., external device processor 52 (FIG. 1A), may construct a third cardiac electrical signal that is expected to be sensed between the two electrodes that are not common to the sensed cardiac electrical signal sensing vectors, which would be between pace/sense electrode 28 and housing 15 in the illustrative example given here.

By programming selected sensing electrode vector signals for filtering by wideband filter 74, one or more additional sensing electrode vectors signals may be constructed by a processor, thereby enabling analysis of multiple sensed and constructed cardiac electrical signals for determining acceptable or recommended sensing control parameters, which may include an acceptable or recommended the sensing electrode vector. The techniques disclosed herein for determining acceptable or recommended sensing control parameters, therefore, do not require all cardiac electrical signals that undergo analysis to be sensed cardiac electrical signals. The number of sensing electrode vector signals available for analysis can be increased by constructing one or more cardiac electrical signals from the sensed cardiac electrical signals. When four different cardiac electrical signals are sensed, e.g., using all four available electrodes 24, 26, 28 and 30 each paired with housing 15 in four different sensing electrode vectors all having one common electrode (housing 15 in this example), the remaining six possible sensing electrode vector signals may be constructed from the four sensed cardiac electrical signals. Furthermore, in some examples, a cardiac electrical signal may be constructed from one sensed and one constructed cardiac electrical signal determined from two other cardiac electrical signals or even constructed from two other constructed cardiac electrical signals.

In some examples, sensing circuit 86 may include two or more sensing channels including the same or different filters, amplifiers, ADCs and/or other signal processing circuitry such that different cardiac electrical signals sensed from one or different sensing electrode vectors may be passed to control circuit 80 for processing and analysis. While sensing circuit 86 is shown having a single prefilter and amplifier 62, ADC 63 and wideband filter 74 for passing up to four sensed cardiac electrical signals 70, 72, 76 and 78, other sensing circuit configurations may include multiple channels, each having its own prefilter and amplifier, ADC and wideband filter for passing a cardiac electrical signal to control circuit 80 for storage in memory 82 and/or transmission by telemetry circuit 88. An example sensing circuit having two sensing channels each with a prefilter and preamplifier and ADC is generally described in U.S. Pat. No. 9,956,423 (Zhang, et al.), incorporated herein by reference in its entirety. Sensing circuit 86 may include more or fewer components than illustrated in FIG. 5 and some components may be shared between multiple sensing channels for sensing multiple cardiac electrical signals. The configuration of sensing circuit 86 as shown in FIG. 5 is therefore illustrative in nature and should not be considered limiting of the techniques described herein for sensing at least two cardiac electrical signals and constructing at least one more cardiac electrical signal. As described below, each sensed cardiac electrical and/or each cardiac electrical signal constructed from the sensed cardiac electrical signals may be analyzed according to multiple sensing threshold control parameter settings. In the illustrative examples disclosed herein, the sensed cardiac electrical signals sensed by sensing circuit 86 may be transmitted to external device 40 for post-processing and analysis for constructing at least one more cardiac electrical signal and/or determining sensed cardiac event intervals according to multiple sensing threshold control parameter settings.

Figure 6:
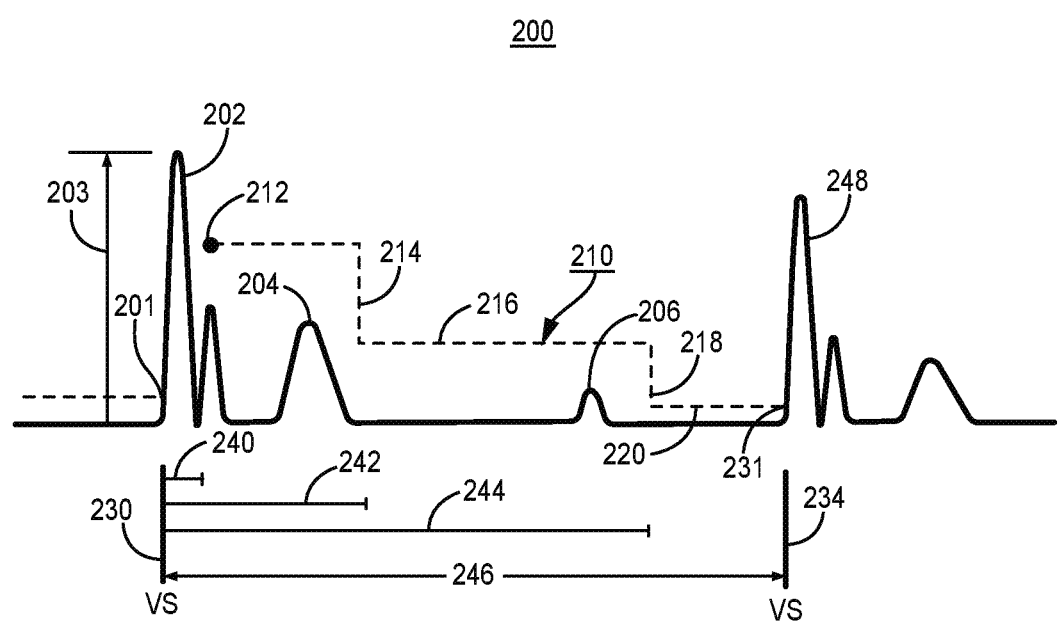
FIG. 6 is a diagram of a filtered and rectified cardiac electrical signal illustrating one technique for adjusting a cardiac event sensing threshold.

FIG. 6 is a diagram of a filtered and rectified cardiac electrical signal 200 illustrating one technique for adjusting the cardiac event sensing threshold 210 by sensing circuit 86 under the control of control circuit 80. Cardiac electrical signal 200 includes an R-wave 202, a T-wave 204, and a P-wave 206. The cardiac electrical signal 200 may be representative of the output of rectifier 65 received by cardiac event detector 66 as shown in FIG. 5. Alternatively, cardiac electrical signal 200 may represent a narrowband filtered and rectified signal determined from a sensed or constructed wideband filtered signal by control circuit 80 or external device processor 52 during processing and analysis of the sensed and constructed cardiac electrical signals for determining sensed cardiac events according to one or more cardiac event sensing threshold control parameter settings. Analysis performed by a processor as disclosed herein to determine sensed cardiac events according to test sensing control parameter settings mimics the processing that occurs by sensing circuit 86 for sensing cardiac events from the narrowband filtered, rectified signal by cardiac event detector 66. In the description that follows, the operations performed to adjust the cardiac event sensing threshold 210 are described as being performed by sensing circuit 86 for the sake of convenience. However, during real time or post-processing of a cardiac electrical signal by control circuit 80, by external device processor 52 or by another processor, it is to be understood that determination of sensed cardiac events from the cardiac electrical signal involves the same cardiac event sensing threshold adjustment operations as would be performed by sensing circuit 86 for determining when the cardiac electrical signal, sensed or constructed, is estimated to cross the cardiac event sensing threshold.

In this example, the cardiac event sensing threshold 210 is an R-wave sensing threshold that is adjusted for sensing R-waves from the cardiac electrical signal 200 and determining RRIs. Sensing circuit 86 adjusts the R-wave sensing threshold 210 between a starting threshold amplitude 212 and the minimum sensing threshold amplitude equal to the programmed sensitivity 220. The starting threshold amplitude 212 may be set based on the maximum peak amplitude 203 of sensed R-wave 202. R-wave 202 is sensed by sensing circuit 86 in response to the cardiac electrical signal 200 crossing the R-wave sensing threshold at 201. Sensing circuit 86 produces a ventricular sensed event signal (VS) 230 (e.g., corresponding to the sensed event signal 68 output by cardiac event detector 66 shown in FIG. 5) in response to the sensing threshold crossing 201. Sensing circuit 86 may be configured to detect the maximum peak of R-wave 202 during a post-sense blanking period 240 for determining maximum peak amplitude 203. The starting R-wave sensing threshold amplitude 212 may be set to a percentage, e.g., between 55% and 70% or another selected percentage, of the maximum peak amplitude 203. For example, the percentage used to set starting R-wave sensing threshold amplitude 212 can be 62.5% of the maximum peak amplitude 203.

The starting threshold 212 may be held for a sense delay interval 242 to avoid oversensing T-wave 204 as an R-wave. In other examples, the starting threshold 212 may decay at a specified decay rate for a predetermined decay interval. In the example shown, R-wave sensing threshold 210 is decreased by a step decrement 214 upon expiration of sense delay interval 242. Sense delay interval 242 may be between 300 and 400 ms, as examples, and is 360 ms in one example. At the expiration of sense delay interval 242, sensing circuit 86 adjusts the R-wave sensing threshold 210 from the starting amplitude 212 set to a first percentage of maximum peak amplitude 203 to an intermediate sensing threshold amplitude 216 that is a second percentage of R-wave maximum peak amplitude 203. The second percentage is less than the first percentage. Intermediate sensing threshold amplitude 216 may be set to between 25% and 60% of the maximum peak amplitude 203 or between 30% and 35% of the maximum peak amplitude 203 as examples. Intermediate sensing threshold amplitude 216 is less than the starting sensing threshold amplitude 212 by step decrement 214.

R-wave sensing threshold 210 may be held at the intermediate amplitude 216 for a drop time interval 244 as shown in FIG. 6. In other examples, R-wave sensing threshold 210 may decay at a specified decay rate from the expiration of the sense delay interval 242 until the expiration of drop time interval 244 or until reaching the sensing floor equal to the programmed sensitivity 220. In the example shown, upon expiration of drop time interval 244, sensing circuit 86 adjusts R-wave sensing threshold 210 from the intermediate sensing threshold amplitude 216 to the sensitivity 220 in a step decrement 218. The sensitivity 220 defines the minimum sensing threshold amplitude or sensing floor of R-wave sensing threshold 210. The drop time interval 244 may be between 1 second and 2 seconds and is 1.5 seconds in one example. The sensitivity 220 may be programmable over a range of 0.075 millivolts (mV) to 1.2 mV, as examples, though lower or higher sensitivity settings may be available.

Each of the first percentage used to set starting sensing threshold amplitude 212 as a percentage of maximum peak amplitude 203, the second percentage used to set intermediate sensing threshold amplitude 216 as a percentage of maximum peak amplitude 203, the sensitivity 220, the post-sense blanking period 240, the sense delay interval 242 and the drop time interval 244 may be programmable or adjustable cardiac event sensing threshold control parameters. Accordingly, processor 52 of external device 40 (and/or control circuit 80) may be configured to determine cardiac sensed events from one or more cardiac electrical signals, sensed and/or constructed, according to one or more different settings of one cardiac event sensing threshold control parameter or combinations of different settings of two or more different sensing threshold control parameters. In illustrative examples described below, programmer 52 of external device 40 is configured to at least determine sensed cardiac events according to different settings of sensitivity 220 for at least one constructed cardiac electrical signal.

As shown in FIG. 6, R-wave sensing threshold 210 is held at sensitivity 220 until the cardiac electrical signal 200 crosses the sensing threshold 210, at sensing threshold crossing 231, resulting in the next VS event signal 234 produced by sensing circuit 86. It is to be understood that the cardiac electrical signal 200 may not cross the sensing threshold 210 before a pacing interval expires during some cardiac cycles. In this case, therapy delivery circuit 84 may generate and deliver a pacing pulse. At other times, the next R-wave 248 may occur earlier after R-wave 202, before R-wave sensing threshold 210 reaches sensitivity 220 (before drop time interval 244 expires) or even before R-wave sensing threshold 210 reaches the intermediate sensing threshold amplitude 216 (before sense delay interval 242 expires). The cardiac event interval 246, which is an RRI in this example, may be determined by control circuit 80 (or processor 52 of external device 40) as the time interval between VS event signal 230 corresponding to threshold crossing 201 and VS event signal 234 corresponding to threshold crossing 234.

The particular behavior of R-wave sensing threshold 210 shown in FIG. 6 as it is adjusted between the starting threshold amplitude 212, set based on the maximum peak amplitude 203, and the sensitivity 220 is one illustrative example of how sensing circuit 86 may adjust the sensing threshold 210. It is to be understood that a variety of cardiac event sensing threshold control parameters, e.g., R-wave sensing threshold control parameters for ventricular rate determination or P-wave sensing threshold control parameters for atrial rate determination, may include one or more decay rates, each associated with a decay interval, and/or one or more step decrements, each associated with a drop time interval. Various cardiac event sensing threshold control parameters may be used by sensing circuit 86 for adjusting the R-wave sensing threshold 210 between the starting threshold 212 and sensitivity 220. For example, the R-wave sensing threshold 210 may decay, linearly or non-linearly, from starting sensing threshold amplitude 212 to sensitivity 220 at a predetermined decay rate until a sensing threshold crossing or a pacing interval expires, whichever occurs first.

The techniques disclosed herein for determining sensed cardiac events from one or more cardiac electrical signals (corresponding to different sensing electrode vectors) according to one or more sensing threshold control parameter settings are not limited to use with any particular sensing threshold control parameters or sensing threshold adjustment schemes. The cardiac event sensing threshold control parameters used by sensing circuit 86 to adjust sensing threshold 210, however, are the same cardiac event sensing threshold control parameters used by control circuit 80 and/or external device processor 52 for determining sensed cardiac events during post processing of different cardiac electrical signals for determining a recommended sensing control parameter setting. While the same sensing control parameters are used, such as sense delay interval 242, drop time interval 244 and sensitivity 220, different settings of these sensing threshold control parameters may be used during a determination of sensed cardiac events from a sensed or constructed cardiac electrical signal. By simulating the adjustment of the cardiac event sensing threshold that is performed by sensing circuit 86 during real time cardiac event sensing, control circuit 80 or external device processor 52 can determine sensed cardiac events for multiple different combinations of sensing control parameters settings without requiring ICD 14 to be reprogrammed to the multiple different combinations and perform the real time sensing.

Figure 7:
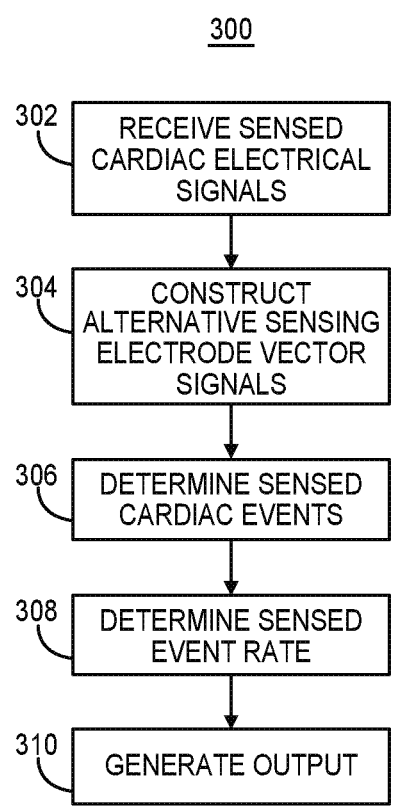
FIG. 7 is a flow chart of a method that may be performed by a medical device for determining a recommended setting of a sensing control parameter based on an analysis of multiple sensing electrode vector signals.

FIG. 7 is a flow chart 300 of a method that may be performed by a medical device for determining sensed cardiac events according to multiple sensing control parameters according to one example. At block 302, sensed cardiac electrical signals are received by a processor of a device performing the cardiac electrical signal analysis. As indicated above, the process for analyzing cardiac electrical signals as disclosed herein may be performed by a medical device that senses the cardiac electrical signals, e.g., by control circuit 80 of ICD 14 or processing circuitry of a pacemaker, cardiac monitor or other device configured to sense the cardiac electrical signals. As such, in one example, control circuit 80 receives at least two sensed cardiac electrical signals from sensing circuit 86 at block 302.

In other examples, the process for analyzing cardiac electrical signals as disclosed herein may be performed by a processor of a device that receives the sensed cardiac electrical signals from another device. For example, the processor 52 of external device 40 may receive the sensed cardiac electrical signals from ICD 14 via communication link 42. In other examples, the processor 52 of external device 40 may receive the sensed cardiac electrical signals from an external cardiac monitoring device, e.g., cardiac monitoring device 60 shown in FIG. 1C. In some examples, the external cardiac monitoring device 60 or the external device 40 may transmit sensed cardiac electrical signals to a patient monitoring database, such as the CARELINK® Network (Medtronic, Minneapolis, Minnesota USA), for processing and analysis by a networked computer or by a computer in a clinic, hospital or doctor's office. Depending on the processing requirements and power capacity of the device sensing the cardiac electrical signals, e.g., ICD 14, the sensed cardiac electrical signals may be transmitted to another device for processing and analysis. In still other examples, the processing and analysis of cardiac electrical signals as disclosed herein may be performed in a distributed manner across more than one device of a medical device system. For the sake of illustration, with no limitations intended, the techniques described in conjunction with FIG. 7 and other flow charts presented herein refer to ICD 14 as the device sensing the cardiac electrical signals and external device 40 as receiving the sensed cardiac electrical signals, which may be via cardiac monitoring device 60, and performing subsequent processing and analysis for determining acceptable or recommended sensing control parameters.

The cardiac electrical signals received at block 302 by processor 52 of external device 40 may be sensed by sensing circuit 86 of ICD 14 using at least two different sensing electrode vectors. The two sensing electrode vectors include one electrode common to both sensing electrode vectors but not both electrodes. For example, the first sensing electrode vector may include pace/sense electrodes 28 and 30 carried by lead 16 as shown in FIG. 1A and the second electrode vector may include one of pace/sense electrodes 28 or 30 paired with housing 15 or a defibrillation electrode 24 or 26.

The two sensed cardiac electrical signals may be passed to control circuit 80 from sensing circuit 86 as raw cardiac electrical signals, e.g., as wideband filtered signals from filter 74. The sensed cardiac electrical signals may be transmitted from ICD 14 to external device 40 as cardiac signal episodes that are a few seconds or a few minutes in duration for example. The sensed cardiac electrical signals may be received in real time via telemetry circuit 88 or stored in memory 82 and then passed to telemetry circuit 88 for transmission to external device 40 at a later time. In other examples, the sensed cardiac electrical signals may be transmitted in real time to cardiac monitoring device 60 and processed by the cardiac monitoring device or subsequently transmitted to external device 40. In still other examples, the sensed cardiac electrical signals may be surface ECG signals received by cardiac monitoring device 60 or external device 40 as described above.

At block 304, processor 52 of external device 40 constructs a third cardiac electrical signal that is expected to be sensed from a third sensing electrode vector, different than the first and second sensing electrode vectors but including one electrode from each of the sensed cardiac electrical signal sensing electrode vectors. The third sensing electrode vector signal may be determined by determining the voltage difference between the two sensed cardiac electrical signals at each sample point.

Figure 8:
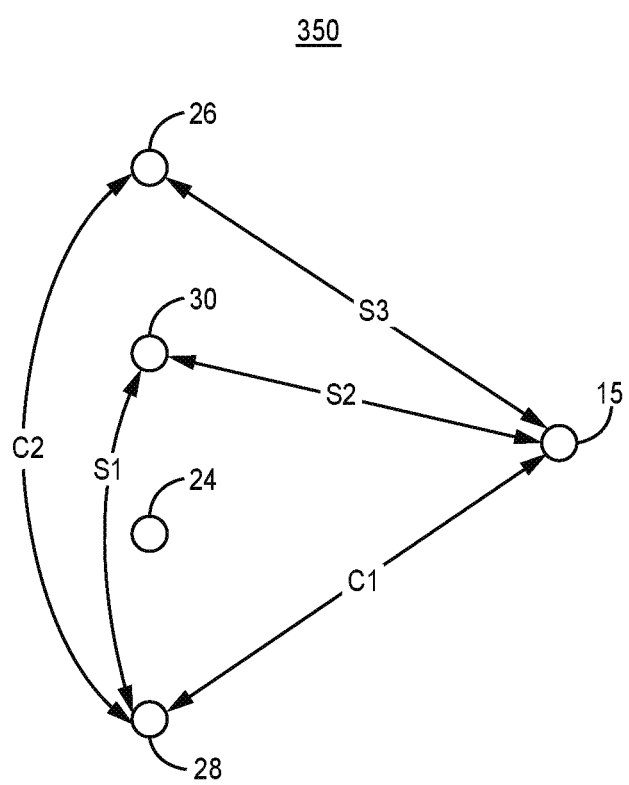
FIG. 8 is a diagram of some possible sensing electrode vectors that exist between the electrodes carried by the lead shown in FIG. 1A and the ICD housing.

FIG. 8 is a diagram 350 of some possible sensing electrode vectors that exist between the electrodes 24, 26, 28 and 30 carried by lead 16 and housing 15. Using the example given above, when the first sensing electrode vector S1 is between the pace/sense electrode 30 and pace/sense electrode 28 and the second sensing electrode vector S2 is between the pace/sense electrode 30 and the housing 15, a third, constructed cardiac electrical signal that is expected to be sensed between a third sensing electrode vector C1 (between pace/sense electrode 28 and the housing 15) can be determined by subtracting the S1 signal from the S2 signal. The third cardiac electrical signal expected to be sensed by the third sensing electrode vector C1 is therefore constructed based on two cardiac electrical signals sensed from sensing electrode vectors having one common electrode (pace/sense electrode 30 in this example).

The constructed cardiac electrical signal corresponds to a sensing electrode vector C1 including one electrode 28 from the first S1 sensing electrode vector used to sense the first sensed cardiac electrical signal and one electrode (housing 15) from the second S2 sensing electrode vector used to sense the second sensed cardiac electrical signal. The constructed cardiac electrical signal corresponding to the sensing electrode vector C1 between pace/sense electrode 28 and housing 15 is determined by determining the voltage amplitude differences of the two sensed cardiac electrical signals corresponding to vectors S1 and S2 at each sample point time.

Referring back to FIG. 7, in some examples, more than two sensed cardiac electrical signals may be received at block 302, so that more than one cardiac electrical signal may be constructed from the sensed cardiac electrical signals. In the example of FIG. 1A, all four electrodes 24, 26, 28 and 30 and housing 15 may be included in four different sensing electrode vectors used to sense four cardiac electrical signals so that a cardiac electrical signal expected to be sensed from each one of the remaining six possible sensing electrode vectors can be constructed. Using the four sensed cardiac electrical signals, additional cardiac electrical signals may be constructed by external device processor 52 to enable analysis of cardiac electrical signals corresponding to up to 10 different sensing electrode vectors available between the four electrodes 24, 26, 28, 30 and housing 15. For example, if four cardiac electrical signals are sensed using the four sensing electrode vectors between the housing 15 and each respective electrode 24, 26, 28 and 30, the cardiac electrical signals expected from the six sensing electrode vectors (defined by electrodes 24 and 26, electrodes 24 and 28, electrodes 28 and 30, electrodes 26 and 28, electrodes 26 and 30, and electrodes 28 and 30) that are available between the four electrodes may be constructed from the four sensed cardiac electrical signals for a total of ten cardiac electrical signals, sensed or constructed.

In some examples, a constructed cardiac electrical signal determined from two sensed cardiac electrical signals may be used by external device processor 52 to determine another constructed cardiac electrical signal. Referring again to FIG. 8, three cardiac electrical signals may be sensed: one between the pace/sense electrodes 28 and 30 (S1), one between pace/sense electrode 30 and housing 15 (S2), and one between defibrillation electrode 26 and housing 15 (S3). A constructed cardiac electrical signal expected to be sensed between pace/sense electrode 28 and housing 15 (C1) may be determined using the first two sensed cardiac electrical signals (from sensing vectors S1 and S2). Another constructed cardiac electrical signal expected to be sensed between pace/sense electrode 28 and defibrillation electrode 26 (C2) may be determined by determining the voltage amplitude differences between the constructed C1 cardiac electrical signal between electrode 28 and housing 15 and the sensed cardiac electrical signal between defibrillation electrode 26 and housing 15 (S3). Accordingly, multiple constructed cardiac electrical signals may be determined from multiple sensed cardiac electrical signals and combinations of constructed and sensed cardiac electrical signals.

At block 306, external device processor 52 determines sensed cardiac events for at least one of the sensed and/or constructed cardiac electrical signals. For example, processor 52 may determine sensed cardiac events for the constructed cardiac electrical signal by determining a narrowband filtered and rectified signal from the constructed cardiac electrical signal and applying a cardiac event sensing threshold to the rectified signal. Processor 52 may adjust the cardiac event sensing threshold according to the same cardiac event sensing threshold control parameters that are used by cardiac event detector 66 of sensing circuit 86. Processor 52 may repeat the analysis for at least one sensed cardiac electrical signal or both sensed cardiac electrical signals. In this way, programmer 52 may generate sensed cardiac event data corresponding to a third sensing electrode vector that enables a comparison of cardiac event sensing between the third sensing electrode vector and at least one sensing electrode vector that was used to sense the cardiac electrical signals received at block 302. This comparison of sensed events determined from the constructed cardiac electrical signal and a sensed cardiac electrical signal provides data for use in selecting the sensing electrode vector that provides reliable cardiac event sensing.

In some examples, processor 52 may determine the sensed cardiac events for at least one sensed cardiac electrical signal received at block 302 in addition to determining the sensed cardiac events for at least one constructed cardiac electrical signal. Processor 52 may determine a narrowband filtered and rectified signal from each received, sensed cardiac electrical signal and apply the cardiac event sensing threshold to determine sensed cardiac events in the manner that cardiac event detector 66 (FIG. 5) would sense cardiac events from a narrowband filtered and rectified signal. In some examples, processor 52 adjusts the cardiac event sensing threshold according to control parameters currently programmed in ICD 14, e.g., the current post sense blanking period, percentages used to determine the starting and intermediate amplitudes of the sensing threshold, the sense delay interval, the drop time interval and the sensitivity as described above in conjunction with FIG. 6. This analysis provides a comparison of cardiac event sensing using different sensing electrode vectors. However, processor 52 may determine sensed cardiac events for the constructed cardiac electrical signal(s) and sensed cardiac electrical signals for multiple different cardiac event sensing threshold control parameter settings.

For example, processor 52 may set and adjust the R-wave sensing threshold using multiple settings for at least one of the R-wave sensing threshold control parameters to determine sensed cardiac events from each cardiac electrical signal, sensed and constructed, according to the multiple R-wave sensing threshold control parameter settings. Using sensitivity as an example, processor 52 may determine sensed cardiac events from each of the constructed and sensed cardiac electrical signals for each available sensitivity setting in ICD 14 to generate sensed cardiac event data at block 306. Processor 52 may adjust the R-wave sensing threshold according to the sensing threshold control parameters for each cardiac electrical signal, sensed and constructed, to determine sensed cardiac events for each one of multiple sensitivity settings.

In other examples, processor 52 may determine sensed cardiac event signals for each available percentage setting used to determine the starting and/or the intermediate threshold as a percentage of the maximum peak amplitude determined during the post-sense blanking period. In still other examples, processor 52 may determine sensed cardiac event signals for each available sense delay interval setting and/or each available drop time interval setting. Processor 52 may determine sensed cardiac events for a range of a given sensing threshold control parameter or different combinations of sensing threshold control parameters for each of the sensed and constructed cardiac electrical signals so that comparisons between the sensed cardiac event intervals or sensed cardiac event rate may be made between different combinations of sensing control parameters and used for identifying reliable or recommended sensing control parameters.

At block 308, processor 52 may determine a predicted sensed cardiac event rate for each sensed and constructed cardiac electrical signal for each tested sensing threshold control parameter setting. For example, processor 52 may determine a predicted sensed atrial or ventricular rate based on the determined sensed cardiac events and/or generate a series of predicted sensed cardiac event intervals, e.g., PPIs or RRIs, at block 308. It is recognized that for at least one of the sensed cardiac electrical signals and set of sensing threshold control parameters the actual time of cardiac event signals sensed by cardiac event detector 66 of sensing circuit 86 may be determined by ICD control circuit 80 and transmitted to external device 40 with the sensed cardiac electrical signals. This actual sensed cardiac event interval data, a determined cardiac event rate and/or arrhythmia detection by ICD control circuit 80 may be transmitted to external device 40 and may be used as an expected cardiac event rate for comparative analysis of other sensing control parameter settings or may be used to compare to determined sensed cardiac event intervals or rates determined from the analysis of other cardiac electrical signals according to other sensing control parameter settings. A comparison between actual sensed cardiac event data and simulated sensed cardiac event data for the same sensing control parameters may be made to verify accuracy and consistency of the determined sensed cardiac events by processor 52 for the same set of sensing control parameters. In other examples, the determination of sensed cardiac events corresponding to the programmed sensing control parameters need not be performed by external device processor 52 because the data may be available from and transmitted by ICD 14.

At block 310, processor 52 may generate an output based on the sensed cardiac event data determined at block 308. In some examples, the output may be generated for display on display unit 54. For example, the output may be a graphical or tabular display of the data relating to cardiac event rate and/or cardiac event intervals determined for each sensing threshold control parameter setting applied to each sensed and constructed cardiac electrical signal. Processor 52 may generate an output of one or more recommended or acceptable sensing control parameter settings, which may be output for display, e.g., included in a GUI. A recommended or acceptable sensing electrode vector and/or sensitivity setting that results in an expected sensed cardiac event rate at a desired safety margin for sensing cardiac events may be determined and identified in a generated display, as an example. The expected or actual cardiac rate may be verified by a user or may be based on the median, mean or mode of the sensed cardiac event rates determined from all cardiac electrical signals and all sensing threshold control parameter settings used in the analysis, assuming the actual cardiac event rate is the most frequently determined sensed cardiac event rate from among the sensing control parameters analyzed. Techniques that may be performed by processor 52 for determining a sensing control parameter that provides a desired safety margin for sensing cardiac events at the expected or actual cardiac rate are described below in conjunction with FIGS. 8-13. In an example, the recommended sensitivity setting for a given sensing electrode vector may be one half of the minimum sensitivity setting that results in an expected or actual cardiac rate to provide a 2× (two times) safety margin for sensing cardiac events.

Accordingly, processor 52 may be configured to determine a rate of the determined sensed cardiac events, determine that the rate meets expected cardiac event rate criteria and determine that an associated sensing control parameter used to determine the sensed cardiac events meeting the expected cardiac event rate criteria is a recommended sensing control parameter. The expected cardiac event rate criteria may be an actual rate (which may be defined as an acceptable rate range) determined by a user and received by processor 52 via user interface 56. The expected cardiac event rate criteria may alternatively be a rate (or rate range) determined by processor 52 based on the most frequently determined rate from among the determined sensed cardiac events for each set of sensing control parameters (combinations of sensing electrode vector and cardiac event sensing threshold control parameter settings). In still other examples, as described below in conjunction with FIG. 9, the expected rate criteria may be defined by an arrhythmia detection or the time to detect an arrhythmia, such as VT or VF. When a set of sensing control parameters results in determined cardiac event intervals that meet expected rate criteria as determined at block 310, processor 52 may generate a display indicating the acceptable sensing control parameters.

The output generated by processor 52 at block 310 may include a programming command that is transmitted by telemetry unit 58 to ICD telemetry circuit 88 in some examples. The programming command may include a sensing electrode vector and/or one or more cardiac event sensing threshold control parameters selected as recommended settings for providing reliable cardiac event signal sensing based on the analysis of the sensed and constructed cardiac electrical signals. Control circuit 80 responds to the programming command by setting the selected sensing electrode vector and/or sensing threshold control parameter(s). Such programming may occur without requiring user intervention. In other examples, a user may confirm a recommended setting prior to transmission of the programming command, e.g., by interacting with user interface 56 or a GUI displayed on display unit 54 or via remote monitoring from a computer or other device in communication with external device 40.

Figure 9:
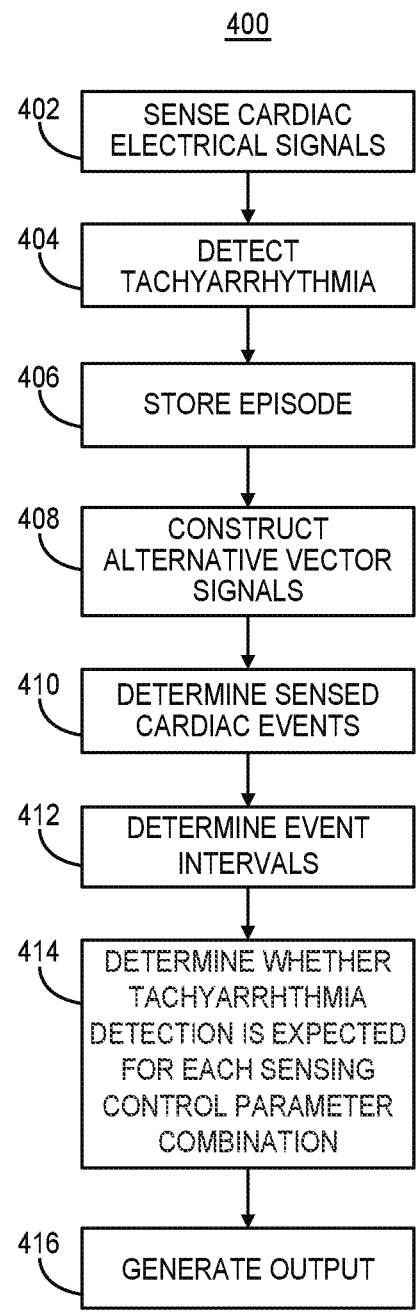
FIG. 9 is a flow chart of a method performed by a medical device for determining sensed cardiac events from multiple sensing electrode vector signals according to another example.

FIG. 9 is a flow chart 400 of a method performed by a medical device system for determining sensed cardiac events from multiple sensing electrode vector signals according to another example. At block 402 at least two different cardiac electrical signals are sensed by sensing circuit 86 using two different sensing electrode vectors. At least one electrode is common to both of the two sensing electrode vectors to enable control circuit 80 or external device processor 52 to construct at least one more cardiac electrical signal corresponding to a third sensing electrode vector.

At block 404, control circuit 80 may detect tachyarrhythmia based on at least one of the sensed cardiac electrical signals. The tachyarrhythmia may be an induced tachyarrhythmia or a spontaneously occurring tachyarrhythmia. In response to the tachyarrhythmia, control circuit 80 stores an episode of each of the two sensed cardiac electrical signals in memory 82 at block 406. As described above, the two sensed cardiac electrical signals may be wideband filtered signals received from sensing circuit 86. The stored episode extends from the first tachyarrhythmia interval detected by control circuit 80 (or earlier) until the tachyarrhythmia detection is made (or later) so that control circuit 80 or processor 52 of external device 40 is able to determine the time from the first tachyarrhythmia interval that contributed to tachyarrhythmia detection (e.g., contributed to the NID being reached) until tachyarrhythmia detection is made, referred to as the "time to detect." While not explicitly shown in FIG. 9, it is understood that therapy delivery circuit 84 of ICD 14 may respond to the tachyarrhythmia detection by generating a therapy, e.g., ATP or CV/DF shock therapy.

At block 408, processor 52 constructs at least one alternative sensing electrode vector signal from the two sensed cardiac electrical signals. At block 408, control circuit 80 may transmit the stored sensed cardiac electrical signal episodes corresponding to the detected tachyarrhythmia to external device 40 for processing and analysis. Control circuit 80 may perform the processing and analysis for determining sensed cardiac events from multiple cardiac electrical signals in some examples. However, in order to reduce processing burden and conserve power source 98 of ICD 14, processing and analysis of sensed cardiac electrical signals may be performed by an external device, e.g., external device 40 shown in FIG. 1A. As noted above, processing and analysis of cardiac electrical signals described in conjunction with flow charts presented herein, including the flow chart 400 of FIG. 9, may be performed by control circuit 80, external device processor 52, or cooperatively by both control circuit 80 and external device processor 52 or another processing device such as a remote computer in communication with external device 40.

Accordingly, while transmission of the stored sensed cardiac electrical signal episodes is not explicitly shown in FIG. 9, it is to be understood that transmission of sensed cardiac electrical signals and related data may occur at or after block 406 in order to enable an external processor 52 to obtain sensed cardiac electrical signals and perform subsequent processing and analysis. Furthermore, in some examples such as when the detected tachyarrhythmia is an induced tachyarrhythmia, the sensed cardiac electrical signals may be transmitted in real time to external device 40 during the tachyarrhythmia induction procedure. When transmitted in real time, ICD telemetry circuit 88 may be capable of transmitting a greater number of sensed cardiac electrical signals (corresponding to more sensing electrode vectors) than the number of cardiac electrical signal episodes that memory 82 has the capacity to store (for later transmission). For example, four different sensing electrode vector signals may be transmitted by ICD telemetry circuit 88 in real time during a tachyarrhythmia induction procedure while two different sensing electrode vector signals may be stored in memory 82 for later transmission to external device 40.

Figure 10:
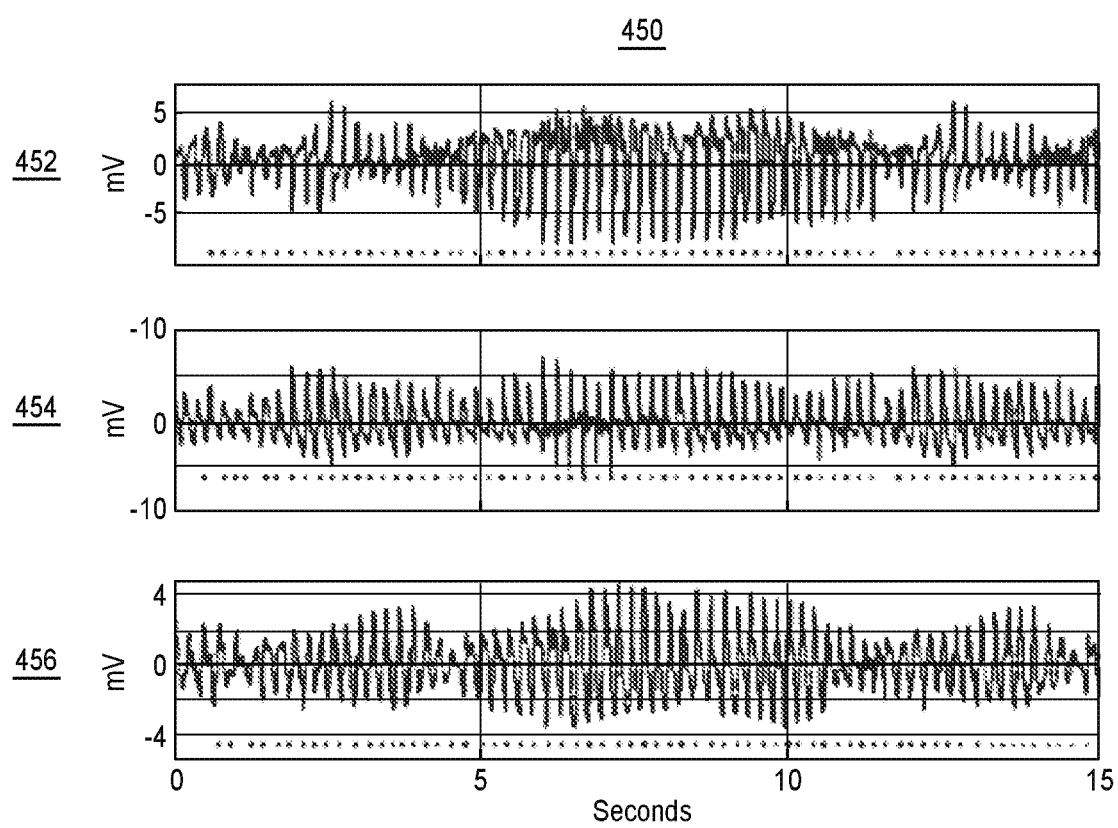
FIG. 10 is a diagram of three cardiac electrical signals that may be analyzed according to the techniques disclosed herein.

FIG. 10 is a diagram 450 of three cardiac electrical signals that may be obtained by a processor and analyzed according to the techniques disclosed herein by a medical device system. In this example, cardiac electrical signal 452 is a sensed cardiac electrical signal that is sensed by a first sensing electrode vector, e.g., between pace/sense electrodes 28 and 30 (shown in FIG. 1A). Cardiac electrical signal 454 is a sensed cardiac electrical signal that is sensed using a second sensing electrode vector, e.g., between pace/sense electrode 30 and housing 15. The third cardiac electrical signal 456 is a constructed cardiac electrical signal that may be determined by processor 52 using the two sensed cardiac electrical signals 452 and 454. Constructed cardiac electrical signal 456 corresponds to a cardiac electrical signal that would be sensed between sensing electrode 28 and housing 15. Constructed cardiac electrical signal 456 may be determined by processor 52 by subtracting the first sensed cardiac electrical signal 452 from the second sensed cardiac electrical signal 454 (note that the millivolt scales are different for the different signals shown in FIG. 10). By constructing a third cardiac electrical signal 456 from two sensed cardiac electrical signals 452 and 454, processor 52 is able to determine sensed cardiac events from at least three different available sensing electrode vector signals to generate data relating to the determined sensed cardiac events, e.g., event intervals or rates, according to specified sensing threshold control parameter settings. This generated data enables processor 52 to make comparisons between sets of sensing control parameters, e.g., different combinations of sensing electrode vector and multiple sensitivities, without having to reprogram ICD 14 and without recording cardiac electrical signals sensed according to a relatively large number of different sensing control parameters. Selection of an acceptable sensing electrode vector and corresponding sensing threshold control parameter settings may be made based on the sensed cardiac event data determined by a processor configured to simulate the sensing operations of sensing circuit 86, such as narrowband filtering and rectifying of the sensed and constructed signals and applying a multi-level cardiac event sensing threshold amplitude to determine sensing threshold crossings.

The two sensed cardiac electrical signals 452 and 454 are sensed by sensing circuit 86 during VF in this example and may be transmitted in real time to external processor 52, e.g., during a VF induction procedure. In other examples, the two sensed cardiac electrical signals 452 and 454 are stored in memory 82 in response to control circuit 80 detecting a spontaneous VF episode and transmitted to external device 40, e.g., in response to an interrogation command received by ICD telemetry circuit 88 from external telemetry unit 58. In some examples, processor 52 may control display unit 54 to generate a display of sensed cardiac electrical signals 452 and 454 and the constructed cardiac electrical signal 456, e.g., as part of a GUI that may include additional data relating to determined sensed cardiac events and associated event intervals and/or rates.

The cardiac electrical signals 452, 454 and 456 may be displayed as the wideband filtered cardiac electrical signals before narrowband filtering and rectification is performed for obtaining a filtered, rectified signal that the cardiac event sensing threshold is applied to according to selected sensing threshold control parameter settings. As shown and described below in conjunction with FIG. 11, processor 52 may determine a filtered and rectified signal from each of the raw cardiac electrical signals 452, 454 and 456 according to the filtering performed by ICD sensing circuit 86 prior to cardiac event detector 66 so that the sensing threshold control parameter settings applied by processor 52 for determining sensed cardiac events simulate the performance of cardiac event detector 66 for a given set of sensing control parameters (sensing electrode vector and sensing threshold control parameter settings).

Returning to FIG. 9, processor 52 determines sensed cardiac events from at least one constructed cardiac electrical signal at block 410. In examples presented herein, processor 52 determines sensed cardiac events from multiple cardiac electrical signals, sensed and constructed, for multiple settings of at least one sensing threshold control parameter. Processor 52 may determine sensed cardiac events by identifying sensing threshold crossing times by the cardiac electrical signal under analysis when the sensing threshold is being adjusted according to a specified set of sensing threshold control parameter settings. In some examples, sensed cardiac events and associated event intervals are known for one of the sensed cardiac electrical signals transmitted to external device 40, at least for the programmed sensing threshold control parameters that resulted in tachyarrhythmia detection. Processor 52 may determine the sensed cardiac events from the constructed cardiac electrical signal at block 410 using the same sensing threshold control parameters used by sensing circuit 86 and control circuit 80 that resulted in the tachyarrhythmia detection by control circuit 80.

Additionally, processor 52 may determine sensed cardiac events from the constructed cardiac electrical signal for multiple settings of one or more sensing threshold control parameters. For the sake of illustration, processor 52 may determine sensed cardiac events from the constructed cardiac electrical signal according to multiple sensitivity settings. Additionally, processor 52 may determine sensed cardiac events from one or both sensed cardiac electrical signals according to multiple sensitivity settings or other sensing threshold control parameter settings, which may be different than the programmed sensing threshold control parameter settings used to sense cardiac events by sensing circuit 86 that led to actual detection of the tachyarrhythmia by control circuit 80.

As indicated above, the sensed cardiac events determined as sensing threshold crossing times are determined by applying the same filtering, rectification and any other processing of the constructed cardiac electrical signal as performed by sensing circuit 86 on a sensed cardiac electrical signal prior to passing the signal to event detector 66 (FIG. 5). Processor 52 applies selected sensing threshold control parameters in the same manner as event detector 66 to determine sensed cardiac events, e.g., ventricular sensed events or atrial sensed events, from the cardiac electrical signal under analysis. Using the example shown in FIG. 6, processor 52 may determine a starting threshold amplitude 212 based on a maximum peak amplitude 203 determined during a blanking period 240, hold the starting threshold 212 for a sense delay interval 242, decrement to an intermediate threshold amplitude 216 held for a drop time interval 244, then decrement to the sensitivity 220 to determine sensed cardiac events (based on sensing threshold crossings) from the episode of the cardiac electrical signal under analysis. This process may be repeated multiple times using a different sensitivity setting each time to determine sensed cardiac events for multiple different sensitivity settings for a given cardiac electrical signal. The process of determining sensed cardiac events for multiple sensitivity settings may be repeated for each cardiac electrical signal, sensed or constructed.

Using the determined sensed cardiac events for each cardiac electrical signal being analyzed according to each setting of one or more sensing threshold control parameters, processor 52 determines associated cardiac event intervals at block 412, e.g., RRIs or PPIs, that occur between each consecutive pair of determined sensed cardiac events. Using the determined cardiac event intervals at block 414, processor 52 may determine whether the tachyarrhythmia detection is predicted to be made from the corresponding sensing electrode vector signal and sensing threshold control parameter settings. In some examples, at block 414, processor 52 may determine a predicted time to detect the tachyarrhythmia for each combination of sensing control parameter settings analyzed, e.g., for each combination of sensing electrode vector and cardiac event sensing threshold control parameter settings. In other examples, processor 52 may determine whether the tachyarrhythmia is predicted to be detected within a threshold interval of time, e.g., within 30 seconds, or within the time interval represented by a cardiac electrical signal episode stored in memory 82 in response to the actual tachyarrhythmia detected at block 404.

Processor 52 may determine whether tachyarrhythmia detection is expected at block 414 and determine the predicted time to detect the tachyarrhythmia. Processor 52 uses the tachyarrhythmia detection criteria used by ICD 14 relating to detecting tachyarrhythmia intervals from the determined sensed event intervals and for determining when the required NID to detect the tachyarrhythmia is reached. The time to detect the tachyarrhythmia may be determined as the time from an earliest tachyarrhythmia interval identified from among the determined sensed cardiac event intervals until a required NID is reached that includes the earliest tachyarrhythmia interval. The earliest tachyarrhythmia interval may be the first tachyarrhythmia interval identified from the cardiac electrical signal under analysis for a given set of sensing threshold control parameter settings. In other examples, the time to detect may be determined from a standardized starting time to the time the NID is reached for a given set of sensing control parameters. The standardized starting time may be the time of the first tachyarrhythmia interval of the actual sensed cardiac electrical signal that led to tachyarrhythmia detection. In other examples, the standardized starting may be the earliest or latest tachyarrhythmia interval identified from among all determined sensed cardiac event intervals for a given sensing electrode vector or all sensing electrode vectors.

In some examples, processor 52 may require a minimum number of sensed cardiac events in the cardiac signal episodes for use in determining the event intervals at block 412 and determining a time to detect tachyarrhythmia at block 414. Because tachyarrhythmia detection criteria may require a threshold number of tachyarrhythmia intervals out of the most recent predetermined number of cardiac event intervals, the number of sensed cardiac events in the received sensed cardiac signals may be required to be at least the threshold number of tachyarrhythmia intervals required to detect the tachyarrhythmia. To illustrate, if the NID is set to 30 tachyarrhythmia intervals out of the most recent 40 cardiac event intervals, processor 52 may require that at least one of the sensed cardiac electrical signal episodes include at least 30 sensed cardiac events to continue analysis of the sensed and constructed signals associated with the acquired episode. When a threshold number of sensed cardiac events are included in the sensed cardiac electrical signal(s), each of the sensed and constructed signals may undergo further analysis. In some cases, a given episode of a sensed or constructed signal may be repeated in a looping manner during the analysis at block 414 to provide a signal episode of sufficient length to predict a time to detect tachyarrhythmia. The predicted tachyarrhythmia detection time for some sensing control parameters may be longer than the original cardiac signal episode. As such, the cardiac signal episodes may be looped to generate an episode that is up to one minute long, for example, for each sensed and constructed cardiac signal undergoing analysis to promote an adequate episode duration for predicting a tachyarrhythmia detection time according to various sensing control parameter settings.

At block 416, processor 52 may generate an output of expected tachyarrhythmia detections, the determined times to detect the tachyarrhythmia and/or related cardiac event interval or rate data for each combination of sensing control parameter settings analyzed. Processor 52 may generate data in a tabular or graphical format for display on display unit 54, which may be part of a GUI. In some examples, processor 52 may generate an output of a recommended sensing control parameter setting, e.g., a recommended sensing electrode vector, a recommended cardiac event sensing threshold control parameter such as the sensitivity or other sensing threshold control parameter(s) described above in conjunction with FIG. 6. As described below in conjunction with FIG. 13, a recommended sensing threshold control parameter setting for a given sensing electrode vector may be based on the expected tachyarrhythmia detections and/or determined times to detect tachyarrhythmia for that sensing electrode vector and a desired safety margin for sensing cardiac events. In some examples, the output generated by processor 52 at block 416 includes a programming command transmitted to ICD 14 to program a recommended sensing control parameter or combination of parameters, such as a sensing electrode vector and corresponding sensitivity or other cardiac event sensing threshold control parameter(s).

Figure 11:
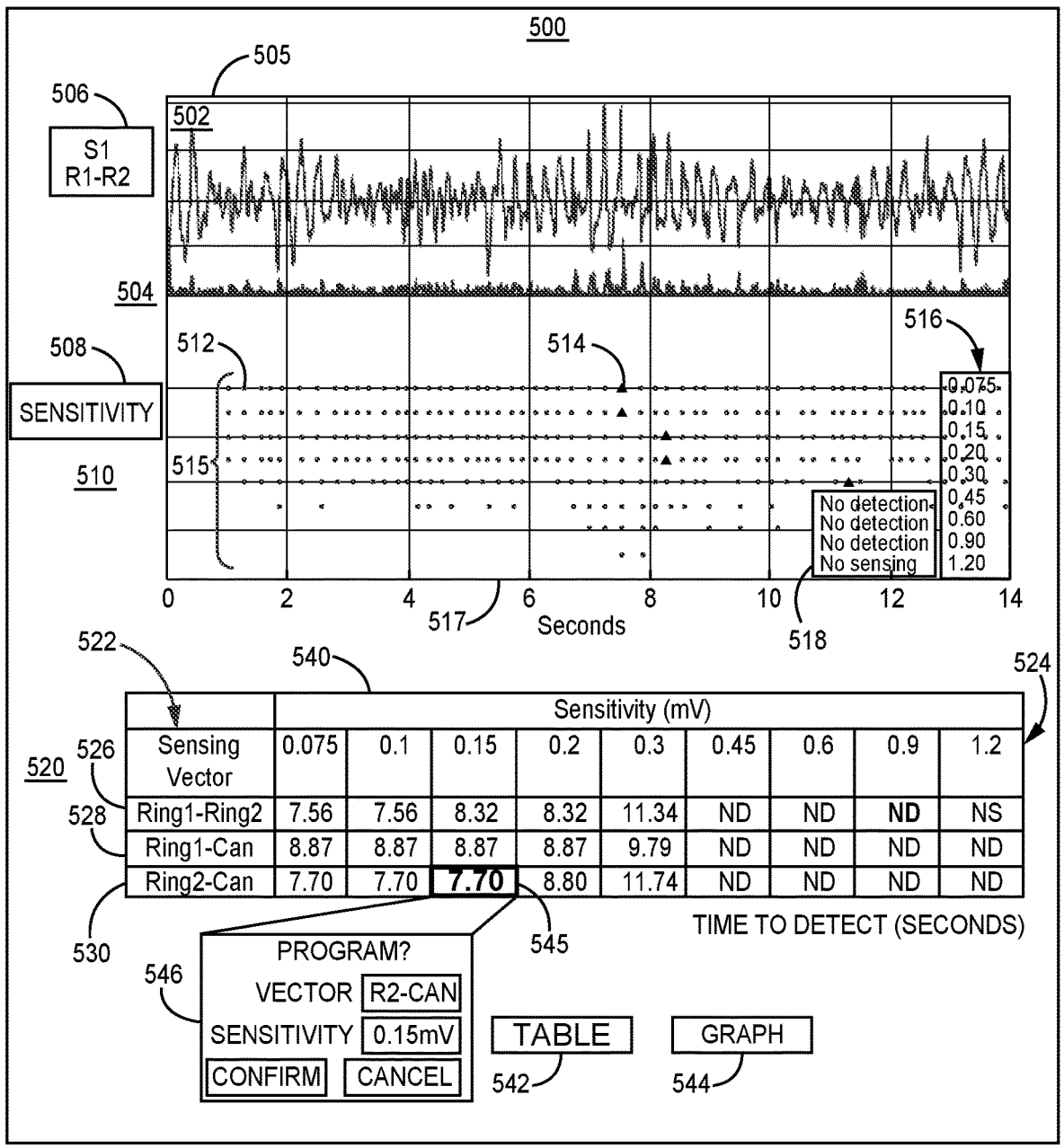
FIG. 11 is a diagram of a graphical user interface (GUI) that may be generated as output by a processor for display on a display unit according to one example.

FIG. 11 is a diagram of a GUI 500 that may be generated as output at block 416 of FIG. 9 by external device processor 52 for display on display unit 54 according to one example. In some examples, display 54 of external device 40 is a touch-sensitive screen that is configured to both display GUI 500 to a user as well as provide touch-sensitive regions of GUI 500 that allow the user to provide input to GUI 500. In other examples, a user may navigate to different user input portions of GUI 500, e.g., selectable windows, pop-up-windows, menus, icons, buttons or the like, using a mouse, keyboard or other user interface input device.

GUI 500 may include a display of a cardiac electrical signal 502, a timing diagram 510, and a data table 520. In a cardiac electrical signal window 505 of GUI 500, a cardiac electrical signal 502 is displayed, which may be a sensed or constructed cardiac electrical signal. In this example, cardiac electrical signal 502 is a sensed signal from a sensing electrode vector between pace/sense electrodes 28 and 30 (referred to as ring 1 and ring 2, respectively, or R1 and R2 in GUI 500) of lead 16. The cardiac electrical signal displayed in window 505 may be selectable by a user interacting with GUI 500. For example, a drop down or scrollable menu 506 of available cardiac electrical signals may be included in GUI 500 to enable a user to select different cardiac electrical signals, sensed or constructed, for display in window 505. In addition to a sensed or constructed cardiac electrical signal, GUI 500 may include a display of an electrocardiogram signal from the patient, which may be received via external ports 55 (shown in FIG. 1A) and stored in memory 53, to provide the user with a visual comparison between the electrocardiogram and the sensed or constructed cardiac electrical signal.

Cardiac electrical signal 502 is the wideband filtered, unrectified signal received from ICD 14. In some instances, cardiac electrical signal 502 is transmitted from ICD 14 after being stored in memory 82 by control circuit 80 in response to a tachyarrhythmia detection, e.g., a VF detection. In other instances, cardiac electrical signal 502 may be a sensed cardiac electrical signal that is transmitted in real time from ICD 14 to external device 40 during a tachyarrhythmia induction procedure. In still other examples, a constructed cardiac electrical signal determined by processor 52 during post-processing and analysis may be selected from a list in user input menu 506 for display in window 505. In other examples, instead of displaying each sensed or constructed cardiac electrical signal one at a time in window 505, multiple (or all sensed and constructed) cardiac electrical signals may be displayed simultaneously in window 505. Using menu 506, a user may be able to select two or more cardiac electrical signals at a time for display in window 505 for comparison and review.

Processor 52 may determine the narrowband filtered and rectified cardiac electrical signal 504 from wideband filtered cardiac electrical signal 502. The narrowband filtered and rectified signal 504 may be included in the display window 505. Filtered and rectified cardiac electrical signal 504 represents the narrowband filtered and rectified signal that would be passed to cardiac event detector 66 of sensing circuit 86 during real time cardiac event sensing by ICD 14. Processor 52 applies the cardiac event sensing threshold, adjusted according to sensing threshold control parameter settings, to the filtered and rectified cardiac electrical signal 504 for determining sensed cardiac events. When more than one sensed and/or constructed cardiac electrical signal is selected from menu 506 for display in window 505, the corresponding, time-aligned filtered and rectified cardiac electrical signal may be displayed along with the sensed or constructed cardiac electrical signal. In other examples, window 505 may include a display of only the narrowband filtered and rectified cardiac electrical signal(s) 504 without displaying the corresponding wideband filtered signal(s) 502 or vice versa.

Timing diagram 510 includes sensed cardiac event markers 512 corresponding to sensed cardiac events determined from the filtered and rectified cardiac electrical signal 504 by processor 52. In timing diagram 510, each marker 512 is generated by processor 52 to indicate the time of a cardiac event sensing threshold crossing by filtered, rectified signal 504 determined by processor 52 as the time that a cardiac event would be expected to be sensed by sensing circuit 86 from the corresponding filtered and rectified cardiac electrical signal 504. Timing diagram 510 may include multiple rows 515 of sensed cardiac event markers 512, with each individual row displaying event makers 512 generated by processor 52 according to a different cardiac event sensing threshold control parameter setting. GUI 500 may include a drop down or scrollable menu 508 as a user input portion of GUI 500 for selecting a cardiac event sensing threshold control parameter. Using menu 508, a user may select a control parameter from among the programmable cardiac event sensing threshold control parameters. Sensitivity is shown as the selected sensing control parameter in the menu 508 such that each individual row of rows 515 corresponds to a different sensitivity setting as displayed in a parameter setting window 516 adjacent to the respective row of sensed cardiac event markers 512. In the example shown, the sensed cardiac event markers 512 are shown for each available sensitivity setting between 0.075 mV and 1.2 mV as listed in sensing parameter setting window 516.

In some examples, a user may select different sensing threshold control parameters from menu 508 to cause processor 52 to generate and display cardiac sensed event markers 512 for each available setting of the selected sensing threshold control parameter. For instance, a user may select the percentage used to set the starting threshold amplitude, the percentage used to set the intermediate threshold amplitude, the sense delay interval, the drop time interval or the sensitivity to cause processor 52 to generate a timing diagram 510 of rows 515 of cardiac sensed event markers 512 corresponding to each available (or user selected) setting of the selected parameter (and the cardiac electrical signal displayed in window 505).

In some cases, two or more different cardiac event sensing threshold parameters may be selected to generate a timing diagram 510 that includes a row of cardiac sensed event markers 512 for each combination of settings or a selected subset thereof with the corresponding parameter settings displayed in window 516. In still other examples, window 516 may be a user input portion of GUI 500 to enable the user to select which settings of a selected sensing threshold control parameter are included in the data displayed in timing diagram 510 (and optionally in other portions of GUI 500, such as table 520 described below). A user may select the sensing threshold control parameter(s) from menu 508 and select individual settings for each selected parameter from window 516, e.g., using a mouse, pointer, touch screen or the like. In response to the user input, processor 52 may determine any data necessary from the selected cardiac electrical signal(s) and generate a timing diagram 510 of cardiac sensed event markers 512, which may be arranged in rows with each row corresponding to a combination of selected sensing threshold control parameter settings. While not shown in FIG. 11, it is contemplated that GUI 500 may include a display of determined cardiac event intervals (e.g., in milliseconds) in timing diagram 510 and/or a determined cardiac event rate (e.g., in beats per minute).

Timing diagram 510 may further include a tachyarrhythmia detection marker 514 in each row of rows 515 corresponding to a predicted time that tachyarrhythmia is expected to be detected according to the corresponding set of sensing control parameters. The tachyarrhythmia detection marker 514 may be aligned in time (along timeline 517 relative to the determined sensed event markers 512) to indicate the time that an NID is reached for a given sensitivity setting (or other selected parameter setting) based on the determined sensed cardiac event markers 512. Processor 52 may determine the time to detect tachyarrhythmia, the time to detect VF in this example, by determining and summing the time intervals between consecutive sensed cardiac event markers 512 that include the first and last VF intervals counted toward reaching the NID. Processor 52 may generate a tachyarrhythmia detection marker 514 as part of the GUI 500 displayed by display unit 54 to indicate the time that VF is detected from the filtered rectified signal 504 for each sensitivity setting 516.

In addition to or alternatively to tachyarrhythmia detection markers 514, GUI 500 may include a window 518 indicating tachyarrhythmia is expected to be detected or not detected. Window 518 may additionally or alternatively indicate when cardiac events are expected to be sensed or not sensed at all for a given set of sensing control parameters. In the example shown, when the sensitivity is 0.45 mV or higher for sensing cardiac events from the selected cardiac electrical signal 502, VF is not predicted to be detected. An indication of "No detection" is shown in window 518 for each sensitivity setting 0.45 mV, 0.60 mV, and 0.9 mV. When the sensitivity is set at the highest setting of 1.2 mV, cardiac events are not sensed, as indicated by no sensed cardiac event markers 512 in the row corresponding to 1.2 mV sensitivity. Instead of or in addition to indicating "No detection" in window 518, an indication of "No sensing" may be shown in window 518 adjacent to sensitivity setting 1.2 mV.

In other illustrative examples of GUI 500, instead of showing all rows 515 of sensed cardiac event markers determined for each available or selected sensing threshold control parameter in timing diagram 510, a user may select the sensing threshold control parameter from menu 508 and a single setting for the selected sensing threshold control parameter from window 516 (or an analogous menu of available settings). Processor 52 may generate the GUI 500 including a single row of sensed cardiac event markers corresponding to determined sensed cardiac events from the selected cardiac electrical signal. Window 516 may be configured to enable a user to scroll or toggle through different settings of the sensing threshold control parameter to visualize changes in the locations of the sensed cardiac event markers 512 and tachyarrhythmia detection markers 514 along the horizontal timeline 517 of timing diagram 510.

While not explicitly shown in GUI 500, other user input portions of GUI 500 may include zoom in and zoom out buttons for viewing cardiac electrical signal window 505 and/or timing diagram 510 at different horizontal time resolutions and, in the case of cardiac electrical signal window 505, vertical voltage scale resolution. Other user input portions of GUI 500 may include a pause, fast forward, reverse, store, download, save, print or other operational buttons that enable a user to view, print and/or save data displayed in GUI 500 as desired.

Processor 52 may generate data included in data table 520 for display on display unit 54 in GUI 500 to summarize the sensed event data determined from each sensed and constructed cardiac electrical signal for each sensing threshold control parameter tested. In the example shown, table 520 includes the sensing electrode vector in the first column 522 that corresponds to each sensed and constructed cardiac electrical signal analyzed. The sensing electrode vectors listed in column 522 may correspond to the sensed and constructed cardiac electrical signals selectable from menu 506. In some examples, the cells in column 522, each listing a sensing electrode vector, may be selectable by a user interacting with GUI 500 for simultaneously selecting which cardiac electrical signal is displayed in window 505 and which corresponding data is shown in timing diagram 510. The sensing threshold control parameter 540 analyzed for determining the data displayed in timing diagram 510 may be listed in the first cell 540 of table 520. The analyzed sensing control parameter settings may be listed in the first row 524 of table 520. The selected sensing threshold control parameter is shown as being sensitivity in cell 540, and the sensitivity settings analyzed are listed in the first row 524.

The data cells in the body of table 520 indicate the time (in seconds) to detect VF determined by processor 52 based on the determined sensed cardiac events for the corresponding sensing electrode vector listed in column 522 and sensitivity setting listed in row 524. For example, the row 526 labeled Ring1-Ring2 in this example corresponds to the cardiac electrical signal 502, sensed between pace/sense electrodes 28 and 30. The time to detect VF in seconds listed in each data cell for each sensitivity setting corresponds to the time of the tachyarrhythmia detection marker 514 for each sensitivity setting 516 shown in the timing diagram 510. No detection (ND) is indicated in the data cells for the sensitivity settings 0.45, 0.6 and 0.9 mV in row 526 at which VF is not detected. No sensing (NS) is indicated for the sensitivity setting 1.2 mV at which no cardiac events are predicted to be sensed as indicated by no sensed event markers for sensitivity setting 1.2 mV in timing diagram 510.

Table 520 may include the time to detect for each of the sensing electrode vectors listed in the first column 522 and analyzed by processor 52. In this example, a second sensing electrode vector between pace/sense electrode 30 and housing 15, referred to a "Ring1-Can" in row 528 of table 520, and a third sensing electrode vector between the pace/sense electrode 28 and housing 15, referred to as "Ring2-Can" in row 530 of table 520, are shown with corresponding predicted VF detection times for sensitivity settings 0.075 to 0.3 mV. No VF detection (ND) is predicted from the sensed and constructed cardiac electrical signals corresponding to these sensing electrode vectors for sensitivity settings of 0.45 mV and higher. The higher sensitivity settings result in predicted undersensing of the fibrillation waves and a predicted failure to detect VF.

The sensitivity setting and sensing electrode vector that are currently programmed in ICD 14 may be indicated in table 520, as shown by the bolded font for time to detect corresponding to the Ring1-Ring2 sensing electrode vector and 0.9 mV sensitivity. At this sensitivity, the VF episode is not detected from the first sensed cardiac electrical signal in this example. The data cells containing a time to detect VF, corresponding to a sensing electrode vector and sensitivity setting (e.g., all sensitivity settings less than 0.3 mV for all sensing electrode vectors in this example), may be indicated as acceptable sensing control parameter settings in table 520. Indication of acceptable sensing control parameter settings may be made in GUI 500 by generating the display of times to detect VF in the corresponding data cells in a stylized font, e.g., green or other colored font, bolded, underlined or other distinguishing characteristic. Additionally or alternatively, times to detect that correspond to unacceptable control parameter settings (all ND and NS cells for sensitivities greater than 0.3 mV in this example) may be indicated as unacceptable, e.g., by red font, strike through or other distinguishing display characteristic. Unacceptable sensitivity settings may alternatively or additionally be indicated in row 524 by shading or other formatting of the columns that include all "ND" and/or "NS" indicators.

In other examples, instead of displaying the time to detect the tachyarrhythmia in the data cells of table 520, the data cells may contain an indication of detection or no detection and/or sensing or no sensing. For example, the data cells containing a time to detect tachyarrhythmia in GUI 500 may alternatively contain a "VT" or "VF" to indicate detection of VT or VF is expected for the combination of sensing control parameters and "ND" to indicate no detection is expected. The indication of detection or no detection may distinguish combinations of sensing control parameter settings that are acceptable from sensing control parameter settings that are deemed unacceptable due to an expected failure to detect the tachyarrhythmia episode. In some cases, a tachyarrhythmia may be detected from a sensing electrode vector signal according to a sensing threshold control parameter but at a predicted detection time that is longer than an acceptable threshold detection time. Processor 52 may generate an indication of no detection for display in GUI 500 for a specified combination of sensing control parameters that results in a predicted detection after a specified time limit, e.g., after more than 30 seconds. Processor 52 may generate an indication of detection for display in GUI 500 for a specified combination of sensing control parameters that results in detection predicted within the specified time limit, e.g., within 30 seconds or less.

The GUI 500 shown in FIG. 11 illustrates data that may be included in a GUI generated for display by display unit 54. In other examples, GUI 500 may include less data or more data than shown in FIG. 11. For example, display of the cardiac electrical signal 502 and/or the narrowband filtered and rectified signal 504 may be optional. In some examples, timing diagram 510 is omitted with summary data presented in table 520 with an indication of acceptable sensing control parameter settings. In some examples, only table 520 may be shown in GUI 500 or only timing diagram 510, with or without an indication of acceptable or recommended sensing control parameter settings.

A user interacting with GUI 500 may select one or more sensing control parameter settings for programming in ICD 14. For example, data cells included in table 520 may be user selectable using a pointer, mouse, touch screen or the like. A user may select a combination of sensing electrode vector and sensitivity setting by selecting a data cell in table 520 and confirming the programming selection using a user input program button or icon. In an illustrative example, upon selection by a user, a data cell 545 or its contents may become enlarged or bolded. A program confirmation user input window 546 may be displayed in response to the user selection of a data cell 545, e.g., in a programming pop-up window. The program confirmation user input window 546 may indicate the selected programmable parameters corresponding to the selected data cell, e.g., sensing electrode vector and sensitivity setting, and include "confirm" and "cancel" user input buttons for confirming or cancelling the programming of the selected settings in ICD 14. In other examples, a cell in column 522 corresponding to a specified sensing electrode vector and a cell in row 524 corresponding to a sensitivity setting may be selectable by a user for generating a sensing control parameter programming command by external device 40 for transmission to ICD 14. In response to a user input confirmation of a sensing control parameter setting(s), processor 52 may generate the programming command for transmission to ICD 14 via telemetry unit 58.

Figure 12:
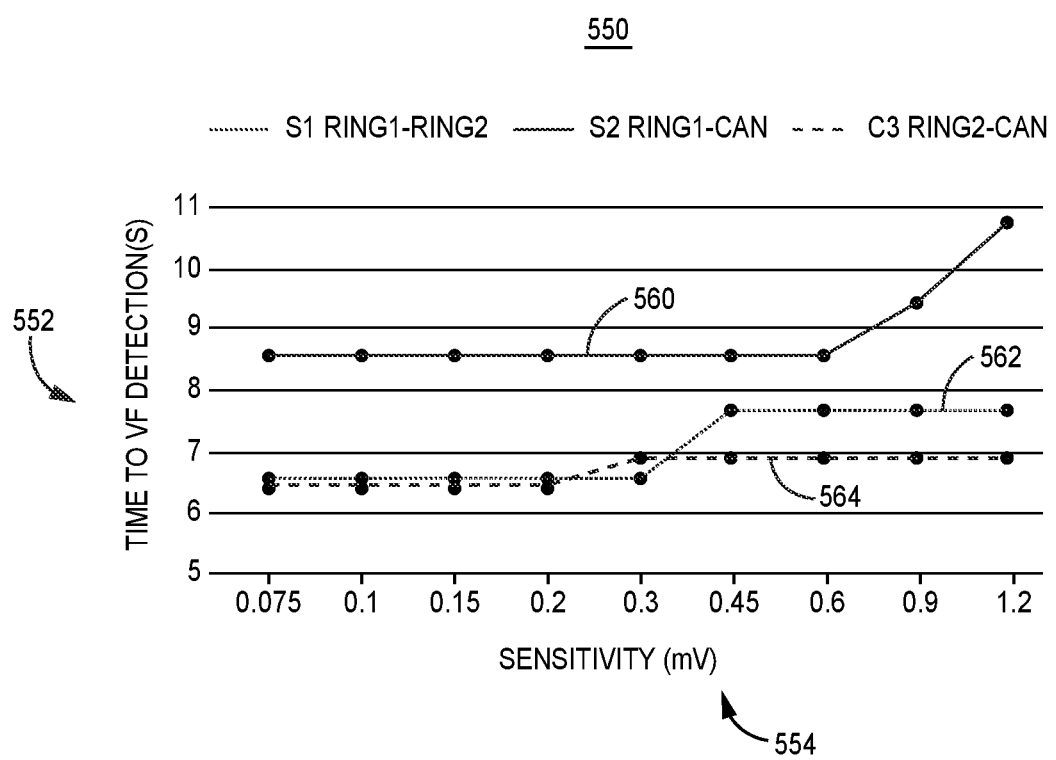
FIG. 12 is a graph of tachyarrhythmia detection time data that may be determined by a processor of a medical device system and generated as output for display according to one example.

In some examples, GUI 500 may include user selection buttons 542 and 544 that allow a user to select or toggle between a table view or a graph view of the data generated by processor 52. In the example shown, the table view is selected as indicated by enlarged font of button 542 and the display of table 520 in GUI 500. By clicking on the graph button 544, a user may switch the display from the table 520 to a graph of the data shown in table 520. A user may toggle back and forth between a tabular listing of the data as shown in FIG. 11 and a graphical view of the data, e.g., as shown in FIG. 12 and described below. Alternatively, a table of the generated data may appear in a pop-up window when table button 542 is clicked on or otherwise selected by a user, and a graph of the generated data may appear in a pop-up window when the graph button 544 is clicked or selected by a user.

GUI 500 may include other patient-related data such as a patient name, birthdate or other identification. GUI 500 may further include other informational data such as a display of the date and time that a cardiac electrical signal episode was recorded by ICD 14 (when transmitted at a later time), therapy delivered, therapy outcome, or the like. GUI 500 may include more or fewer user input portions and/or more or fewer data windows, tables, etc. than shown in FIG. 11.

The techniques set forth herein provide specific improvements to the computer-related field of programming medical devices that have practical applications. For example, the use of the techniques herein may enable external device 40 to generate visualizations of cardiac electrical signal data, determined cardiac event data, determined cardiac event interval data, determined cardiac event rate data, and/or determined cardiac arrhythmia data corresponding to multiple sensing control parameter settings that define the cardiac event sensing performed by ICD 14. Such visualizations may enable an external device, such as external device 40, to inform a user as to how the ICD 14 is expected to perform in sensing cardiac events according to a variety of sensing control parameters without requiring ICD 14 to be reprogrammed to perform actual cardiac event sensing and arrhythmia detection according to the variety of sensing control parameters, which may include both different sensing electrode vectors and different sensing threshold control parameters.

By providing the GUI 500 or other user interface for displaying the data relating to determined cardiac events, the likelihood of human error in identifying cardiac events that are expected to be sensed by ICD 14 and in determining and programming sensing control parameters is reduced. Furthermore, the techniques disclosed herein may reduce the complexity of programming a medical device to sense cardiac events to the degree of accuracy required for such cardiac event data to be used for controlling the delivery and timing of cardiac electrical stimulation therapies, e.g., pacing and/or CV/DF therapies. As such, the techniques disclosed herein may enable a medical device, such as ICD 14, to be programmed to sense cardiac events in a manner that is simplified, flexible, and patient-specific such that the ICD may reliably sense cardiac events to control delivery and timing of therapies.

FIG. 12 is a graph 550 of time to detect data that may be determined by processor 52 and may be generated as output for display on display unit 54 according to one example. Graph 550 may be included in GUI 500 of FIG. 11 in some examples. As indicated above, a graphical display of data based on determined cardiac events for each sensing electrode vector signal may be generated instead of or in addition to a tabular display.

The data represented by graph 550 represents another example of time to detect data determined by processor 52, different than the data shown in GUI 500. However, a similar graph could be generated and displayed in GUI 500, e.g., by clicking on the graph button 544 of GUI 500. In this example, the predicted time to VF detection (y-axis 552) is determined for each available sensitivity setting (x-axis 554) between 0.075 mV and 1.2 mV for each of two sensed cardiac electrical signals, shown by graphed lines 560 and 562, and for one constructed cardiac electrical signal (shown by graphed line 564). In this example, the time to detect VF from the first sensed cardiac electrical signal (S1), sensed between the pace/sense electrodes 28 and 30 (ring1-ring2) of lead 16 is plotted as the dotted line 562. The time to detect VF from the second sensed cardiac electrical signal (S2), sensed between pace/sense electrode 30 and housing 15, is plotted as the solid line 560. The time to detect VF from the third cardiac electrical signal (C3), which is a constructed cardiac electrical signal expected to be sensed between the pace/sense electrode 28 and housing 15, is plotted as the dashed line 564.

In this example, the predicted time to detect is approximately 6.5 seconds when the sensitivity is set to 0.075 mV for both the constructed C3 signal (graphed line 564) and the sensed S1 signal (graphed line 562). At the highest sensitivity setting of 1.2 mV, the predicted time to detect VF increases to approximately 7.8 seconds for the S1 signal (graphed line 562) and increases to approximately 6.9 seconds for the constructed C3 signal (graphed line 564). The predicted time to detect VF is approximately 8.8 seconds for the sensed S2 signal (graphed line 560) when the sensitivity is 0.75 mV and increases to approximately 10.8 seconds at the highest sensitivity of 1.2 mV.

Graph 550 may be generated by processor 52 as output for display in GUI 500 of FIG. 11, which may include simultaneous or selectable displays of the corresponding cardiac electrical signals, e.g., as shown in FIG. 11. The GUI may additionally or alternatively include a timing diagram of determined sensed cardiac event markers, tachyarrhythmia detection markers, and/or tabular listings of corresponding data as shown in FIG. 11. As indicated above, the graph 550 may be displayed as a pop-up window in GUI 500 in some examples.

The data represented in graph 550 may be used by processor 52 to determine recommended or acceptable sensing control parameter settings. For example, a sensing electrode vector that is associated with the shortest time to detect tachyarrhythmia may be selected as a recommended electrode vector. In another example, a sensing electrode vector corresponding to tachyarrhythmia detection at all analyzed sensitivity settings may be identified as an acceptable sensing electrode vector. A recommended sensing electrode vector may be identified as a sensing electrode vector with all times to detect for all analyzed sensitivity settings being within a threshold difference of each other or less than a threshold detection time limit. Conversely, when a sensing electrode vector is associated with a longest time to detect, or even a predicted failure to detect the tachyarrhythmia, the sensing electrode vector may be rejected for use as a sensing electrode vector or indicated as a non-acceptable or non-recommended sensing electrode vector. Other sensing control parameters, e.g., sensing threshold control parameters used for setting and adjusting the cardiac event sensing threshold, may be determined as acceptable or recommended settings based on the data represented in FIGS. 11 and 12.

In the example of FIG. 12, graph 550 is shown as a plot of time to VF detection (y-axis 552) as a function of sensitivity (x-axis 554). It is to be understood that the predicted time to detect an arrhythmia may be plotted as a function of a different sensing threshold control parameter when a different control parameter is selected to be analyzed. While only three cardiac electrical signals are represented in the graph 550, any number of cardiac electrical signals, sensed and/or constructed, analyzed by processor 52 may be represented in graph 550. A user interacting with the GUI may select which cardiac electrical signals are represented in the graph. In some examples, a user may select a sensing control parameter for programming in ICD 14 by clicking on a sensitivity setting and/or a sensing electrode vector that is displayed in the GUI that includes graph 550.

While graph 550 is shown as a plot of times to detect VF, it is contemplated that other data determined by processor 52 may additionally or alternatively be represented in a graph that is generated as part of a GUI. For example, determined cardiac event rates or cardiac event intervals may be plotted as a function of a sensing control parameter. The rate or intervals may be determined as the mean, median, maximum, minimum or other metric of the RRIs or PPIs that are determined from each analyzed cardiac electrical signal for each respective sensing threshold control parameter setting (or combinations of parameter settings).

Figure 13:
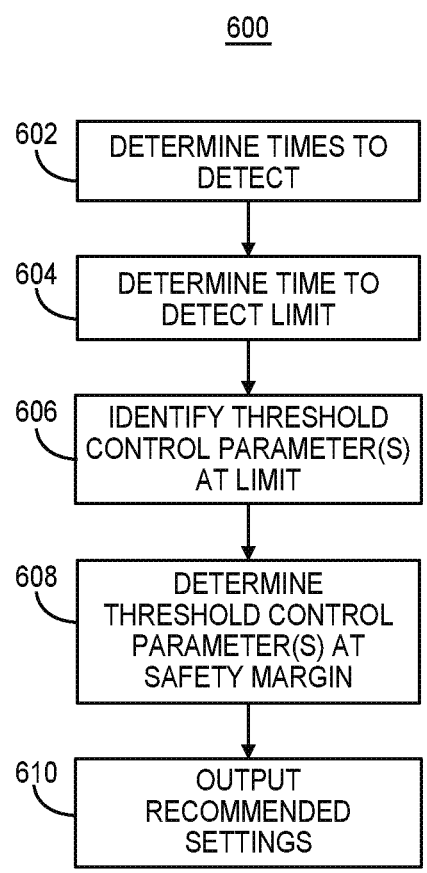
FIG. 13 is a flow chart of a method that may be performed by a medical device system processor for determining a recommended setting of a sensing control parameter according to one example.

FIG. 13 is a flow chart 600 of a method that may be performed by external device processor 52 (or control circuit 80) for determining a recommended sensing control parameter setting according to one example. At block 602 of FIG. 13, processor 52 may determine the expected times to detect a tachyarrhythmia from a cardiac electrical signal, sensed or constructed, corresponding to each sensing electrode vector under analysis and each sensing threshold control parameter setting (or combinations of sensing threshold control parameter settings). Using the illustrative examples of the two different data sets represented in FIGS. 11 and 12, processor 52 may determine the time to detect VF for each available sensitivity setting from each of at least two sensed cardiac electrical signals, sensed using different sensing electrode vectors, and at least one constructed cardiac electrical signal, constructed from the two sensed cardiac electrical signals.

The times to detect may be determined by determining sensed cardiac events for each combination of sensing electrode vector and sensing threshold control parameter(s), determining the associated expected sensed cardiac event intervals, identifying tachyarrhythmia intervals among the sensed cardiac event intervals, counting the tachyarrhythmia intervals to determine when the NID is reached for detecting the tachyarrhythmia, and summing all determined cardiac event intervals between the first tachyarrhythmia interval and the last tachyarrhythmia interval that contributed to the NID being reached. It is to be understood that, when a given set of sensing control parameters are programmed into ICD 14, the actual tachyarrhythmia detection by ICD 14 may be at the predicted time of the NID being reached or later due to processing delays. For instance, when additional detection criteria such as morphology-based detection criteria, noise rejection criteria or other criteria that require additional cardiac electrical signal analysis and processing are required by control circuit 80 in order to determine that all detection criteria are met before detecting the tachyarrhythmia, an actual tachyarrhythmia detection time may be later than a predicted time to NID being reached.

At block 604, processor 52 may determine a time to detect limit for each sensing electrode vector. In one example, the time to detect limit may be determined as the longest time to detect that is within a predetermined time interval of the shortest time to detect for a given sensing electrode vector. The predetermined time interval may be between 1 and 7 seconds, as examples, and is 2.5 seconds in one example. Using the data of FIG. 12 as an example, the shortest time to detect for the constructed cardiac electrical signal (C3) shown by graphed line 564 is approximately 6.5 seconds at sensitivity settings from 0.075 mV and less than 0.3 mV. The longest time to detect is approximately 6.9 seconds at sensitivity settings from 0.3 to 1.2 mV. Processor 52 may determine the time to detect limit as 2.5 seconds greater than the shortest time to detect, in this case 6.5 seconds plus 2.5 seconds or 9 seconds. All times to detect for the C3 sensing electrode vector fall within this time to detect limit. The time to detect limit may be determined as the detection time at the most sensitive sensitivity setting, e.g., 0.075 mV plus a predetermined time interval, e.g., 2 to 5 seconds or about 2.5 seconds as examples.

At block 606 of FIG. 13, processor 52 may identify the cardiac event sensing threshold control parameters that correspond to the time to detect limit. In the example of FIG. 12, processor 52 may identify the greatest sensitivity setting that resulted in the time to detect being at or less than the time to detect limit. This greatest (highest value) sensitivity setting corresponds to the lowest sensitivity of sensing circuit 86 in sensing cardiac events (highest sensing floor) that still results in the tachyarrhythmia detection within the time to detect limit. Continuing with the example given above, the greatest sensitivity setting for the C3 sensing electrode vector that results in a time to detect that is within 2.5 seconds of the shortest time to detect is 1.2 mV because the 6.9 seconds time to detect is less than the 9 second time to detect limit.

At block 608, processor 52 determines the cardiac event sensing threshold control parameter setting that provides a safety margin for detecting the tachyarrhythmia relative to the threshold control parameter setting identified at the time to detect limit. Using the same example of the C3 graphed line 564 in FIG. 12, the greatest sensitivity setting within the time to detect limit is 1.2 mV. A lower sensitivity setting may be determined at block 608 that provides a desired safety margin for sensing cardiac events, which may be a factor of the greatest sensitivity setting. For example, if a 2× safety margin for sensing cardiac events is desired, the sensitivity setting that is half of the greatest sensitivity setting associated with a time to detect within the time to detect limit may be determined at block 608. In this example, a sensitivity setting of 0.6 mV (half of 1.2 mV) is the recommended sensitivity setting for the sensing electrode vector associated with the constructed C3 signal represented by graphed line 564 to provide a 2× safety margin. When a 3× safety margin is desired, processor 52 may determine 0.45 mV as the recommended sensitivity setting. When a 4× safety margin is desired, processor 52 may determine 0.3 mV as the recommended sensitivity setting for the C3 sensing electrode vector.

With continued reference to FIG. 12, the time to detect limit corresponding to the S1 sensing electrode vector (graphed line 562) is approximately 9 seconds (using the predetermined time interval of 2.5 seconds plus the shortest time to detect of 6.5 seconds at a sensitivity of 0.75 mV). The longest time to detect for the S1 sensing electrode vector is 7.8 seconds, which is within the time to detect limit. The greatest sensitivity setting resulting in a time to detect within the time to detect limit is 1.2 mV. Processor 52 may determine the recommended cardiac event sensing threshold parameter at block 608 of FIG. 13 for the associated S1 sensing electrode vector as the sensitivity setting of 0.6 mV for a 2× safety margin for sensing cardiac events.

The time to detect limit for the S2 sensing electrode vector associated with graphed line 510 in FIG. 12 is approximately 11.1 seconds, based on an acceptable increase of 2.5 seconds from the shortest time to detect of approximately 8.6 seconds at 0.075 mV. The longest time to detect within this time to detect limit is identified by processor 52 as approximately 10.8 seconds at the 1.2 mV sensitivity setting, which is within the time to detect limit. Processor 52 may determine the recommended sensitivity setting as being 0.6 mV for a 2× safety margin for sensing cardiac events.

In these examples, processor 52 determines the time to detect limit as the time to detect at the lowest sensitivity setting, e.g., 0.075 mV in the example of FIG. 12, plus an acceptable increase in time to tachyarrhythmia detection, e.g., 2.5 seconds greater than the time to detect at the lowest sensitivity setting. Note that the lowest value of the sensitivity setting results in the highest sensitivity for sensing cardiac events because the cardiac event sensing threshold is decreased to the lowest possible amplitude (sensing floor), e.g., after the drop time interval as shown in FIG. 6. In other examples, the time to detect limit may be based on the shortest time to detect determined for all sensing electrode vectors plus an acceptable increase in time to detection. For example, the time to detect limit for all sensing control parameters being analyzed may be set to a predetermined interval (e.g., 2 to 7 seconds) greater than the shortest time to detect, approximately 6.5 ms for the constructed C3 signal (graphed line 564) at a sensitivity of 0.075 mV. In some examples, if the maximum time to detect for a given sensing electrode vector is greater than the time to detect limit, processor 52 may reject that sensing electrode vector in determining recommended or acceptable settings for sensing control parameters at block 610. Processor 52 may determine the time to detect limit as a percentage increase of the shortest time to detect for a given sensing electrode vector or out of all sensing electrode vectors in other examples. In still other examples, the time to detect limit may be a predetermined time interval, e.g., 12 seconds or less, 15 seconds or less, 24 seconds or less, or 30 seconds or less. The greatest sensitivity setting that results in a time to detect that is within the time to detect limit for a given sensing electrode vector may be used by processor 52 for determining a recommended sensitivity setting according to a desired safety margin at block 608.

In another example with reference to the example data represented in table 520 of FIG. 11, processor 52 may determine the shortest time to VF detection as 7.56 seconds for 0.075 mV sensitivity from the cardiac electrical signal sensed using the ring1-ring2 sensing electrode vector (row 526). The highest acceptable increase in the time to detect may be determined as 7.56 seconds plus an acceptable increase of 2.5 seconds for a time to detect limit of approximately 10 seconds. The greatest sensitivity setting that results in a VF detection time within the time to detect limit is 0.2 mV, with a time to detect of 8.32 seconds (11.34 seconds for sensitivity setting 0.3 mV exceeds the time to detect limit). Processor 52 may determine the 0.1 mV sensitivity setting as the recommended setting to provide a 2× safety margin (half of 0.2 mV) for sensing cardiac events using the Ring1-Ring2 sensing electrode vector.

For the second sensing electrode vector (Ring1-Can, row 528), the time to detect limit is 11.37 seconds (2.5 seconds plus the 8.87 seconds time to detect at sensitivity setting 0.075 mV). The greatest sensitivity setting falling within the time to detect limit is 0.3 mV, so the recommended setting for a 2× safety margin is 0.15 mV. For the third sensing electrode vector (Ring2-Can, row 530), the time to detect limit is 10.20 seconds (2.5 seconds plus 7.70 seconds at the 0.075 sensitivity setting). The greatest sensitivity setting resulting in a time to detect within this time to detect limit is 0.2 mV, so that the recommended sensitivity setting for a 2× safety margin is 0.1 mV for the third sensing electrode vector 530. It is to be understood that a different predetermined time interval greater than or less than 2.5 seconds may be used for determining the time to detect limit and other safety margins may be used to identify a recommended sensitivity setting for a given sensing electrode vector.

Returning to FIG. 13, at block 610, processor 52 may generate an output of the recommended sensing control parameter settings determined at block 608. As described above, the output may be a programming command transmitted to ICD 14, which may include a recommended sensing electrode vector and/or sensitivity setting (and/or one or more other sensing threshold control parameters). Additionally or alternatively, the output at block 610 may include generating a display of recommended or acceptable sensing control parameter settings in a GUI on display unit 54. For example, GUI 500 of FIG. 11 may indicate the recommended sensing threshold control parameter setting(s) for each sensing electrode vector that is analyzed by highlighting the recommended setting by distinct color, size, underlining or other stylized font or shading or color of a data cell in table 520 or a data point in graph 550, as examples.

The process of FIG. 13 may be repeated each time a tachyarrhythmia induction is performed and/or each time external device 40 interrogates ICD 14 and retrieves sensed cardiac electrical signal episodes corresponding to detected tachyarrhythmia episodes. Alternatively, the process of FIG. 13 may be performed upon command by a user interacting with user interface 56. For example, a user may select sensing electrode vectors and sensing threshold control parameters to be evaluated via GUI 500 and initiate a tachyarrhythmia induction. Processor 52 may receive the sensed cardiac electrical signals from ICD 14 during the tachyarrhythmia induction and process the sensed and constructed cardiac electrical signals for generating the determined cardiac events and data presented in GUI 500.

As indicated above, control circuit 80 of ICD 14 may be configured to perform some or all of the techniques disclosed herein. In that case, the process of FIG. 13 may be performed by control circuit 80 after detecting a tachyarrhythmia episode without waiting for communication with an external device. At block 610, control circuit 80 may adjust a sensing control parameter to a recommended setting determined at block 608. For example, if the sensitivity setting corresponding to a desired safety margin (which may be programmable) changes according to the determined times to detect for the currently selected sensing electrode vector, control circuit 80 may adjust the sensitivity setting at block 610 to the recommended setting determined at block 608. If a sensing electrode vector is determined to have a prolonged time to detect compared to other sensing electrode vectors (or is predicted to fail to detect the tachyarrhythmia at one or more sensing threshold control parameter settings) according to the post processing analysis, control circuit 80 may select a different sensing electrode vector at block 610.

Figure 14:
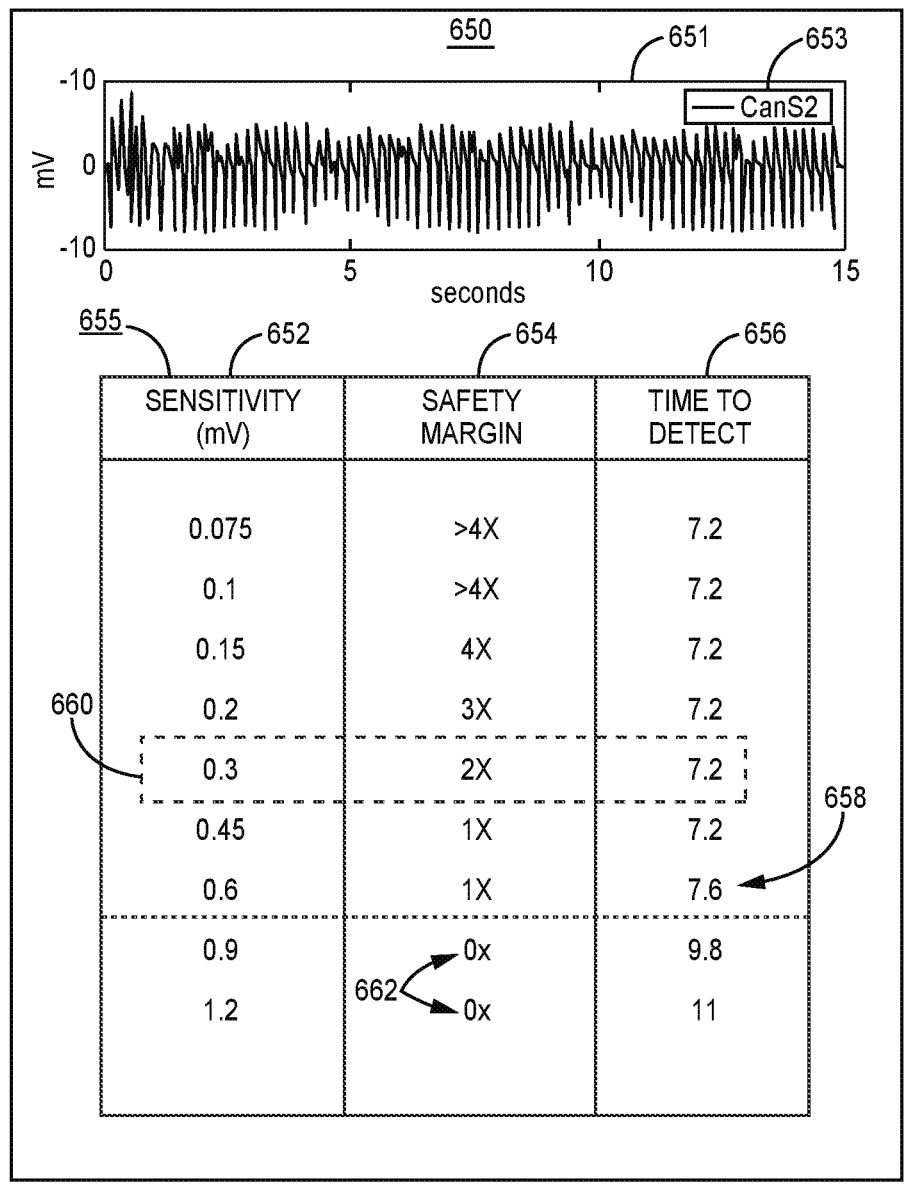
FIG. 14 is a GUI that may be generated for display on a display unit of a medical device according to one example.

FIG. 14 is a GUI 650 that may be generated as output by processor 52 for display on display unit 54 according to one example. GUI 650 may be generated by external device 40 for visualization of the performance of cardiac event sensing by ICD 14. GUI 650 may include a cardiac electrical signal window 651 that may display the cardiac electrical signal corresponding to a sensing electrode vector, which may be selectable by a user via a drop down or scrollable menu 653. GUI 650 may include a table 655 listing programmable sensing threshold control parameter settings, shown as sensitivity settings 652 in this example, and a corresponding time to detect tachyarrhythmia 656 as determined by processor 52, e.g., using the techniques described in conjunction with FIG. 9, for each of the sensitivity settings 652. The data shown in table 655 corresponds to the sensing electrode vector signal, sensed or constructed, selected in cardiac electrical signal window 651. It is to be understood that processor 52 may generate a table of data or tables of data that include the predicted time to detect the tachyarrhythmia, e.g., time to reach NID, for each sensitivity setting (or other sensing threshold control parameter setting or combinations of settings) for multiple sensing electrode vectors, sensed and constructed.

In this example, the time to detect limit is determined based on the time to detect at the lowest sensitivity setting of 0.075 mV (corresponding to highest sensitivity for sensing cardiac event signals). Processor 52 determines the time to detect limit by adding an acceptable increase to the time to detect at 0.075 mV sensitivity, e.g., by adding 2.5 seconds. The time to detect limit is 9.7 seconds in this example (7.2 seconds plus 2.5 seconds). Processor 52 may determine the greatest sensitivity setting at which the time to detect is equal to or less than the time to detect limit. In this example, the times to detect at sensitivity settings 0.9 mV and 1.2 mV (9.8 seconds and 11 seconds, respectively) are greater than the time to detect limit of 9.7 seconds. Table 655 may include a safety margin column 654 indicating the safety margin for each sensitivity setting as determined based on the greatest sensitivity setting that results in a time to detect that is less than or equal to the time to detect limit. When a sensitivity setting results in a time to detect that is greater than the limit, processor 52 may determine a Ox safety margin 662 for that sensitivity setting, as shown for sensitivity settings 0.9 and 1.2 mV. The GUI 650 generated by processor 52 may also denote these unacceptable sensitivity settings by demarcating these sensitivity settings 0.9 and 1.2 from other sensitivity settings by a dashed line (as shown), distinct color, size, or other stylized font, shading or other distinguishing display characteristics.

In the example shown, processor 52 identifies 0.6 mV as the greatest sensitivity setting that results in a time to detect of 7.6 seconds that is equal to or less than the time to detect limit of 9.7 seconds. Based on this sensitivity setting of 0.6 mV, the safety margin of each of the other sensitivity settings less than 0.6 mV may be determined by processor 52 and displayed in safety margin column 654. The safety margins displayed in column 654 are determined by dividing the greatest sensitivity setting 0.6 mV corresponding to a time to detect 658 within the time to detect limit by the lower sensitivity setting. In this example, 0.6 mV has a 1× safety margin, 0.3 mV has a 2× safety margin, 0.2 mV has a 3× safety margin and so on.

Processor 52 may determine a recommended sensitivity setting 660 that is a minimum desired safety margin for sensing cardiac electrical signals, e.g., a 2× safety margin. The safety margin may be rounded up to a whole number as shown. When a minimum 2× safety margin is programmed or desired for sensing cardiac electrical signals, the recommended sensitivity setting 660 is 0.3 mV in the example shown, half of 0.6 mV. As mentioned above, a table similar to table 650 may be generated by processor 52 and displayed on display unit 54 for each sensing electrode vector under analysis or a combined table displaying the sensitivity settings and corresponding safety margins and times to detect determined for each sensing electrode vector may be generated and displayed. The recommended sensing threshold control parameter, in this case sensitivity, for each sensing electrode vector may be highlighted in the table, e.g., by stylized font, highlighted by colored (e.g., green) or shaded cells in table 655, encircled by a border as shown in table 650 or the like.

In some examples, acceptable sensing threshold control parameter settings, e.g., all settings resulting in at least a 2× (or other specified) safety margin may be highlighted by color, bolding, or other stylized font, colored fill of cells in table 655 or other formatting options in addition to highlighting the recommended sensing threshold control parameter 660. For example, the rows corresponding to less than 0.3 mV sensitivity having a predicted safety margin for sensing cardiac events of at least 2× may be highlighted as acceptable sensitivity settings, e.g., in green or yellow font or cell fill. The recommended setting of 0.3 mV at the 2× safety margin may be highlighted by green font or green cell fill and/or enlarged, bolded or encircled to be distinguished as the recommended setting.

Additionally or alternatively, settings that are not considered acceptable, e.g., any setting with a 1× safety margin or less, may be shaded or grayed out, shown in red or displayed with other formatting of the table cells and/or font of the cell contents to indicate settings that are not recommended or not acceptable. In another example, all rows of table 655 corresponding to a 2× safety margin or more (0.3 mV sensitivity or less) may be shown in green. The recommended setting 660 at the 2× safety margin may be enlarged, bolded, encircled or otherwise formatted to stand out among the acceptable settings. The sensitivity settings that result in a 1× safety margin may be indicated as unacceptable settings, e.g., by displaying rows corresponding to 0.45 mV and 0.6 mV sensitivity in yellow. The rows corresponding to a time to detect beyond the time limit (or any rows corresponding to a predicted failure to detect the tachyarrhythmia) may be displayed in red, grayed out, or otherwise formatted to indicate that these settings (0.9 and 1.2 mV sensitivity in this example) are not recommended.

In the various GUIs described and shown herein, sensing control parameter settings, cardiac electrical signals corresponding to a sensing electrode vector, timing markers, tables, graphs, or other representations of determined sensed cardiac events and/or predicted tachyarrhythmia detections included in the display of the GUI may be formatted according to various formatting schemes that distinguish between acceptable, recommended and/or not recommended or not acceptable sensing control parameter settings. Such formatting schemes may include colors (e.g., green, yellow and red), shading, bolding, size or other formatting options to provide a visual representation to a user that readily discerns a recommended setting and/or acceptable settings from other settings of sensing control parameters. When a setting is acceptable or recommended, the displayed setting may be selectable by a user, e.g., by clicking on row 660, to initiate programming of the acceptable or recommended setting. When a setting is not acceptable or recommended, the display setting may not be selectable by a user. When the setting is clicked on or touched by a user in interacting with GUI 650, a warning or error message may occur indicating that the selection is not acceptable or recommended.

While table 655 is shown displaying times to detect tachyarrhythmia in column 656, other data that is based on the determined sensed cardiac events may be displayed in table 655, in addition to or instead of times to detect. For example, a column of table 655 may indicate whether tachyarrhythmia detection is made or not, which may be required to be within some maximum time limit, e.g., using the annotations VF, VT, or ND as examples. When no cardiac events are sensed according to a sensing control parameter setting, the indication "NS" may be included in table 655. In other examples, table 655 may include a column indicating a cardiac rate and/or cardiac event intervals determined by processor 52 from the selected cardiac electrical signal, which may be selected and displayed in window 651.

Figure 15:
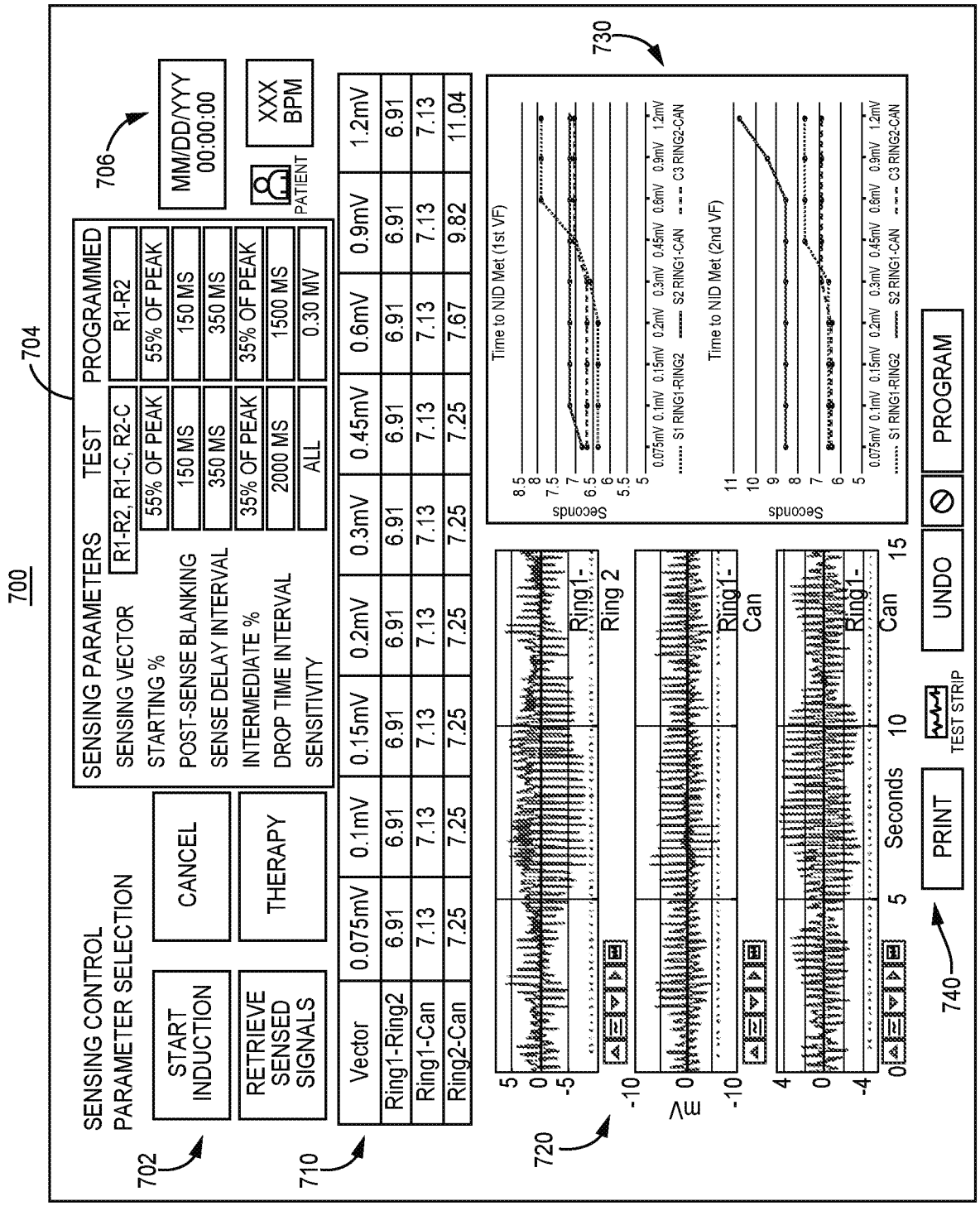
FIG. 15 is a diagram of a GUI that may be generated as output by a processor for display on a display unit of a device performing the disclosed techniques according to another example.

FIG. 15 is a diagram of a GUI 700 that may be generated as output by processor 52 for display on display unit 54 according to another example. GUI 700 may include a user input portion 702 to enable a user to start a tachyarrhythmia induction, cancel the tachyarrhythmia induction, retrieve sensed cardiac electrical signals from ICD 14, which may be stored by ICD 14 in response to detecting spontaneous tachyarrhythmia episodes, and select a therapy programming screen for programming tachyarrhythmia therapies.

GUI 700 may include a sensing parameter window 704 for listing programmable sensing control parameters and corresponding test settings selected for generating determined sensed event data and currently programmed settings stored in ICD 14. The test settings may be user inputs that enable the user to select which setting(s) of each programmable sensing control parameter is evaluated by processor 52 in determining sensed cardiac events and corresponding event intervals, rates and detected arrhythmias. In some examples, a user may input which sensing electrode vector signals are analyzed. For instance a user may select which signals are sensed by ICD 14 for transmission to external device 40 and/or which signals are constructed by selecting the vectors via a user input in sensing parameter window 704.

GUI 700 may include informational data 706 displayed as chiclets, icons, windows, or the like for displaying the date and time, providing user selectable patient information, patient heart rate or other informational data. GUI 700 may include other user input chiclets or icons, such as the user inputs 740 that enable a user to print data, print a cardiac electrical signal test strip, undo an action, or enable external device 40 to transmit a programming command, as a few examples.

GUI 700 may further include a data table 710, a cardiac electrical signal window 720, and/or data graph window 730. Table 710 may include data and information relating to the determined sensed cardiac events, event intervals, rates and/or predicted tachyarrhythmia detection determined by processor 52 upon processing selected cardiac electrical signals, constructed and/or sensed, according to selected sensing threshold control parameter settings. The cardiac electrical signal window 720 may display the cardiac signal episodes for each selected sensing electrode vector. User inputs included in the cardiac electrical signal window 720 may allow the user to move forward, backward, pause, freeze, increase or decrease the vertical scale or other adjustments to the display of the cardiac electrical signals.

One or more graphs may be displayed in data graph window 730. The graphs in window 730 may represent data determined by processor 52 for more than one tachyarrhythmia episode, induced or spontaneous. In the example shown, graphs of the predicted time to detect (time to NID met) for two different VF episodes each include all predicted times to detect for all available sensitivity settings for each of three different sensing electrode vectors, Features of the illustrative GUI 700 and other example GUIs illustrated or described herein may be combined in any combination or arrangement and are not limited to the combinations and arrangements shown here. Furthermore, a GUI presenting sensing control parameter settings and data may include multiple screens and windows that may be toggled between on display unit 54.

Figure 16:
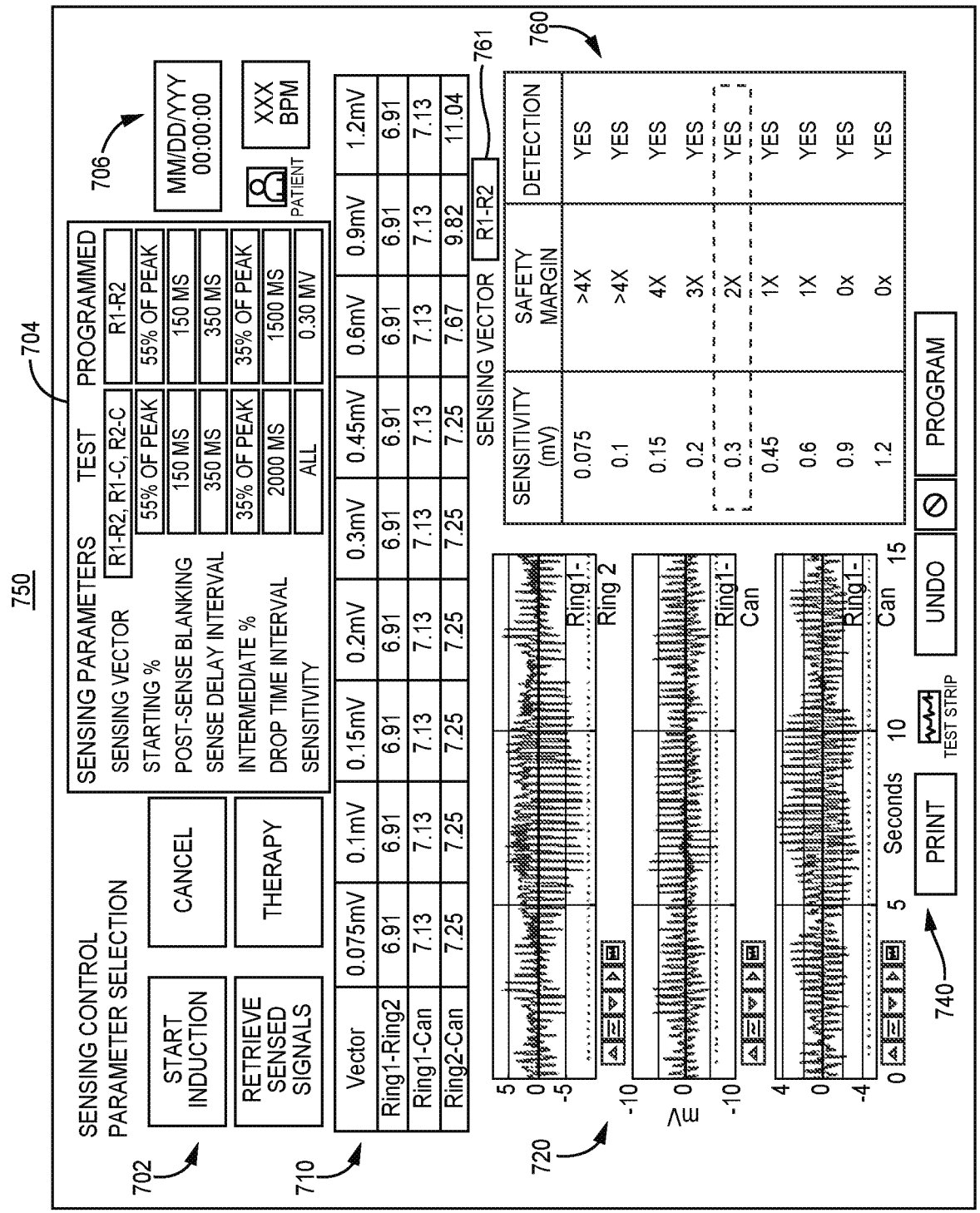
FIG. 16 is another example of GUI that may be displayed by a medical device to present a visualization of sensed cardiac event related data determined by a processor.

FIG. 16 is another example of GUI 750 that may be displayed by external device 40 to present a visualization of sensed cardiac event related data determined by processor 52. GUI 750 may include elements described above in conjunction with GUI 700 of FIG. 15. Reference numbers in FIG. 16 correspond to identically numbered elements shown in FIG. 15. GUI 750 may include a table of sensing control parameter settings 760 with an indication of safety margin and recommended sensing control parameter setting, as generally described above in conjunction with FIG. 14. In this example, a user input 761 may be included to allow a user to select which sensing electrode vector data is displayed in table 760. The selected sensing threshold control parameter settings, e.g., sensitivity settings, may be listed with corresponding safety margins for sensing cardiac events as determined by processor 52. The safety margins may be determined according to the methods described in conjunction with FIG. 13. In the example of FIG. 16, table 760 includes an indication (yes or no) as to whether tachyarrhythmia is expected to be detected by ICD 14 using the selected sensing control parameters (instead of listing the time to detect as shown in FIG. 14). In the example shown, tachyarrhythmia detection is expected for all sensitivity settings, but the time to detect at sensitivities 0.9 mV and 1.2 mV is longer than the time to detect limit resulting in a 0× safety margin being displayed.

A user may select different sensing electrode vectors (sensed or constructed) from a user input menu 761 for selecting which safety margin and tachyarrhythmia detection data is displayed. A user may accept the recommended sensitivity setting for the selected sensing electrode vector (as indicated by dashed box in table 760) by clicking on the program button in user inputs 740.

Figure 17:
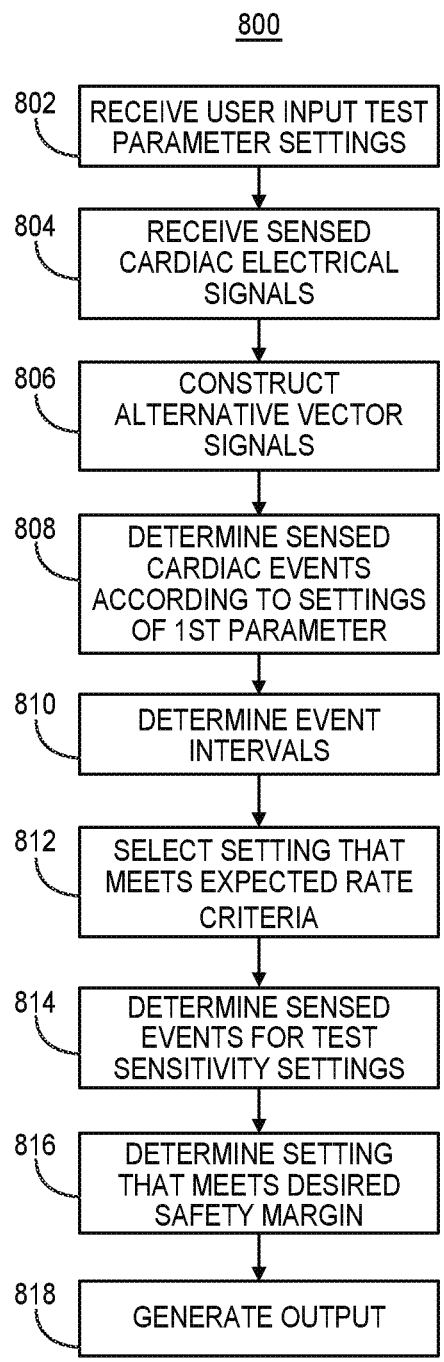
FIG. 17 is a flow chart of a method for determining acceptable or recommended sensing control parameters according to another example.

FIG. 17 is a flow chart 800 of a method for determining acceptable or recommended sensing control parameters according to another example. For convenience, the method of flow chart 800 is described in conjunction with external device processor 52 performing the processing and analysis though other processors included in a medical device system may perform all or portions of the method of FIG. 17. The process of flow chart 800 may be performed to generate data for display in a GUI to enable visualization of the performance of ICD in sensing cardiac events according to various sensing control parameters.

At block 802, a user interacting with a GUI displayed on display unit 54 may enter selected test sensing control parameters and may specify which ones of available programmable settings are to be tested for each selected sensing control parameter. External device processor 52 receives the user input test parameter settings, e.g., via the GUI or another user input interface device. For example, as shown in FIGS. 15 and 16, a user may select test settings in window 704 for one or more of the sensing electrode vector, post-sense blanking period, starting sensing threshold amplitude percentage of maximum peak, post-sense blanking period, sense delay interval, intermediate sensing threshold amplitude percentage of the maximum peak, drop time interval and/or sensitivity (all described above in conjunction with FIG. 6).

Sensitivity has been primarily described in the illustrative examples presented herein as the sensing threshold control parameter that is evaluated at multiple programmable settings for each one of the selected sensing electrode vectors. Sensitivity is a key sensing control parameter that can directly and significantly impact ICD sensitivity to detecting VF and providing necessary CV/DF therapy. However, other sensing threshold control parameters can impact the accuracy of cardiac event sensing and the sensitivity of ICD 14 in detecting VF or other arrhythmias. For example, different settings of other sensing threshold control parameters described herein may result in different determined sensed cardiac events due to oversensing of P-waves, T-waves, non-cardiac noise (muscle noise, electromagnetic interference, or other noise artifacts), or double counting of the QRS complex or undersensing of R-waves.

While selection and programming of sensitivity (and associated sensing electrode vector) may be a high priority in promoting safe and effective detection and treatment of VT/VF, selecting and programming the settings of other sensing threshold control parameters may address and improve cardiac event sensing performance of ICD 14 to avoid oversensing and/or undersensing of cardiac events according to patient-specific needs. For example, ICD sensing circuit 86 may oversense P-waves in some patients, which could lead to false VT/VF detection. In order to avoid P-wave oversensing, the drop time interval and/or the intermediate amplitude of the R-wave sensing threshold may be analyzed at multiple settings. In other patients, ICD sensing circuit 86 may oversense T-waves, e.g., due to a patient-specific long QT interval, requiring analysis for selecting the sense delay interval and/or the intermediate amplitude settings for controlling the R-wave sensing threshold. Sensitivity and sensing electrode vector settings may both need to be analyzed for identifying acceptable settings when oversensing of non-cardiac noise is occurring or R-waves are relatively low amplitude on a selected sensing electrode vector.

At block 804, processor 52 receives at least two sensed cardiac electrical signals from ICD 14. Processor 52 may construct at least one alternative sensing electrode vector signal using the two sensed cardiac electrical signals at block 806. As described above, multiple sensed cardiac electrical signals may be used to construct one or more additional cardiac electrical signals for evaluating performance of different sensing threshold control parameters in sensing cardiac events.

At block 808, processor 52 may determine the sensed cardiac events from each cardiac electrical signal selected for analysis according to a first sensing threshold control parameter. One or more settings of the first sensing threshold control parameter may be applied to each signal to determine the effect of different settings on cardiac event sensing and the resulting sensed cardiac event intervals (determined at block 810) and rate. In some examples, all available programmable settings of the first sensing threshold control parameter may be applied or a subset of settings that may be selected by the user. In some examples, the first sensing threshold control parameter tested at block 808 is any of the sensing control parameters listed above except sensitivity. Accordingly, the percentage used to set the starting threshold, the percentage used to set the intermediate threshold, the sense delay interval or the drop time interval may be the first sensing threshold control parameter evaluated at block 808. Because sensitivity significantly affects tachyarrhythmia detection in most patients, sensitivity may be evaluated after evaluating another sensing threshold control parameter that may need to be selected based on cardiac signal analysis for an individual patient due to noise, oversensing or other sensing issues, which may be patient specific.

At block 812, processor 52 determines a setting of the first sensing threshold control parameter that results in the determined cardiac events meeting expected rate criteria. The expected rate criteria may be a heart rate confirmed by a user or determined from an electrocardiogram input. In other examples, the expected rate criteria may be a tachyarrhythmia detection, which may be required to occur within a specified time limit. In some cases, when oversensing is an issue, a setting of the first sensing threshold control parameter may result in a determined sensed cardiac event rate that is faster than an expected rate. In other instances, undersensing may occur resulting in a determined sensed cardiac event rate that is slower than the expected rate.

When the determined cardiac event intervals for a first sensing threshold control parameter setting meet expected rate criteria, indicating that a possible oversensing or undersensing issue has been resolved, the setting identified at block 812 may be applied to the respective cardiac electrical signal being evaluated to redetermine sensed cardiac events according to each of the available sensitivity settings at block 814. When a sensing threshold control parameter other than sensitivity needs to be evaluated for a given patient, sensed cardiac events may be redetermined for all sensitivity settings (block 814) by processor 52 using the new setting of the first sensing threshold control parameter to determine the sensitivity setting that meets a desired safety margin (block 816) according to the techniques described above.

At block 818, processor 52 may generate an output, e.g., data for display in a GUI for visualization by a user and/or a programming command. The data representing the determined sensed cardiac events, determined sensed cardiac event intervals or rate, detection of a tachyarrhythmia and/or time to detect for each of the first sensing threshold control parameter settings may be presented in the GUI, similar to the GUIs described above. Additionally or alternatively, the first sensing threshold control parameter setting identified at block 812 may be indicated as the recommended setting and the data corresponding to testing different sensitivity settings using the recommended first sensing threshold control parameter setting may be presented in the GUI. The GUI enables a user to select and program an acceptable sensitivity, e.g., according to a desired safety margin, for sensing cardiac events when the first sensing threshold control parameter setting is at the recommended value.

In an illustrative example, ICD 14 may be oversensing P-waves in a patient requiring the drop time interval be increased to avoid P-wave oversensing. As shown in FIG. 15, a user may select a test drop time interval of 2.0 seconds when the programmed drop time interval is set at 1.5 seconds. Processor 52 may determine sensed cardiac events for all sensitivity settings at the new drop time interval of 2.0 seconds and generate a table, graph and/or timing diagram representing the determined sensed cardiac event data as described above. Processor 52 may determine the recommended sensitivity setting for achieving a desired safety margin for sensing cardiac events when the new drop time interval is applied.

For the sake of convenience, the flow chart 800 depicts determining sensed cardiac events from each cardiac electrical signal according to selected settings of the first sensing threshold parameter and subsequently determining sensed cardiac events according to each sensitivity setting. It is to be understood, however, that disclosed operations may be performed in a different order than shown in the flow charts presented herein or in parallel operations. For example, processor 52 may determine sensed cardiac events for all combinations of sensing control parameters (each sensing electrode vector, each setting of the first sensing threshold control parameter, and each setting of sensitivity). A user, interacting with a GUI such as the GUI 750 of FIG. 16 or other examples presented herein, may select the test setting of the first sensing threshold control parameter and the sensing electrode vector. Processor 52 may then generate the display representative of the determined sensed cardiac event data for all sensitivity settings and the selected sensing electrode vector and first sensing threshold control parameter setting. In this way, a user interacting with GUI 750 may switch between different combinations of sensing electrode vector and the first sensing threshold parameter setting to determine a combination and associated sensitivity setting that results in a desired safety margin and expected cardiac event rate being detected.

Accordingly, the techniques disclosed herein promote programming of an ICD or other cardiac device to a sensitivity setting that provides an acceptable safety margin for sensing cardiac events, e.g., for reliably detecting tachyarrhythmia, while avoiding oversensing of noise or other signals. When oversensing is an issue for an individual patient, the techniques disclosed herein enable a user to visualize how tachyarrhythmia detection is expected to be affected (e.g., by a change in time to detect) by a potential programming change before the programming change goes into effect. The analysis of multiple sensing electrode vector signals according to multiple sensing threshold control parameter settings may be performed efficiently without requiring each vector signal to be sensed by the ICD (or other medical device) and without having to perform time consuming operations of programming the ICD (or other medical device) to multiple different sensing control parameter settings in order to actually sense cardiac events by sensing circuit 86 and determine actual sensed cardiac event intervals and any corresponding arrhythmia detection. The expected performance of the ICD (or other medical device) in detecting a tachyarrhythmia may be determined for multiple sensing control parameter combinations based on a single tachyarrhythmia episode, induced or spontaneous, thereby eliminating the need to perform multiple tachyarrhythmia inductions. Furthermore, while FIG. 17 is described as identifying a first sensing threshold control parameter setting and then testing sensitivity settings, any combination of two or more sensing threshold control parameters, along with one or more sensing electrode vectors, may be evaluated according to the techniques disclosed herein.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising a processor configured to:
   receive at least a first sensed cardiac electrical signal and a second sensed cardiac electrical signal;
   construct a third cardiac electrical signal from the first sensed cardiac electrical signal and the second sensed cardiac electrical signal;
   from at least the third cardiac electrical signal, determine sensed cardiac events according to at least one setting of a cardiac event sensing threshold control parameter;
   determine a rate of the determined sensed cardiac events;
   determine that the rate meets expected rate criteria;
   determine that an associated sensing control parameter used to determine the sensed cardiac events is an acceptable sensing control parameter in response to the determined rate meeting the expected rate criteria; and
   generate an output representative of the determined sensed cardiac events.

2. The medical device of claim 1, wherein the processor is configured to determine the sensed cardiac events according to the at least one setting of the cardiac event sensing threshold control parameter by:
   adjusting at least one of a sensitivity, a starting amplitude of a cardiac event sensing threshold amplitude, an intermediate amplitude of the cardiac event sensing threshold amplitude, or a time interval used for making an amplitude adjustment to the cardiac event sensing threshold amplitude.

3. The medical device of claim 1, wherein:
   the device includes a display unit;
   the processor is further configured to:
      determine the acceptable sensing control parameter by determining an acceptable setting of at least one of a sensing electrode vector and a cardiac event sensing threshold control parameter based on the determined sensed cardiac events; and
      generate the output representative of the determined sensed cardiac events comprising the acceptable setting;
   the display unit being configured to display the acceptable setting.

4. The medical device of claim 1, wherein the processor is further configured to:
   detect a tachyarrhythmia based on the determined sensed cardiac events from at least one of the first cardiac electrical signal, the second cardiac electrical signal or the third cardiac electrical signal;
   determine at least one acceptable setting of a sensing control parameter by identifying a sensing control parameter associated with detecting the tachyarrhythmia.

5. The medical device of claim 4, wherein the processor is further configured to determine the at least one acceptable setting of the sensing control parameter by:
   determining a time to detect the tachyarrhythmia for each of a plurality of settings of a cardiac event sensing threshold control parameter for a given one of the first cardiac electrical signal, the second cardiac electrical signal and the third cardiac electrical signal;
   determining that the time to detect the tachyarrhythmia for at least one setting of the plurality of settings of the cardiac event sensing threshold control parameter is within a tachyarrhythmia detection time limit; and
   determining the at least one acceptable setting of the sensing control parameter by identifying the at least one setting of the plurality of settings of the cardiac event sensing threshold control parameter for which the determined time to detect the tachyarrhythmia is within the tachyarrhythmia detection time limit.

6. The medical device of claim 5, wherein the processor is further configured to determine the tachyarrhythmia detection time limit by:
determining a minimum time to detect the tachyarrhythmia from among the determined times to detect the tachyarrhythmia; and
determining the tachyarrhythmia detection time limit as the minimum time plus a predetermined increase in the time to detect the tachyarrhythmia.

7. The medical device of claim 5, wherein the processor is configured to:
determine the time to detect the tachyarrhythmia for each of the plurality of settings of the cardiac event sensing threshold control parameter by determining the time to detect the tachyarrhythmia for each of a plurality of sensitivity settings used to set a lowest amplitude of a cardiac event sensing threshold;
determine a highest value of the plurality of sensitivity settings for which the determined time to detect the tachyarrhythmia is within the tachyarrhythmia detection time limit; and
determine the at least one acceptable setting of the sensing control parameter by identifying an acceptable sensitivity setting that is a factor of the determined highest value of the plurality of sensitivity settings for which the determined time to detect the tachyarrhythmia is within the tachyarrhythmia detection time limit,
wherein the factor corresponds to a predetermined safety margin for sensing cardiac event signals.

8. The medical device of claim 1, wherein:
the processor receives the first cardiac electrical signal via a first sensing electrode vector comprising a first electrode and a second electrode;
the processor receives the second cardiac electrical signal via a second sensing electrode vector comprising the first electrode and a third electrode, and
the processor is configured to construct the third cardiac electrical signal corresponding to a third sensing electrode vector including the second electrode and the third electrode.

9. The device of claim 1, further comprising a display unit,
wherein the processor is configured to generate the output by generating data corresponding to the determined sensed cardiac events for display by the display unit in a graphical user interface.

10. A method comprising:
receiving at least a first sensed cardiac electrical signal and a second sensed cardiac electrical signal;
constructing a third cardiac electrical signal from the first sensed cardiac electrical signal and the second sensed cardiac electrical signal;
from at least the third cardiac electrical signal, determining sensed cardiac events according to at least one setting of a cardiac event sensing threshold control parameter;
detecting a tachyarrhythmia based on the determined sensed cardiac events from at least one of the first cardiac electrical signal, the second cardiac electrical signal or the third cardiac electrical signal;
determining a time to detect the tachyarrhythmia for each of a plurality of settings of a cardiac event sensing threshold control parameter for a given one of the first cardiac electrical signal, the second cardiac electrical signal and the third cardiac electrical signal;
determining that the time to detect the tachyarrhythmia for at least one setting of the plurality of settings of the cardiac event sensing threshold control parameter is within a tachyarrhythmia detection time limit;
determining at least one acceptable setting of the sensing control parameter by identifying the at least one setting of the plurality of settings of the cardiac event sensing threshold control parameter for which the determined time to detect the tachyarrhythmia is within the tachyarrhythmia detection time limit; and
generating an output representative of the determined sensed cardiac events.

11. The method of claim 10, wherein determining the sensed cardiac events according to at least one cardiac event sensing threshold control parameter comprises:
adjusting at least one of a sensitivity, a starting amplitude of a cardiac event sensing threshold amplitude, an intermediate amplitude of the cardiac event sensing threshold amplitude, or a time interval used for an amplitude adjustment to the cardiac event sensing threshold amplitude.

12. The method of claim 10, further comprising:
determining the acceptable setting by determining an acceptable setting of at least one of a sensing electrode vector and a cardiac event sensing threshold control parameter based on the determined sensed cardiac events;
generating the output representative of the determined sensed cardiac events comprising the acceptable setting; and
displaying the acceptable setting by a display unit.

13. The method of claim 12, further comprising determining at least one acceptable sensing control parameter setting based on the determined sensed cardiac events by:
determining a rate of the determined sensed cardiac events;
determining that the rate meets expected rate criteria; and
determining that an associated sensing control parameter used to determine the sensed cardiac events is the acceptable sensing control parameter in response to the rate meeting the expected rate criteria.

14. The method of claim 10, further comprising determining the tachyarrhythmia detection time limit by:
determining a minimum time to detect the tachyarrhythmia from among the determined times to detect the tachyarrhythmia; and
determining the tachyarrhythmia detection time limit as the minimum time plus a predetermined increase in the time to detect the tachyarrhythmia.

15. The method of claim 10, wherein:
determining the time to detect the tachyarrhythmia for each of the plurality of settings of the cardiac event sensing threshold control parameter comprises determining the time to detect the tachyarrhythmia for each of a plurality of sensitivity settings used to set a lowest amplitude of a cardiac event sensing threshold;
determining a highest value of the plurality of sensitivity settings for which a determined time to detect the tachyarrhythmia is within the tachyarrhythmia detection time limit; and
determining the at least one acceptable setting of the sensing control parameter by identifying an acceptable sensitivity setting that is a factor of the determined highest value of the plurality of sensitivity settings for which the determined time to detect the tachyarrhythmia is within the tachyarrhythmia detection time limit, wherein the factor corresponds to a predetermined safety margin for sensing cardiac event signals.

16. The method of claim 10, comprising:
receiving the first cardiac electrical signal via a first sensing electrode vector comprising a first electrode and a second electrode;
receiving the second cardiac electrical signal via a second sensing electrode vector comprising the first electrode and a third electrode, and
constructing the third cardiac electrical signal corresponding to a third sensing electrode vector including the second electrode and the third electrode.

17. The method of claim 10, wherein generating the output comprises:
generating data corresponding to the determined sensed cardiac events; and
displaying the generated data in a graphical user interface.

18. A non-transitory computer-readable medium storing a set of instructions which, when executed by a processor of a medical device, cause the device to:
receive at least a first sensed cardiac electrical signal and a second sensed cardiac electrical signal;
construct a third cardiac electrical signal from the first sensed cardiac electrical signal and the second sensed cardiac electrical signal;
from at least the third cardiac electrical signal, determine sensed cardiac events according to at least one setting of a cardiac event sensing threshold control parameter;
determine a rate of the determined sensed cardiac events;
determine that the rate meets expected rate criteria;
determine that an associated sensing control parameter used to determine the sensed cardiac events is an acceptable sensing control parameter in response to the determined rate meeting the expected rate criteria; and
generate an output representative of the determined sensed cardiac events.

19. A graphical user interface system, comprising:
a processor configured to:
receive at least a first sensed cardiac electrical signal and a second sensed cardiac electrical signal;
construct a third cardiac electrical signal from the first sensed cardiac electrical signal and the second sensed cardiac electrical signal;
from at least the third cardiac electrical signal, determine sensed cardiac events according to at least one setting of a cardiac event sensing threshold control parameter;
determine a rate of the determined sensed cardiac events;
determine that the rate meets expected rate criteria; and
determine that an associated sensing control parameter used to determine the sensed cardiac events is an acceptable sensing control parameter in response to the determined rate meeting the expected rate criteria;
wherein determining the acceptable sensing control parameter comprises determining an acceptable setting of at least one of a sensing electrode vector and a cardiac event sensing threshold control parameter for detecting tachyarrhythmia based on the determined sensed cardiac events; and
a display unit coupled to the processor and configured to:
display a visual representation of the acceptable setting.

* * * * *